(12) United States Patent
Fangrow

(10) Patent No.: US 11,497,904 B2
(45) Date of Patent: *Nov. 15, 2022

(54) SANITIZING CAPS FOR MEDICAL CONNECTORS

(71) Applicant: ICU Medical, Inc., San Clemente, CA (US)

(72) Inventor: Thomas F. Fangrow, Mission Viejo, CA (US)

(73) Assignee: ICU Medical, Inc., San Clemente, CA (US)

(*) Notice: Subject to any disclaimer, the term of this patent is extended or adjusted under 35 U.S.C. 154(b) by 115 days.

This patent is subject to a terminal disclaimer.

(21) Appl. No.: 16/918,896

(22) Filed: Jul. 1, 2020

(65) Prior Publication Data

US 2020/0330741 A1 Oct. 22, 2020

Related U.S. Application Data

(63) Continuation of application No. 16/340,300, filed as application No. PCT/US2017/056407 on Oct. 12, 2017, now Pat. No. 10,744,316.

(Continued)

(51) Int. Cl.
*A61M 39/16* (2006.01)
*A61L 2/18* (2006.01)
(Continued)

(52) U.S. Cl.
CPC ............. *A61M 39/162* (2013.01); *A61L 2/18* (2013.01); *A61M 5/00* (2013.01);
(Continued)

(58) Field of Classification Search
CPC .... A61L 2202/00; A61L 2202/11; A61L 2/00; A61L 2/16; A61L 2202/20;
(Continued)

(56) References Cited

U.S. PATENT DOCUMENTS 382,297 A 5/1888 Fry
559,697 A 5/1896 Tiugti et al.
(Continued)

FOREIGN PATENT DOCUMENTS

CA 2 148 847 12/1995
CA 2825217 3/2007
(Continued)

OTHER PUBLICATIONS

Antibiotic Lock Therapy Guidline, Standord Hospital and Clinics, Pharmacy Department Policies and Procedures, issued Jun. 2011.
(Continued)

*Primary Examiner* — Jason E Flick
(74) *Attorney, Agent, or Firm* — Knobbe Martens Olson & Bear, LLP

(57) ABSTRACT

Antiseptic caps that can be used to disinfect and/or protect medical connectors are disclosed herein. In some embodiments, the antiseptic cap can include a first chamber configured to be removably attached to the medical connector. Delivery systems for use with medical articles are also disclosed herein. In some embodiments, the delivery system comprises various dispensing systems for antiseptic caps and/or antiseptic cap holder assemblies. In some embodiments, the delivery system can be configured to permit the medical articles to be individually removable from the delivery system.

16 Claims, 30 Drawing Sheets

Related U.S. Application Data

(60) Provisional application No. 62/571,157, filed on Oct. 11, 2017, provisional application No. 62/527,897, filed on Jun. 30, 2017, provisional application No. 62/526,847, filed on Jun. 29, 2017, provisional application No. 62/490,952, filed on Apr. 27, 2017, provisional application No. 62/420,359, filed on Nov. 10, 2016, provisional application No. 62/408,546, filed on Oct. 14, 2016.

(51) Int. Cl.
*A61M 5/315* (2006.01)
*A61M 25/00* (2006.01)
*A61M 39/20* (2006.01)
*B08B 1/00* (2006.01)
*B08B 3/08* (2006.01)
*A61M 5/00* (2006.01)

(52) U.S. Cl.
CPC ........ *A61M 5/31511* (2013.01); *A61M 25/00* (2013.01); *A61M 25/0082* (2013.01); *A61M 39/165* (2013.01); *A61M 39/20* (2013.01); *B08B 1/003* (2013.01); *B08B 3/08* (2013.01); *A61L 2202/15* (2013.01); *A61L 2202/24* (2013.01); *A61M 2025/0019* (2013.01); *A61M 2205/0205* (2013.01); *A61M 2205/0238* (2013.01); *A61M 2209/06* (2013.01)

(58) Field of Classification Search
CPC ............. A61L 2202/23; A61L 2202/15; A61L 2202/24; A61L 2/18; A61M 25/0067; A61M 2025/0056; A61M 39/16; A61M 2025/0019; A61M 2205/0205; A61M 2205/0238; A61M 2209/06; A61M 25/00; A61M 25/0082; A61M 39/162; A61M 39/165; A61M 39/20; A61M 5/00; A61M 5/31511; B08B 1/003; B08B 3/08; B08B 1/00; B08B 1/001; B08B 1/007; B08B 3/00; B08B 3/04

See application file for complete search history.

(56) References Cited

U.S. PATENT DOCUMENTS

| | | |
|---|---|---|
| 877,946 A | 2/1908 | Overton |
| 975,939 A | 11/1910 | William et al. |
| 1,445,642 A | 2/1923 | O'Neill |
| 1,793,068 A | 2/1931 | Dickinson |
| 2,098,340 A | 11/1937 | Henahan |
| 2,436,297 A | 2/1948 | Guarnaschelli |
| 2,457,052 A | 12/1948 | Le Clair |
| 2,771,644 A | 11/1956 | Martin |
| 2,842,382 A | 7/1958 | Franck |
| 2,968,497 A | 1/1961 | Treleman |
| 3,127,892 A | 4/1964 | Bellamy, Jr. et al. |
| 3,262,448 A | 7/1966 | Ring et al. |
| 3,270,743 A | 9/1966 | Gingras |
| 3,301,392 A | 1/1967 | Eddingfield |
| 3,304,047 A | 2/1967 | Martin |
| 3,334,860 A | 8/1967 | Bolton, Jr. |
| 3,411,665 A | 11/1968 | Blum |
| 3,484,121 A | 12/1969 | Quinton |
| 3,485,416 A | 12/1969 | Fohrman |
| 3,538,950 A | 11/1970 | Porteners |
| 3,595,241 A | 7/1971 | Sheridan |
| 3,604,582 A | 9/1971 | Boudin |
| 3,707,972 A | 1/1973 | Villari et al. |
| 3,729,031 A | 4/1973 | Baldwin |
| 3,882,858 A | 5/1975 | Klemm |
| 3,977,401 A | 8/1976 | Pike |
| 3,977,517 A | 8/1976 | Kadlecik et al. |
| 3,987,930 A | 10/1976 | Fuson |
| 3,993,066 A | 11/1976 | Virag |
| 4,041,934 A | 8/1977 | Genese |
| 4,046,889 A | 9/1977 | Ondetti et al. |
| 4,052,511 A | 10/1977 | Cushman et al. |
| 4,053,052 A | 10/1977 | Jasper |
| 4,053,651 A | 10/1977 | Ondetti et al. |
| 4,066,067 A | 1/1978 | Micheli |
| 4,076,285 A | 2/1978 | Martinez |
| 4,078,686 A | 3/1978 | Karesh et al. |
| 4,079,738 A | 3/1978 | Dunn et al. |
| 4,095,810 A | 6/1978 | Kulie |
| 4,113,751 A | 9/1978 | Arnold |
| 4,121,585 A | 10/1978 | Becker, Jr. |
| 4,129,571 A | 12/1978 | Ondetti et al. |
| 4,133,441 A | 1/1979 | Mittleman et al. |
| 4,143,853 A | 3/1979 | Abramson |
| 4,150,845 A | 4/1979 | Kopacz et al. |
| 4,154,840 A | 5/1979 | Ondetti et al. |
| 4,154,960 A | 5/1979 | Ondetti et al. |
| 4,192,443 A | 3/1980 | McLaren |
| 4,194,509 A | 3/1980 | Pickering et al. |
| 4,195,632 A | 4/1980 | Parker et al. |
| 4,233,982 A | 11/1980 | Bauer et al. |
| 4,243,035 A | 1/1981 | Barrett |
| 4,245,635 A | 1/1981 | Kontos |
| 4,264,664 A | 4/1981 | Kunz |
| 4,280,632 A | 7/1981 | Yuhara |
| 4,294,370 A | 10/1981 | Toeppen |
| 4,317,446 A | 3/1982 | Ambrosio et al. |
| 4,324,239 A | 4/1982 | Gordon et al. |
| 4,325,368 A | 4/1982 | Kaemmerer |
| 4,331,783 A | 5/1982 | Stoy |
| 4,334,551 A | 6/1982 | Pfister |
| 4,335,756 A | 6/1982 | Sharp et al. |
| 4,337,327 A | 6/1982 | Stoy |
| 4,340,049 A | 7/1982 | Munsch |
| 4,340,052 A | 7/1982 | Dennehey et al. |
| 4,354,490 A | 10/1982 | Rogers |
| 4,369,294 A | 1/1983 | Stoy |
| 4,370,451 A | 1/1983 | Stoy |
| 4,379,458 A | 4/1983 | Bauer et al. |
| 4,379,874 A | 4/1983 | Stoy |
| 4,384,589 A | 5/1983 | Morris |
| 4,387,879 A | 6/1983 | Tauschinski |
| 4,390,016 A | 6/1983 | Riess |
| 4,397,442 A | 8/1983 | Larkin |
| 4,402,691 A | 9/1983 | Rosenthal et al. |
| 4,405,312 A | 9/1983 | Gross et al. |
| 4,417,890 A | 11/1983 | Dennehey et al. |
| 4,420,589 A | 12/1983 | Stoy |
| 4,427,126 A | 1/1984 | Ostrowsky |
| 4,430,073 A | 2/1984 | Bemis et al. |
| 4,432,764 A | 2/1984 | Lopez |
| 4,432,766 A | 2/1984 | Bellotti et al. |
| 4,436,125 A | 3/1984 | Blenkush |
| 4,439,179 A | 3/1984 | Lueders et al. |
| 4,439,184 A | 3/1984 | Wheeler |
| 4,440,207 A | 4/1984 | Genatempo et al. |
| 4,444,310 A | 4/1984 | Odell |
| 4,446,967 A | 5/1984 | Halkyard |
| 4,447,419 A | 5/1984 | Quadro |
| 4,457,749 A | 7/1984 | Bellotti et al. |
| 4,461,368 A | 7/1984 | Plourde |
| 4,461,896 A | 7/1984 | Portlock |
| 4,480,940 A | 11/1984 | Woodruff |
| 4,507,111 A | 3/1985 | Gordon et al. |
| 4,511,359 A | 4/1985 | Vaillancourt |
| 4,534,764 A | 8/1985 | Mittleman et al. |
| 4,538,836 A | 9/1985 | Kruetten |
| 4,559,043 A | 12/1985 | Whitehouse |
| 4,568,675 A | 2/1986 | Bush et al. |
| 4,585,758 A | 4/1986 | Huang et al. |
| 4,602,042 A | 7/1986 | Chantier et al. |
| 4,610,469 A | 9/1986 | Wolff-Mooij |
| 4,619,640 A | 10/1986 | Potolsky et al. |
| 4,623,332 A | 11/1986 | Lindmayer et al. |
| 4,624,664 A | 11/1986 | Peluso et al. |
| 4,626,545 A | 12/1986 | Taub |

(56) References Cited

U.S. PATENT DOCUMENTS

| | | |
|---|---|---|
| 4,629,159 A | 12/1986 | Wellenstam |
| 4,631,188 A | 12/1986 | Stoy |
| 4,642,091 A | 2/1987 | Richmond |
| 4,660,803 A | 4/1987 | Johnston et al. |
| 4,662,878 A | 5/1987 | Lindmayer |
| 4,666,057 A | 5/1987 | Come et al. |
| 4,666,427 A | 5/1987 | Larsson et al. |
| 4,671,306 A | 6/1987 | Spector |
| 4,671,412 A | 6/1987 | Gatten |
| 4,681,886 A | 7/1987 | Haugwitz et al. |
| 4,692,458 A | 9/1987 | Ryan et al. |
| 4,692,459 A | 9/1987 | Ryan et al. |
| 4,700,744 A | 10/1987 | Rutter et al. |
| 4,703,762 A | 11/1987 | Rathbone et al. |
| 4,705,790 A | 11/1987 | Hubele et al. |
| 4,723,603 A | 2/1988 | Plummer |
| 4,728,075 A | 3/1988 | Paradis |
| 4,728,321 A | 3/1988 | Chen |
| 4,738,668 A | 4/1988 | Bellotti et al. |
| 4,745,950 A | 5/1988 | Mathieu |
| 4,747,502 A | 5/1988 | Luenser |
| 4,748,160 A | 5/1988 | Bennion et al. |
| 4,752,983 A | 6/1988 | Grieshaber |
| 4,769,013 A | 9/1988 | Lorenz et al. |
| 4,774,964 A | 10/1988 | Bonaldo |
| 4,774,965 A | 10/1988 | Rodriguez et al. |
| 4,778,447 A | 10/1988 | Velde et al. |
| 4,781,702 A | 11/1988 | Herrli |
| 4,799,926 A | 1/1989 | Haber |
| 4,804,015 A | 2/1989 | Albinsson |
| 4,808,158 A | 2/1989 | Kreuzer et al. |
| 4,810,241 A | 3/1989 | Rogers |
| 4,811,847 A | 3/1989 | Reif et al. |
| 4,813,933 A | 3/1989 | Turner |
| 4,816,024 A | 3/1989 | Sitar et al. |
| 4,834,271 A | 5/1989 | Litwin |
| 4,862,913 A | 9/1989 | Wildfang |
| 4,874,366 A | 10/1989 | Zdeb et al. |
| 4,883,483 A | 11/1989 | Lindmayer |
| 4,889,255 A | 12/1989 | Schiemann et al. |
| 4,894,056 A | 1/1990 | Bommarito |
| 4,898,580 A | 2/1990 | Crowley |
| 4,915,687 A | 4/1990 | Sivert |
| 4,917,669 A | 4/1990 | Bonaldo |
| 4,919,658 A | 4/1990 | Badia |
| 4,927,019 A | 5/1990 | Haber et al. |
| 4,935,010 A | 6/1990 | Cox et al. |
| 4,941,873 A | 7/1990 | Fischer |
| 4,950,260 A | 8/1990 | Bonaldo |
| 4,957,637 A | 9/1990 | Cornell |
| 4,963,132 A | 10/1990 | Gibson |
| D313,277 S | 12/1990 | Haining |
| D314,050 S | 1/1991 | Sone |
| 4,983,161 A | 1/1991 | Dadson et al. |
| 4,985,017 A | 1/1991 | Theeuwes |
| 4,989,733 A | 2/1991 | Patry |
| 4,991,629 A | 2/1991 | Ernesto et al. |
| 4,997,371 A | 3/1991 | Fischer |
| 4,999,210 A | 3/1991 | Solomon et al. |
| 5,002,964 A | 3/1991 | Loscalzo |
| 5,006,114 A | 4/1991 | Rogers et al. |
| 5,015,238 A | 5/1991 | Solomon et al. |
| 5,019,096 A | 5/1991 | Fox, Jr. et al. |
| 5,021,059 A | 6/1991 | Kensey et al. |
| 5,024,657 A | 6/1991 | Needham et al. |
| 5,025,001 A | 6/1991 | Loscalzo et al. |
| 5,026,359 A | 6/1991 | Burroughs |
| 5,031,622 A | 7/1991 | LaHaye |
| 5,033,961 A | 7/1991 | Kandler et al. |
| 5,047,021 A | 9/1991 | Utterberg |
| 5,049,139 A | 9/1991 | Gilchrist |
| 5,059,186 A | 10/1991 | Yamamoto et al. |
| 5,065,783 A | 11/1991 | Ogle, II |
| 5,070,885 A | 12/1991 | Bonaldo |
| 5,071,411 A | 12/1991 | Hillstead |
| 5,071,413 A | 12/1991 | Utterberg |
| 5,098,385 A | 3/1992 | Walsh |
| 5,108,376 A | 4/1992 | Bonaldo |
| 5,122,123 A | 6/1992 | Vaillancourt |
| 5,127,626 A | 7/1992 | Hilal et al. |
| 5,129,824 A | 7/1992 | Keller |
| 5,139,483 A | 8/1992 | Ryan |
| 5,143,104 A | 9/1992 | Iba et al. |
| 5,147,333 A | 9/1992 | Raines |
| 5,154,703 A | 10/1992 | Bonaldo |
| 5,154,920 A | 10/1992 | Flesher et al. |
| 5,184,742 A | 2/1993 | DeCaprio et al. |
| 5,190,534 A | 3/1993 | Kendell |
| 5,195,957 A | 3/1993 | Tollini |
| RE34,223 E | 4/1993 | Bonaldo |
| 5,199,948 A | 4/1993 | McPhee |
| 5,201,725 A | 4/1993 | Kling |
| 5,203,775 A | 4/1993 | Frank et al. |
| 5,205,820 A | 4/1993 | Kriesel |
| 5,205,821 A | 4/1993 | Kruger et al. |
| 5,207,706 A | 5/1993 | Menaker |
| 5,211,634 A | 5/1993 | Vaillancourt |
| 5,212,204 A | 5/1993 | Keefer et al. |
| 5,215,537 A | 6/1993 | Lynn et al. |
| 5,240,675 A | 8/1993 | Wilk et al. |
| 5,242,421 A | 9/1993 | Chan |
| 5,242,425 A | 9/1993 | White et al. |
| 5,246,011 A | 9/1993 | Caillouette |
| 5,250,550 A | 10/1993 | Keefer et al. |
| 5,251,873 A | 10/1993 | Atkinson et al. |
| D342,134 S | 12/1993 | Mongeon |
| 5,269,771 A | 12/1993 | Thomas et al. |
| 5,278,192 A | 1/1994 | Fung et al. |
| 5,281,206 A | 1/1994 | Lopez |
| 5,284,475 A | 2/1994 | Mackal |
| 5,295,657 A | 3/1994 | Atkinson |
| 5,297,310 A | 3/1994 | Cox et al. |
| 5,301,686 A | 4/1994 | Newman |
| 5,304,130 A | 4/1994 | Button |
| 5,306,243 A | 4/1994 | Bonaldo |
| 5,312,377 A | 5/1994 | Dalton |
| 5,324,270 A | 6/1994 | Kayan et al. |
| 5,324,647 A | 6/1994 | Rubens et al. |
| 5,330,426 A | 7/1994 | Kriesel et al. |
| 5,330,450 A | 7/1994 | Lopez |
| 5,330,899 A | 7/1994 | Devaughn et al. |
| 5,337,730 A | 8/1994 | Maguire |
| 5,344,414 A | 9/1994 | Lopez et al. |
| 5,352,410 A | 10/1994 | Hansen et al. |
| 5,354,267 A | 10/1994 | Niermann et al. |
| 5,356,396 A | 10/1994 | Wyatt et al. |
| 5,360,413 A | 11/1994 | Leason et al. |
| 5,366,505 A | 11/1994 | Farber |
| 5,366,997 A | 11/1994 | Keefer et al. |
| 5,370,614 A | 12/1994 | Amundson et al. |
| 5,370,636 A | 12/1994 | Von Witzleben |
| 5,370,640 A | 12/1994 | Kolff |
| 5,375,589 A | 12/1994 | Bhatta |
| 5,380,306 A | 1/1995 | Brinon |
| 5,380,758 A | 1/1995 | Stamler et al. |
| 5,391,150 A | 2/1995 | Richmond |
| 5,402,826 A | 4/1995 | Molnar et al. |
| 5,405,331 A | 4/1995 | Behnke et al. |
| 5,405,333 A | 4/1995 | Richmond |
| 5,405,919 A | 4/1995 | Keefer et al. |
| 5,407,807 A | 4/1995 | Markus |
| 5,409,012 A | 4/1995 | Sahatjian |
| 5,411,499 A | 5/1995 | Dudar et al. |
| 5,417,673 A | 5/1995 | Gordon |
| 5,425,465 A | 6/1995 | Healy |
| 5,428,070 A | 6/1995 | Cooke et al. |
| 5,433,330 A | 7/1995 | Yatsko et al. |
| 5,433,705 A | 7/1995 | Giebel et al. |
| 5,439,451 A | 8/1995 | Collinson et al. |
| 5,441,487 A | 8/1995 | Vedder |
| 5,445,623 A | 8/1995 | Richmond |
| 5,456,668 A | 10/1995 | Ogle, II |
| 5,456,675 A | 10/1995 | Wolbring et al. |
| 5,464,399 A | 11/1995 | Boettger |

(56) References Cited

U.S. PATENT DOCUMENTS

| | | |
|---|---|---|
| 5,470,307 A | 11/1995 | Lindall |
| 5,470,327 A | 11/1995 | Helgren et al. |
| 5,471,706 A | 12/1995 | Wallock et al. |
| 5,474,536 A | 12/1995 | Bonaldo |
| 5,480,393 A | 1/1996 | Bommarito |
| 5,492,147 A | 2/1996 | Challender et al. |
| 5,496,288 A | 3/1996 | Sweeney |
| 5,501,426 A | 3/1996 | Atkinson et al. |
| 5,507,733 A | 4/1996 | Larkin et al. |
| 5,507,744 A | 4/1996 | Tay et al. |
| 5,514,177 A | 5/1996 | Kurz et al. |
| 5,518,026 A | 5/1996 | Benjey |
| 5,520,665 A | 5/1996 | Fleetwood |
| 5,520,666 A | 5/1996 | Choudhury et al. |
| 5,485,827 A | 6/1996 | Zapol et al. |
| 5,525,357 A | 6/1996 | Keefer et al. |
| 5,531,695 A | 7/1996 | Swisher |
| 5,533,708 A | 7/1996 | Atkinson et al. |
| 5,533,983 A | 7/1996 | Haining |
| 5,535,785 A | 7/1996 | Werge et al. |
| 5,536,241 A | 7/1996 | Zapol |
| 5,536,258 A | 7/1996 | Folden |
| 5,540,661 A | 7/1996 | Tomisaka et al. |
| 5,545,614 A | 8/1996 | Stamler et al. |
| 5,549,566 A | 8/1996 | Elias et al. |
| 5,549,651 A | 8/1996 | Lynn |
| 5,552,115 A | 9/1996 | Malchesky |
| 5,552,118 A | 9/1996 | Mayer |
| 5,554,127 A | 9/1996 | Crouther et al. |
| 5,554,135 A | 9/1996 | Menyhay |
| 5,555,908 A | 9/1996 | Edwards et al. |
| 5,569,235 A | 10/1996 | Ross et al. |
| 5,573,516 A | 11/1996 | Tyner |
| 5,575,769 A | 11/1996 | Vaillancourt |
| 5,578,059 A | 11/1996 | Patzer |
| 5,580,530 A | 12/1996 | Kowatsch et al. |
| 5,584,819 A | 12/1996 | Kopfer |
| 5,591,137 A | 1/1997 | Stevens |
| 5,591,143 A | 1/1997 | Trombley, III et al. |
| 5,597,536 A | 1/1997 | Mayer |
| 5,599,352 A | 2/1997 | Dinh et al. |
| 5,605,696 A | 2/1997 | Eury et al. |
| 5,607,072 A | 3/1997 | Rigney et al. |
| 5,613,615 A | 3/1997 | Zeyfang et al. |
| 5,616,130 A | 4/1997 | Mayer |
| 5,620,088 A | 4/1997 | Martin et al. |
| 5,620,427 A | 4/1997 | Werschmidt et al. |
| 5,624,402 A | 4/1997 | Imbert |
| 5,628,733 A | 5/1997 | Zinreich et al. |
| RE35,539 E | 6/1997 | Bonaldo |
| 5,645,538 A | 7/1997 | Richmond |
| 5,665,077 A | 9/1997 | Resen et al. |
| 5,674,206 A | 10/1997 | Allton et al. |
| 5,676,346 A | 10/1997 | Leinsing |
| 5,685,835 A | 11/1997 | Brugger |
| 5,685,866 A | 11/1997 | Lopez |
| 5,685,868 A | 11/1997 | Lundquist |
| 5,688,253 A | 11/1997 | Lundquist |
| 5,694,978 A | 12/1997 | Heilmann et al. |
| 5,699,821 A | 12/1997 | Paradis |
| 5,700,248 A | 12/1997 | Lopez |
| 5,702,017 A | 12/1997 | Goncalves |
| 5,716,339 A | 2/1998 | Tanaka et al. |
| 5,722,537 A | 3/1998 | Sigler |
| 5,735,826 A | 4/1998 | Richmond |
| 5,738,144 A | 4/1998 | Rogers |
| 5,743,892 A | 4/1998 | Loh et al. |
| 5,749,861 A | 5/1998 | Guala et al. |
| 5,763,409 A | 6/1998 | Bayol et al. |
| 5,770,645 A | 6/1998 | Stamler et al. |
| 5,776,116 A | 7/1998 | Lopez |
| 5,782,808 A | 7/1998 | Folden |
| 5,782,816 A | 7/1998 | Werschmidt et al. |
| 5,785,693 A | 7/1998 | Haining |
| 5,792,120 A | 8/1998 | Menyhay |
| 5,797,887 A | 8/1998 | Rosen et al. |
| 5,806,831 A | 9/1998 | Paradis |
| 5,810,792 A | 9/1998 | Fang, Jr. et al. |
| 5,814,024 A | 9/1998 | Thompson et al. |
| 5,814,666 A | 9/1998 | Green et al. |
| 5,820,601 A | 10/1998 | Mayer |
| 5,820,604 A | 10/1998 | Fox et al. |
| 5,827,244 A | 10/1998 | Boettger |
| 5,839,715 A | 11/1998 | Leinsing |
| 5,848,994 A | 12/1998 | Richmond |
| 5,902,631 A | 5/1999 | Wang et al. |
| 5,941,857 A | 8/1999 | Nguyen et al. |
| 5,947,954 A | 9/1999 | Bonaldo |
| 5,951,519 A | 9/1999 | Utterberg |
| 5,954,957 A | 9/1999 | Chin-Loy et al. |
| 5,971,972 A | 10/1999 | Rosenbaum |
| D416,086 S | 11/1999 | Parris et al. |
| 5,989,229 A | 11/1999 | Chiappetta |
| 5,994,444 A | 11/1999 | Trescony |
| 6,029,946 A | 2/2000 | Doyle |
| 6,036,171 A | 3/2000 | Weinheimer et al. |
| 6,041,805 A | 3/2000 | Gydesen et al. |
| 6,045,539 A | 4/2000 | Menyhay |
| 6,045,623 A | 4/2000 | Cannon |
| 6,050,978 A | 4/2000 | Orr et al. |
| 6,059,107 A | 5/2000 | Nosted et al. |
| 6,063,062 A | 5/2000 | Paradis |
| 6,068,011 A | 5/2000 | Paradis |
| 6,068,475 A | 5/2000 | Stoyka, Jr. et al. |
| 6,068,617 A | 5/2000 | Richmond |
| 6,071,413 A | 6/2000 | Dyke |
| 6,079,432 A | 6/2000 | Paradis |
| 6,087,479 A | 7/2000 | Stamler et al. |
| 6,093,743 A | 7/2000 | Lai et al. |
| 6,095,356 A | 8/2000 | Rits |
| 6,099,519 A | 8/2000 | Olsen et al. |
| 6,105,812 A | 8/2000 | Riordan |
| 6,106,502 A | 8/2000 | Richmond |
| 6,113,068 A | 9/2000 | Ryan |
| 6,113,572 A | 9/2000 | Gailey et al. |
| 6,116,468 A | 9/2000 | Nilson |
| 6,117,114 A | 9/2000 | Paradis |
| 6,126,640 A | 10/2000 | Tucker |
| 6,142,446 A | 11/2000 | Leinsing |
| 6,143,318 A | 11/2000 | Gilchrist et al. |
| 6,146,363 A | 11/2000 | Giebel et al. |
| 6,152,913 A | 11/2000 | Feith et al. |
| 6,158,614 A | 12/2000 | Haines et al. |
| 6,170,522 B1 | 1/2001 | Tanida |
| 6,171,287 B1 | 1/2001 | Lynn et al. |
| 6,174,539 B1 | 1/2001 | Stamler et al. |
| 6,179,141 B1 | 1/2001 | Nakamura |
| 6,183,450 B1 | 2/2001 | Lois |
| 6,202,870 B1 | 3/2001 | Pearce |
| 6,202,901 B1 | 3/2001 | Gerber et al. |
| 6,206,134 B1 | 3/2001 | Stark et al. |
| 6,206,860 B1 | 3/2001 | Richmond |
| 6,207,855 B1 | 3/2001 | Toone et al. |
| 6,217,564 B1 | 4/2001 | Peters et al. |
| 6,227,391 B1 | 5/2001 | King |
| 6,232,406 B1 | 5/2001 | Stoy |
| 6,232,434 B1 | 5/2001 | Stamler et al. |
| 6,237,800 B1 | 5/2001 | Barrett et al. |
| 6,242,393 B1 | 6/2001 | Ishida et al. |
| 6,245,048 B1 | 6/2001 | Fangrow et al. |
| 6,245,056 B1 | 6/2001 | Walker et al. |
| 6,248,380 B1 | 6/2001 | Kocher et al. |
| 6,250,315 B1 | 6/2001 | Ernster |
| 6,255,277 B1 | 7/2001 | Stamler et al. |
| 6,267,754 B1 | 7/2001 | Peters |
| 6,299,132 B1 | 10/2001 | Weinheimer et al. |
| 6,315,113 B1 | 11/2001 | Britton et al. |
| 6,315,761 B1 | 11/2001 | Shcherbina et al. |
| 6,359,167 B2 | 3/2002 | Toone et al. |
| 6,359,182 B1 | 3/2002 | Stamler et al. |
| 6,375,231 B1 | 4/2002 | Picha et al. |
| 6,379,660 B1 | 4/2002 | Saavedra et al. |
| 6,379,691 B1 | 4/2002 | Tedeschi et al. |
| 6,394,983 B1 | 5/2002 | Mayoral et al. |

(56) References Cited

U.S. PATENT DOCUMENTS

| | | |
|---|---|---|
| 6,402,207 B1 | 6/2002 | Segal et al. |
| 6,403,759 B2 | 6/2002 | Stamler et al. |
| 6,409,716 B1 | 6/2002 | Sahatjian et al. |
| 6,428,520 B1 | 8/2002 | Lopez |
| 6,431,219 B1 | 8/2002 | Redler et al. |
| 6,444,318 B1 | 9/2002 | Guire et al. |
| 6,468,259 B1 | 10/2002 | Djokic et al. |
| 6,471,978 B1 | 10/2002 | Stamler et al. |
| 6,488,951 B2 | 12/2002 | Toone et al. |
| 6,491,965 B1 | 12/2002 | Berry et al. |
| 6,499,719 B1 | 12/2002 | Clancy et al. |
| 6,508,792 B2 | 1/2003 | Szames et al. |
| 6,508,807 B1 | 1/2003 | Peters |
| 6,538,116 B2 | 3/2003 | Stamler et al. |
| 6,541,802 B2 | 4/2003 | Doyle |
| 6,543,745 B1 | 4/2003 | Enerson |
| 6,550,493 B2 | 4/2003 | Williamson et al. |
| 6,555,504 B1 | 4/2003 | Ayai et al. |
| 6,562,781 B1 | 5/2003 | Berry et al. |
| 6,581,906 B2 | 6/2003 | Pott et al. |
| 6,583,311 B2 | 6/2003 | Toone et al. |
| 6,585,691 B1 | 7/2003 | Vitello |
| 6,595,964 B2 | 7/2003 | Finley et al. |
| 6,595,981 B2 | 7/2003 | Huet |
| 6,605,294 B2 | 8/2003 | Sawhney |
| 6,605,751 B1 | 8/2003 | Gibbins et al. |
| 6,609,696 B2 | 8/2003 | Enerson |
| 6,632,199 B1 | 10/2003 | Tucker et al. |
| 6,634,498 B2 | 10/2003 | Kayerod et al. |
| 6,656,217 B1 | 12/2003 | Herzog, Jr. et al. |
| 6,666,852 B2 | 12/2003 | Niedospial, Jr. |
| 6,673,891 B2 | 1/2004 | Stamler et al. |
| 6,679,395 B1 | 1/2004 | Pfefferkorn et al. |
| 6,679,870 B1 | 1/2004 | Finch et al. |
| 6,681,803 B2 | 1/2004 | Taneya et al. |
| 6,685,694 B2 | 2/2004 | Finch et al. |
| 6,692,468 B1 | 2/2004 | Waldenburg |
| 6,695,817 B1 | 2/2004 | Fangrow |
| 6,716,396 B1 | 4/2004 | Anderson |
| 6,722,705 B2 | 4/2004 | Korkor |
| 6,725,492 B2 | 4/2004 | Moore et al. |
| 6,745,998 B2 | 6/2004 | Doyle |
| 6,786,884 B1 | 9/2004 | DeCant, Jr. et al. |
| 6,808,510 B1 | 10/2004 | DiFiore |
| 6,827,766 B2 | 12/2004 | Carnes et al. |
| 6,840,501 B2 | 1/2005 | Doyle |
| 6,871,087 B1 | 3/2005 | Hughes et al. |
| 6,875,205 B2 | 4/2005 | Leinsing |
| 6,875,840 B2 | 4/2005 | Stamler et al. |
| 6,887,994 B2 | 5/2005 | Stamler et al. |
| 6,899,315 B2 | 5/2005 | Mailville et al. |
| 6,911,025 B2 | 6/2005 | Miyahar |
| 6,916,051 B2 | 7/2005 | Fisher |
| 6,929,005 B2 | 8/2005 | Sullivan et al. |
| 6,943,035 B1 | 9/2005 | Davies et al. |
| 6,955,669 B2 | 10/2005 | Curutcharry |
| 6,964,406 B2 | 11/2005 | Doyle |
| 7,004,934 B2 | 2/2006 | Vaillancourt |
| 7,015,347 B2 | 3/2006 | Toone et al. |
| 7,030,238 B2 | 4/2006 | Stamler et al. |
| 7,037,302 B2 | 5/2006 | Vaillancourt |
| 7,040,598 B2 | 5/2006 | Raybuck |
| 7,044,441 B2 | 5/2006 | Doyle |
| 7,045,585 B2 | 5/2006 | Berry et al. |
| 7,049,308 B2 | 5/2006 | Stamler et al. |
| 7,052,711 B2 | 5/2006 | West et al. |
| 7,056,308 B2 | 6/2006 | Utterberg |
| 7,067,659 B2 | 6/2006 | Stamler et al. |
| 7,081,109 B2 | 7/2006 | Tighe et al. |
| 7,083,605 B2 | 8/2006 | Miyahara |
| 7,087,709 B2 | 8/2006 | Stamler et al. |
| 7,097,850 B2 | 8/2006 | Chappa et al. |
| 7,100,891 B2 | 9/2006 | Doyle |
| 7,125,396 B2 | 10/2006 | Leinsing et al. |
| 7,140,592 B2 | 11/2006 | Phillips |
| 7,147,625 B2 | 12/2006 | Sarangapani et al. |
| 7,160,272 B1 | 1/2007 | Eyal et al. |
| 7,182,313 B2 | 2/2007 | Doyle |
| 7,195,615 B2 | 3/2007 | Tan |
| 7,198,611 B2 | 4/2007 | Connell et al. |
| 7,244,249 B2 | 7/2007 | Leinsing et al. |
| 7,259,250 B2 | 8/2007 | Stamler et al. |
| 7,279,176 B1 | 10/2007 | West et al. |
| 7,282,186 B2 | 10/2007 | Lake, Jr. et al. |
| 7,306,197 B2 | 12/2007 | Parrino et al. |
| 7,306,198 B2 | 12/2007 | Doyle |
| 7,306,566 B2 | 12/2007 | Raybuck |
| 7,309,326 B2 | 12/2007 | Fangrow, Jr. |
| 7,316,669 B2 | 1/2008 | Ranalletta |
| 7,347,458 B2 | 3/2008 | Rome et al. |
| 7,347,853 B2 | 3/2008 | DiFiore et al. |
| 7,350,764 B2 | 4/2008 | Raybuck |
| 7,361,164 B2 | 4/2008 | Simpson et al. |
| 7,417,109 B2 | 8/2008 | Stamler et al. |
| 7,431,712 B2 | 10/2008 | Kim |
| 7,442,402 B2 | 10/2008 | Chudzik et al. |
| 7,452,349 B2 | 11/2008 | Miyahar |
| 7,485,107 B2 | 2/2009 | DiFiore et al. |
| 7,491,192 B2 | 2/2009 | DiFiore |
| 7,497,484 B2 | 3/2009 | Ziman |
| 7,516,846 B2 | 4/2009 | Hansen |
| 7,588,563 B2 | 9/2009 | Guala |
| 7,611,505 B2 | 11/2009 | Ranalletta et al. |
| 7,614,426 B2 | 11/2009 | Kitani et al. |
| 7,615,034 B2 | 11/2009 | DiFiore |
| 7,625,907 B2 | 12/2009 | Stamler et al. |
| 7,635,344 B2 | 12/2009 | Tennican et al. |
| D607,325 S | 1/2010 | Rogers et al. |
| 7,645,274 B2 | 1/2010 | Whitley |
| 7,651,481 B2 | 1/2010 | Raybuck |
| 7,666,170 B2 | 2/2010 | Guala |
| 7,708,714 B2 | 5/2010 | Connell et al. |
| 7,731,678 B2 | 6/2010 | Tennican et al. |
| 7,731,679 B2 | 6/2010 | Tennican et al. |
| 7,749,189 B2 | 7/2010 | Tennican et al. |
| 7,753,891 B2 | 7/2010 | Tennican et al. |
| 7,758,530 B2 | 7/2010 | DiFiore et al. |
| 7,758,566 B2 | 7/2010 | Simpson et al. |
| 7,762,524 B2 | 7/2010 | Cawthon et al. |
| 7,763,006 B2 | 7/2010 | Tennican |
| 7,766,182 B2 | 8/2010 | Trent et al. |
| 7,766,897 B2 | 8/2010 | Ramsey et al. |
| 7,776,011 B2 | 8/2010 | Tennican et al. |
| 7,780,794 B2 | 8/2010 | Rogers et al. |
| 7,785,616 B2 | 8/2010 | Stamler et al. |
| 7,794,675 B2 | 9/2010 | Lynn |
| 7,799,010 B2 | 9/2010 | Tennican |
| 7,803,139 B2 | 9/2010 | Fangrow, Jr. |
| 7,803,140 B2 | 9/2010 | Fangrow, Jr. |
| 7,815,614 B2 | 10/2010 | Fangrow, Jr. |
| 7,857,793 B2 | 12/2010 | Raulerson et al. |
| 7,922,701 B2 | 4/2011 | Buchman |
| 7,922,711 B2 | 4/2011 | Ranalletta et al. |
| 7,928,079 B2 | 4/2011 | Hrabie et al. |
| 7,938,795 B2 | 5/2011 | DiFiore et al. |
| 7,956,062 B2 | 6/2011 | Stamler et al. |
| 7,959,026 B2 | 6/2011 | Bertani |
| 7,963,565 B2 | 6/2011 | Suter |
| 7,972,137 B2 | 7/2011 | Rosen |
| 7,972,322 B2 | 7/2011 | Tennican |
| 7,981,090 B2 | 7/2011 | Plishka et al. |
| 7,985,302 B2 | 7/2011 | Rogers et al. |
| 7,993,309 B2 | 8/2011 | Schweikert |
| 7,998,134 B2 | 8/2011 | Fangrow et al. |
| 8,034,454 B2 | 10/2011 | Terry |
| 8,065,773 B2 | 11/2011 | Vaillancourt et al. |
| 8,066,670 B2 | 11/2011 | Cluff et al. |
| 8,069,523 B2 | 12/2011 | Vaillancourt et al. |
| 8,113,837 B2 | 2/2012 | Zegarelli |
| 8,146,757 B2 | 4/2012 | Abreu et al. |
| 8,162,899 B2 | 4/2012 | Tennican |
| 8,167,847 B2 | 5/2012 | Anderson et al. |
| 8,172,825 B2 | 5/2012 | Solomon et al. |
| 8,177,761 B2 | 5/2012 | Howlett et al. |

(56) References Cited

U.S. PATENT DOCUMENTS

| | | |
|---|---|---|
| 8,177,772 B2 | 5/2012 | Christensen et al. |
| 8,197,749 B2 | 6/2012 | Howlett et al. |
| 8,206,514 B2 | 6/2012 | Rogers et al. |
| 8,231,587 B2 | 7/2012 | Solomon et al. |
| 8,231,602 B2 | 7/2012 | Anderson et al. |
| 8,252,247 B2 | 8/2012 | Ferlic |
| 8,262,628 B2 | 9/2012 | Fangrow, Jr. |
| 8,262,643 B2 | 9/2012 | Tennican |
| 8,273,303 B2 | 9/2012 | Ferlic et al. |
| 8,281,824 B2 | 10/2012 | Molema et al. |
| 8,328,767 B2 | 12/2012 | Solomon et al. |
| 8,336,152 B2 | 12/2012 | Kerr et al. |
| 8,343,112 B2 | 1/2013 | Solomon et al. |
| 8,361,408 B2 | 1/2013 | Lynn |
| 8,372,045 B2 | 2/2013 | Needle et al. |
| 8,377,040 B2 | 2/2013 | Burkholz et al. |
| 8,414,547 B2 | 4/2013 | DiFiore et al. |
| 8,419,713 B1 | 4/2013 | Solomon et al. |
| 8,454,579 B2 | 6/2013 | Fang, Jr. |
| 8,480,968 B2 | 7/2013 | Lynn |
| 8,491,546 B2 | 7/2013 | Hoang et al. |
| 8,500,717 B2 | 8/2013 | Becker |
| 8,506,527 B2 | 8/2013 | Carlyon |
| 8,506,538 B2 | 8/2013 | Chelak |
| 8,523,798 B2 | 9/2013 | DiFiore |
| 8,523,830 B2 | 9/2013 | Solomon et al. |
| 8,523,831 B2 | 9/2013 | Solomon et al. |
| 8,533,887 B2 | 9/2013 | Hirst |
| 8,545,479 B2 | 10/2013 | Kitani et al. |
| 8,568,371 B2 | 10/2013 | Siopes et al. |
| 8,622,995 B2 | 1/2014 | Ziebol et al. |
| 8,622,996 B2 | 1/2014 | Ziebol et al. |
| 8,641,681 B2 | 2/2014 | Solomon et al. |
| 8,641,684 B2 | 2/2014 | Utterberg et al. |
| 8,647,308 B2 | 2/2014 | Solomon et al. |
| 8,647,326 B2 | 2/2014 | Solomon et al. |
| 8,651,271 B1 | 2/2014 | Shen |
| 8,671,496 B2 | 3/2014 | Kerr et al. |
| 8,740,864 B2 | 6/2014 | Hoang et al. |
| 8,758,307 B2 | 6/2014 | Grimm et al. |
| 8,777,504 B2 | 7/2014 | Shaw et al. |
| 8,791,073 B2 | 7/2014 | West et al. |
| 8,845,593 B2 | 9/2014 | Anderson et al. |
| 8,877,231 B2 | 11/2014 | Rosen |
| 8,910,919 B2 | 12/2014 | Bonnal et al. |
| 8,920,404 B2 | 12/2014 | DiFiore et al. |
| 8,968,268 B2 | 3/2015 | Anderson et al. |
| 8,981,139 B2 | 3/2015 | Schoenfisch et al. |
| 8,999,073 B2 | 4/2015 | Rogers et al. |
| 9,022,984 B2 | 5/2015 | Ziebol et al. |
| 9,072,296 B2 | 7/2015 | Mills et al. |
| 9,072,868 B2 | 7/2015 | Ziebol et al. |
| 9,078,992 B2 | 7/2015 | Ziebol et al. |
| 9,089,680 B2 | 7/2015 | Ueda et al. |
| 9,095,500 B2 | 8/2015 | Brandenburger et al. |
| 9,095,667 B2 | 8/2015 | Von Schuckmann |
| 9,101,685 B2 | 8/2015 | Li et al. |
| 9,101,750 B2 | 8/2015 | Solomon et al. |
| 9,114,915 B2 | 8/2015 | Solomon et al. |
| 9,125,600 B2 | 9/2015 | Steube et al. |
| 9,149,624 B2 | 10/2015 | Lewis |
| 9,180,252 B2 | 11/2015 | Gelblum et al. |
| 9,192,449 B2 | 11/2015 | Kerr et al. |
| 9,205,248 B2 | 12/2015 | Wu et al. |
| 9,216,440 B2 | 12/2015 | Ma et al. |
| 9,233,208 B2 | 1/2016 | Tekeste |
| 9,242,084 B2 | 1/2016 | Solomon et al. |
| 9,248,093 B2 | 2/2016 | Kelley, III et al. |
| 9,248,229 B2 | 2/2016 | Devouassoux et al. |
| 9,259,284 B2 | 2/2016 | Rogers et al. |
| 9,259,535 B2 | 2/2016 | Anderson et al. |
| 9,283,367 B2 | 3/2016 | Hoang et al. |
| 9,283,368 B2 | 3/2016 | Hoang et al. |
| 9,283,369 B2 | 3/2016 | Ma et al. |
| 9,289,588 B2 | 3/2016 | Chen |
| 9,296,525 B2 | 3/2016 | Murphy et al. |
| 9,302,049 B2 | 4/2016 | Tekeste |
| 9,320,858 B2 | 4/2016 | Grimm et al. |
| 9,320,859 B2 | 4/2016 | Grimm et al. |
| 9,320,860 B2 | 4/2016 | Grimm et al. |
| 9,352,080 B2 | 5/2016 | Goodall et al. |
| 9,352,140 B2 | 5/2016 | Kerr et al. |
| 9,352,141 B2 | 5/2016 | Wong |
| 9,352,142 B2 | 5/2016 | Ziebol et al. |
| 9,381,339 B2 | 7/2016 | Wu et al. |
| 9,399,125 B2 | 7/2016 | Burkholz |
| 9,408,971 B2 | 8/2016 | Carlyon |
| 9,527,660 B2 | 12/2016 | Tennican |
| 9,592,375 B2 | 3/2017 | Tennican |
| 9,700,676 B2 | 7/2017 | Anderson et al. |
| 9,700,677 B2 | 7/2017 | Anderson et al. |
| 9,700,710 B2 | 7/2017 | Anderson et al. |
| 9,707,348 B2 | 7/2017 | Anderson et al. |
| 9,707,349 B2 | 7/2017 | Anderson et al. |
| 9,707,350 B2 | 7/2017 | Anderson et al. |
| 9,809,355 B2 | 11/2017 | Solomon et al. |
| 9,849,276 B2 | 12/2017 | Ziebol et al. |
| 9,867,975 B2 | 1/2018 | Gardner et al. |
| 9,907,617 B2 | 3/2018 | Rogers |
| 9,933,094 B2 | 4/2018 | Fangrow |
| 9,999,471 B2 | 6/2018 | Rogers et al. |
| 10,016,587 B2 | 7/2018 | Gardner et al. |
| 10,046,156 B2 | 8/2018 | Gardner |
| 10,159,829 B2 | 12/2018 | Ziebol et al. |
| 10,166,381 B2 | 1/2019 | Gardner et al. |
| 10,195,000 B2 | 2/2019 | Rogers et al. |
| 10,201,692 B2 | 2/2019 | Chang |
| 10,328,207 B2 | 6/2019 | Anderson et al. |
| 10,525,250 B1 | 1/2020 | Ziebol et al. |
| 10,695,550 B2 | 6/2020 | Gardner et al. |
| 10,744,316 B2 | 8/2020 | Fangrow |
| 10,806,919 B2 | 10/2020 | Gardner et al. |
| 10,821,278 B2 | 11/2020 | Gardner et al. |
| 11,160,932 B2 | 11/2021 | Anderson et al. |
| 11,229,746 B2 | 1/2022 | Anderson et al. |
| 2002/0077693 A1 | 6/2002 | Barclay et al. |
| 2002/0082682 A1 | 6/2002 | Barclay et al. |
| 2002/0098278 A1 | 6/2002 | Bates et al. |
| 2003/0039697 A1 | 2/2003 | Zhao et al. |
| 2003/0062376 A1 | 4/2003 | Sears et al. |
| 2003/0072783 A1 | 4/2003 | Stamler et al. |
| 2003/0153865 A1 | 8/2003 | Connell et al. |
| 2003/0199835 A1 | 10/2003 | Leinsing et al. |
| 2003/0208165 A1 | 11/2003 | Christensen et al. |
| 2004/0034042 A1 | 2/2004 | Tsuji et al. |
| 2004/0034329 A1 | 2/2004 | Mankus et al. |
| 2004/0037836 A1 | 2/2004 | Stamler et al. |
| 2004/0048542 A1 | 3/2004 | Thomascheisky et al. |
| 2004/0052689 A1 | 3/2004 | Yao |
| 2004/0052831 A1 | 3/2004 | Modak et al. |
| 2004/0156908 A1 | 8/2004 | Polaschegg et al. |
| 2004/0210201 A1 | 10/2004 | Farnan |
| 2004/0215148 A1 | 10/2004 | Hwang et al. |
| 2004/0247640 A1 | 12/2004 | Zhao et al. |
| 2004/0249337 A1 | 12/2004 | DiFiore |
| 2004/0249338 A1 | 12/2004 | DeCant, Jr. et al. |
| 2005/0013836 A1 | 1/2005 | Raad |
| 2005/0015075 A1 | 1/2005 | Wright et al. |
| 2005/0065479 A1 | 3/2005 | Schiller et al. |
| 2005/0098527 A1 | 5/2005 | Yates et al. |
| 2005/0124942 A1 | 6/2005 | Richmond |
| 2005/0124970 A1 | 6/2005 | Kunin et al. |
| 2005/0147524 A1 | 7/2005 | Bousquet |
| 2005/0147525 A1 | 7/2005 | Bousquet |
| 2005/0148930 A1 | 7/2005 | Hseih et al. |
| 2005/0152891 A1 | 7/2005 | Toone et al. |
| 2005/0171493 A1 | 8/2005 | Nicholls |
| 2005/0214185 A1 | 9/2005 | Castaneda |
| 2005/0220882 A1 | 10/2005 | Pritchard et al. |
| 2005/0228362 A1 | 10/2005 | Vaillancourt |
| 2005/0228482 A1 | 10/2005 | Herzog et al. |
| 2005/0256461 A1 | 11/2005 | DiFiore et al. |
| 2005/0265958 A1 | 12/2005 | West et al. |
| 2005/0267421 A1 | 12/2005 | Wing |

(56) References Cited

U.S. PATENT DOCUMENTS

| | | |
|---|---|---|
| 2005/0271711 A1 | 12/2005 | Lynch et al. |
| 2005/0288551 A1 | 12/2005 | Callister et al. |
| 2006/0004316 A1 | 1/2006 | DiFiore et al. |
| 2006/0024372 A1 | 2/2006 | Utterberg et al. |
| 2006/0058734 A1 | 3/2006 | Phillips |
| 2006/0096348 A1 | 5/2006 | DiFiore |
| 2006/0118122 A1 | 6/2006 | Martens et al. |
| 2006/0129109 A1 | 6/2006 | Shaw et al. |
| 2006/0142730 A1 | 6/2006 | Proulx et al. |
| 2006/0149191 A1 | 7/2006 | DiFiore |
| 2006/0161115 A1 | 7/2006 | Fangrow |
| 2006/0195117 A1 | 8/2006 | Rucker et al. |
| 2006/0202146 A1 | 9/2006 | Doyle |
| 2006/0206178 A1 | 9/2006 | Kim |
| 2006/0253084 A1 | 11/2006 | Nordgren |
| 2006/0261076 A1 | 11/2006 | Anderson |
| 2007/0003603 A1 | 1/2007 | Karandikar et al. |
| 2007/0088292 A1 | 4/2007 | Fangrow |
| 2007/0088293 A1 | 4/2007 | Fangrow |
| 2007/0088294 A1 | 4/2007 | Fangrow |
| 2007/0106205 A1 | 5/2007 | Connell et al. |
| 2007/0167910 A1 | 7/2007 | Tennican et al. |
| 2007/0179453 A1 | 8/2007 | Lim et al. |
| 2007/0187353 A1 | 8/2007 | Fox et al. |
| 2007/0212381 A1 | 9/2007 | DiFiore et al. |
| 2007/0231315 A1 | 10/2007 | Lichte et al. |
| 2007/0248676 A1 | 10/2007 | Stamler et al. |
| 2007/0249996 A1 | 10/2007 | Tennican et al. |
| 2007/0265578 A1 | 11/2007 | Tennican et al. |
| 2007/0287989 A1 | 12/2007 | Crawford et al. |
| 2008/0027399 A1 | 1/2008 | Harding et al. |
| 2008/0027401 A1 | 1/2008 | Ou-Yang |
| 2008/0033371 A1 | 2/2008 | Updegraff et al. |
| 2008/0039803 A1 | 2/2008 | Lynn |
| 2008/0058733 A1 | 3/2008 | Vogt et al. |
| 2008/0093245 A1 | 4/2008 | Periasamy et al. |
| 2008/0095680 A1 | 4/2008 | Steffens et al. |
| 2008/0097315 A1 | 4/2008 | Miner et al. |
| 2008/0097407 A1 | 4/2008 | Plishka |
| 2008/0103485 A1 | 5/2008 | Kruger |
| 2008/0287920 A1 | 5/2008 | Fangrow et al. |
| 2008/0014005 A1 | 6/2008 | Shirley |
| 2008/0128646 A1 | 6/2008 | Clawson |
| 2008/0147047 A1 | 6/2008 | Davis et al. |
| 2008/0161763 A1 | 7/2008 | Harding et al. |
| 2008/0172007 A1 | 7/2008 | Bousquet |
| 2008/0177250 A1 | 7/2008 | Howlett et al. |
| 2008/0187460 A1 | 8/2008 | Utterberg et al. |
| 2008/0188791 A1 | 8/2008 | DiFiore et al. |
| 2008/0190485 A1 | 8/2008 | Guala |
| 2008/0262465 A1 | 10/2008 | Zinger et al. |
| 2008/0318333 A1 | 12/2008 | Nielsen et al. |
| 2008/0319423 A1 | 12/2008 | Tanghoj et al. |
| 2009/0008393 A1 | 1/2009 | Howlett et al. |
| 2009/0012426 A1 | 1/2009 | Tennican |
| 2009/0024096 A1 | 1/2009 | Hai et al. |
| 2009/0028750 A1 | 1/2009 | Ryan |
| 2009/0062766 A1 | 3/2009 | Howlett et al. |
| 2009/0093757 A1 | 4/2009 | Tennican |
| 2009/0126867 A1 | 5/2009 | Decant, Jr. et al. |
| 2009/0137969 A1 | 5/2009 | Colantonio et al. |
| 2009/0149820 A1 | 6/2009 | DiFiore |
| 2009/0163876 A1 | 6/2009 | Chebator et al. |
| 2009/0205151 A1 | 8/2009 | Fisher et al. |
| 2009/0205656 A1 | 8/2009 | Nishibayashi et al. |
| 2009/0247485 A1 | 10/2009 | Ahmed et al. |
| 2009/0259194 A1 | 10/2009 | Pinedjian et al. |
| 2009/0270832 A1 | 10/2009 | Vancaillie et al. |
| 2009/0293882 A1 | 12/2009 | Terry |
| 2010/0004510 A1 | 1/2010 | Kuroshima |
| 2010/0047123 A1 | 2/2010 | Solomon et al. |
| 2010/0049170 A1 | 2/2010 | Solomon et al. |
| 2010/0050351 A1 | 3/2010 | Colantonio et al. |
| 2010/0064456 A1 | 3/2010 | Ferlic |
| 2010/0074932 A1 | 3/2010 | Talsma |
| 2010/0106102 A1 | 4/2010 | Ziebol et al. |
| 2010/0106103 A1 | 4/2010 | Ziebol et al. |
| 2010/0137472 A1 | 6/2010 | Ou-Yang |
| 2010/0143427 A1 | 6/2010 | King et al. |
| 2010/0152670 A1 | 6/2010 | Low |
| 2010/0160894 A1 | 6/2010 | Julian et al. |
| 2010/0172794 A1 | 7/2010 | Ferlic et al. |
| 2010/0242993 A1 | 9/2010 | Hoang et al. |
| 2010/0253070 A1 | 10/2010 | Cheon et al. |
| 2010/0280805 A1 | 11/2010 | DiFiore |
| 2010/0292673 A1 | 11/2010 | Korogi et al. |
| 2010/0292674 A1 | 11/2010 | Jepson et al. |
| 2010/0306938 A1 | 12/2010 | Rogers et al. |
| 2010/0318040 A1 | 12/2010 | Kelley, III et al. |
| 2011/0030726 A1 | 2/2011 | Vaillancourt et al. |
| 2011/0044850 A1 | 2/2011 | Solomon et al. |
| 2011/0046564 A1 | 2/2011 | Zhong |
| 2011/0046603 A1 | 2/2011 | Felsovalyi et al. |
| 2011/0062703 A1 | 3/2011 | Lopez |
| 2011/0064512 A1 | 3/2011 | Shaw et al. |
| 2011/0071475 A1 | 3/2011 | Horvath et al. |
| 2011/0082431 A1 | 4/2011 | Burgess et al. |
| 2011/0184338 A1 | 7/2011 | McKay |
| 2011/0184382 A1 | 7/2011 | Cady |
| 2011/0208128 A1 | 8/2011 | Wu et al. |
| 2011/0217212 A1 | 9/2011 | Solomon et al. |
| 2011/0276031 A1 | 11/2011 | Hoang et al. |
| 2011/0282302 A1 | 11/2011 | Lopez et al. |
| 2011/0311602 A1 | 12/2011 | Mills et al. |
| 2011/0314619 A1 | 12/2011 | Schweikert |
| 2012/0022469 A1 | 1/2012 | Albert et al. |
| 2012/0031904 A1 | 2/2012 | Kuhn et al. |
| 2012/0039764 A1 | 2/2012 | Solomon et al. |
| 2012/0083730 A1 | 4/2012 | Rush et al. |
| 2012/0083750 A1 | 4/2012 | Sansoucy |
| 2012/0157965 A1 | 6/2012 | Wotton et al. |
| 2012/0191029 A1 | 7/2012 | Hopf et al. |
| 2012/0195807 A1 | 8/2012 | Ferlic |
| 2012/0216359 A1 | 8/2012 | Rogers et al. |
| 2012/0216360 A1 | 8/2012 | Rogers et al. |
| 2012/0220955 A1 | 8/2012 | Maseda et al. |
| 2012/0283696 A1 | 11/2012 | Cronenberg et al. |
| 2012/0302968 A1 | 11/2012 | Tennican |
| 2012/0302970 A1 | 11/2012 | Tennican |
| 2012/0302997 A1 | 11/2012 | Gardner et al. |
| 2012/0315201 A1 | 12/2012 | Ferlic et al. |
| 2013/0030414 A1* | 1/2013 | Gardner ............... A61M 39/20 604/533 |
| 2013/0035667 A1 | 2/2013 | Anderson et al. |
| 2013/0039953 A1 | 2/2013 | Dudnyk et al. |
| 2013/0053751 A1 | 2/2013 | Holtham |
| 2013/0072908 A1 | 3/2013 | Solomon et al. |
| 2013/0085313 A1 | 4/2013 | Fowler et al. |
| 2013/0085474 A1 | 4/2013 | Charles et al. |
| 2013/0098398 A1 | 4/2013 | Kerr et al. |
| 2013/0098938 A1 | 4/2013 | Efthimiadis |
| 2013/0102950 A1 | 4/2013 | DiFiore |
| 2013/0123754 A1 | 5/2013 | Solomon et al. |
| 2013/0134161 A1 | 5/2013 | Fogel et al. |
| 2013/0138085 A1 | 5/2013 | Tennican |
| 2013/0144258 A1 | 6/2013 | Ziebol et al. |
| 2013/0150795 A1 | 6/2013 | Snow |
| 2013/0164189 A1 | 6/2013 | Hadden |
| 2013/0171030 A1 | 7/2013 | Ferlic et al. |
| 2013/0183635 A1 | 7/2013 | Wilhoit |
| 2013/0184679 A1 | 7/2013 | Ziebol et al. |
| 2013/0197485 A1 | 8/2013 | Gardner et al. |
| 2013/0204231 A1 | 8/2013 | Ziebol et al. |
| 2013/0274686 A1 | 10/2013 | Ziebol et al. |
| 2014/0042116 A1 | 2/2014 | Shen et al. |
| 2014/0048079 A1 | 2/2014 | Gardner et al. |
| 2014/0052074 A1 | 2/2014 | Tekeste |
| 2014/0101876 A1 | 4/2014 | Rogers et al. |
| 2014/0155868 A1 | 6/2014 | Nelson et al. |
| 2014/0227144 A1 | 8/2014 | Liu et al. |
| 2014/0228775 A1 | 8/2014 | Burkholz et al. |
| 2014/0228809 A1 | 8/2014 | Wong |
| 2014/0243797 A1 | 8/2014 | Jensen et al. |
| 2014/0249476 A1 | 9/2014 | Grimm et al. |

(56) References Cited

U.S. PATENT DOCUMENTS

| | | |
|---|---|---|
| 2014/0249477 A1 | 9/2014 | Grimm et al. |
| 2014/0249486 A1 | 9/2014 | Grimm et al. |
| 2014/0339812 A1 | 11/2014 | Carney et al. |
| 2014/0339813 A1 | 11/2014 | Cederschiöld et al. |
| 2015/0141934 A1 | 5/2015 | Gardner et al. |
| 2015/0148287 A1 | 5/2015 | Woo et al. |
| 2015/0165127 A1 | 6/2015 | Haefele et al. |
| 2015/0217106 A1 | 8/2015 | Banik et al. |
| 2015/0231380 A1 | 8/2015 | Hoang et al. |
| 2015/0237854 A1 | 8/2015 | Mills et al. |
| 2015/0238703 A1 | 8/2015 | Glocker |
| 2015/0258324 A1 | 9/2015 | Chida et al. |
| 2015/0273199 A1 | 10/2015 | Adams et al. |
| 2015/0297455 A1 | 10/2015 | Sanders et al. |
| 2015/0297881 A1 | 10/2015 | Sanders et al. |
| 2015/0306367 A1 | 10/2015 | DiFiore |
| 2015/0306369 A1 | 10/2015 | Burkholz et al. |
| 2015/0314119 A1 | 11/2015 | Anderson et al. |
| 2015/0320926 A1 | 11/2015 | Fitzpatrick et al. |
| 2015/0320992 A1 | 11/2015 | Bonnet et al. |
| 2015/0343174 A1 | 12/2015 | Ziebol et al. |
| 2015/0374968 A1 | 12/2015 | Solomon et al. |
| 2016/0001056 A1 | 1/2016 | Nelson et al. |
| 2016/0001058 A1 | 1/2016 | Ziebol et al. |
| 2016/0015863 A1 | 1/2016 | Gupta et al. |
| 2016/0015931 A1 | 1/2016 | Ryan et al. |
| 2016/0015959 A1 | 1/2016 | Solomon et al. |
| 2016/0045629 A1 | 2/2016 | Gardner et al. |
| 2016/0067365 A1 | 3/2016 | Ma et al. |
| 2016/0067471 A1 | 3/2016 | Ingram et al. |
| 2016/0088995 A1 | 3/2016 | Ueda et al. |
| 2016/0089530 A1 | 3/2016 | Sathe |
| 2016/0101223 A1 | 4/2016 | Kelley, III et al. |
| 2016/0101276 A1 | 4/2016 | Tekeste |
| 2016/0106969 A1 | 4/2016 | Neftel |
| 2016/0121097 A1 | 5/2016 | Steele |
| 2016/0144118 A1 | 5/2016 | Solomon et al. |
| 2016/0158520 A1 | 6/2016 | Ma et al. |
| 2016/0158521 A1 | 6/2016 | Hoang et al. |
| 2016/0158522 A1 | 6/2016 | Hoang et al. |
| 2016/0184527 A1 | 6/2016 | Tekeste |
| 2016/0213912 A1 | 7/2016 | Daneluzzi |
| 2016/0250420 A1 | 9/2016 | Maritan et al. |
| 2016/0354596 A1 | 12/2016 | DiFiore |
| 2017/0020911 A1 | 1/2017 | Berry et al. |
| 2017/0042636 A1 | 2/2017 | Young |
| 2017/0143447 A1 | 5/2017 | Rogers et al. |
| 2017/0182241 A1 | 6/2017 | DiFiore |
| 2017/0203092 A1 | 7/2017 | Ryan et al. |
| 2017/0239443 A1 | 8/2017 | Abitabilo et al. |
| 2017/0361023 A1 | 12/2017 | Anderson et al. |
| 2018/0028403 A1 | 2/2018 | Row |
| 2018/0200500 A1 | 7/2018 | Ziebol et al. |
| 2018/0214684 A1 | 8/2018 | Avula et al. |
| 2018/0369562 A1 | 12/2018 | Gardner |
| 2019/0038888 A1 | 2/2019 | Gardner |
| 2019/0111245 A1 | 4/2019 | Gardner |
| 2019/0201681 A1 | 7/2019 | Ziebol et al. |
| 2019/0282795 A1 | 9/2019 | Fangrow |
| 2020/0069931 A1 | 3/2020 | Fangrow |
| 2020/0085690 A1 | 3/2020 | Fangrow |
| 2020/0121858 A1 | 4/2020 | Anderson |
| 2020/0139101 A1 | 5/2020 | Ziebol et al. |
| 2020/0139102 A1 | 5/2020 | Ziebol et al. |
| 2020/0139103 A1 | 5/2020 | Ziebol et al. |
| 2020/0139104 A1 | 5/2020 | Ziebol et al. |
| 2020/0155794 A1 | 5/2020 | Ziebol |
| 2020/0139037 A1 | 8/2020 | Ziebol et al. |
| 2020/0324102 A1 | 10/2020 | Row |
| 2020/0406020 A1 | 12/2020 | Row |
| 2021/0093791 A1 | 4/2021 | Anderson |
| 2021/0162194 A1 | 6/2021 | Gardner |
| 2021/0205596 A1 | 7/2021 | Ziebol et al. |
| 2021/0308442 A1 | 10/2021 | Gardner |

FOREIGN PATENT DOCUMENTS

| | | |
|---|---|---|
| CA | 2 841 832 | 6/2019 |
| CN | 2402327 Y | 10/2000 |
| CN | 2815392 Y | 9/2006 |
| CN | 201150420 Y | 11/2008 |
| CN | 201519335 U | 7/2010 |
| CN | 106902402 | 6/2017 |
| DE | 3515665 | 5/1986 |
| DE | 89 06 628 U1 | 9/1989 |
| DE | 43 34 272 | 4/1995 |
| DE | 29617133 | 1/1997 |
| EP | 0 088 341 | 9/1983 |
| EP | 0 108 785 | 5/1984 |
| EP | 0 174 162 | 3/1986 |
| EP | 0 227 219 | 7/1987 |
| EP | 0 237 239 | 9/1987 |
| EP | 0 245 872 | 11/1987 |
| EP | 0 257 485 | 3/1988 |
| EP | 0 639 385 | 2/1995 |
| EP | 0 734 721 | 10/1996 |
| EP | 0 769 265 | 4/1997 |
| EP | 1 061 000 | 10/2000 |
| EP | 1 331 020 | 7/2003 |
| EP | 1 471 011 | 10/2004 |
| EP | 1 442 753 | 2/2007 |
| EP | 1 813 293 | 8/2007 |
| EP | 1 977 714 | 10/2008 |
| EP | 2 444117 | 4/2012 |
| EP | 2 606 930 | 6/2013 |
| EP | 2 671 604 | 12/2013 |
| EP | 2 731 658 | 5/2014 |
| FR | 2 493 149 A | 5/1982 |
| FR | 2 506 162 | 11/1982 |
| FR | 2 782 910 | 3/2000 |
| GB | 123221 | 2/1919 |
| GB | 2 296 182 | 6/1996 |
| GB | 2 333 097 | 7/1999 |
| GB | 2 387 772 | 10/2003 |
| JP | 57-131462 U | 8/1982 |
| JP | 04-99950 | 2/1992 |
| JP | 09-216661 A | 8/1997 |
| JP | 2000-157630 A | 6/2000 |
| JP | 2002-234567 A | 8/2002 |
| JP | 2002-291906 | 10/2002 |
| JP | 2005-218649 | 8/2005 |
| JP | 2006-182663 A | 7/2006 |
| JP | 2011-036691 | 2/2011 |
| JP | 2011-528647 | 11/2011 |
| JP | 2013-520287 | 6/2013 |
| JP | 2014-117461 | 6/2014 |
| RU | 2 246 321 C1 | 2/2005 |
| WO | WO 1983/03975 | 11/1983 |
| WO | WO 1985/05040 | 11/1985 |
| WO | WO 93/20806 | 10/1993 |
| WO | WO 95/07691 | 3/1995 |
| WO | WO 96/35416 | 11/1996 |
| WO | WO 96/38136 | 12/1996 |
| WO | WO 1997/19701 | 6/1997 |
| WO | WO 1998/12125 | 3/1998 |
| WO | WO 1999/44665 | 9/1999 |
| WO | WO 2001/70199 A1 | 9/2001 |
| WO | WO 2002/05188 | 1/2002 |
| WO | WO 2002/47581 | 6/2002 |
| WO | WO 2002/49544 | 6/2002 |
| WO | WO 2003/015677 | 2/2003 |
| WO | WO 2003/070296 | 8/2003 |
| WO | WO 2004/035129 | 4/2004 |
| WO | WO 2004/112846 | 12/2004 |
| WO | WO 2005/112954 A1 | 12/2005 |
| WO | WO 2005/112974 A2 | 12/2005 |
| WO | WO 2006/007690 | 1/2006 |
| WO | WO 2006/044236 | 4/2006 |
| WO | WO 2006/102756 | 10/2006 |
| WO | WO 2007/008511 | 1/2007 |
| WO | WO 2007/056773 | 5/2007 |
| WO | WO 2007/137056 | 11/2007 |
| WO | WO 2008/042285 | 4/2008 |
| WO | WO 2008/086631 | 7/2008 |

(56) References Cited

FOREIGN PATENT DOCUMENTS

| WO | WO 2008/089196 | 7/2008 |
|---|---|---|
| WO | WO 2008/100950 | 8/2008 |
| WO | WO 2008/140807 | 11/2008 |
| WO | WO 2009/002474 | 12/2008 |
| WO | WO 2009/060322 | 5/2009 |
| WO | WO 2009/117135 | 9/2009 |
| WO | WO 2009/123709 | 10/2009 |
| WO | WO 2009/136957 | 11/2009 |
| WO | WO 2009/153224 | 12/2009 |
| WO | WO 2010/002757 | 1/2010 |
| WO | WO 2010/002808 | 1/2010 |
| WO | WO 2010/011616 | 1/2010 |
| WO | WO 2010/034470 | 4/2010 |
| WO | WO 2010/039171 | 4/2010 |
| WO | WO 2010/062589 | 6/2010 |
| WO | WO 2011/028722 | 3/2011 |
| WO | WO 2011/053924 | 5/2011 |
| WO | WO 2011/106374 | 9/2011 |
| WO | WO 2011/119021 | 9/2011 |
| WO | WO 2012/118829 | 9/2012 |
| WO | WO 2012/162006 | 11/2012 |
| WO | WO 2013/009998 | 1/2013 |
| WO | WO 2013/023146 | 2/2013 |
| WO | WO 2012/184716 | 12/2013 |
| WO | WO 2013/192574 | 12/2013 |
| WO | WO 2014/074929 | 5/2014 |
| WO | WO 2014/140949 | 9/2014 |
| WO | WO 2014/159346 | 10/2014 |
| WO | WO 2015/119940 | 8/2015 |
| WO | WO 2015/164129 | 10/2015 |
| WO | WO 2015/174953 | 11/2015 |
| WO | WO 2016/182822 | 11/2016 |
| WO | WO 2017/015047 | 1/2017 |
| WO | WO 2017/127364 | 7/2017 |
| WO | WO 2017/127365 | 7/2017 |
| WO | WO 2018/009653 | 1/2018 |
| WO | WO 2018/071717 | 4/2018 |
| WO | WO 2018/204206 | 11/2018 |
| WO | WO 2018/237090 | 12/2018 |
| WO | WO 2018/237122 | 12/2018 |
| WO | WO 2019/178560 | 9/2019 |
| WO | WO 2019/246472 | 12/2019 |
| WO | WO 2020/097366 | 5/2020 |
| WO | WO 2020/251947 | 12/2020 |

OTHER PUBLICATIONS

Clave® Needlefree Connector, icumedial, human connections, 2 page brochure. 2012, M1-1065 Rev. 04.
Du. Y, et al. Protein adsorption on polyurethane catheters modified with a novel antithrombin-heparin covalent complex, Journal of Biomedical Materials Research Part A, 2006, 216-225.
Holmer, E. et al. The molecular-weight dependence of the rate-enhancing effect of heparin on the inhibition of thrombin, Factor Xa, Factor IXa, Factor Xia, Factor XIIa and kallikrein by antithrombin, Biochem. J. (1981) 193, 395-400.
ICU Medical Antimicrobial Microclave, first sold Jan. 21, 2010, p. 1-2.
Klement, P. et al. Chronic performance of polyurethane catheters covalently coated with ATH complex: A rabbit jugular vein model, Biomaterials, (2006), 27, 5107-5117.
Otto, Mosby's Pocket Guide to Infusion Therapy. Elsevier Health Sciences, 2004. pp. 65-66. Accessed at: http://books.google.com/books?id=j8T14HwWdS4C&Ipg=PP1&pg=PP1#v=onepage&f=false (Year: 2004).
Quinton Beta Capp II advertisement, in 3 pages.
Small-bore connectors for liquids and gases in healthcare applications—Part 7: Connectors for intravascular or hypodermic applications, ISO 80369-7, Corrected version dated Dec. 1, 2016 (50 pages).
V-Link Lu er Activated Device, with VitalShield Protective Coating, 2 page brochure, Baxter Dec. 2009.
Baxter Minicap: Photographs of the Baxter Minicap (Sep. 1, 1998) (4 pages).
Baxter, "Peritoneal Dialysis Patient Connectology," Product Descriptions in 1 page, downloaded Jul. 1, 2011.
Catheter Connections, "Introducing DualCap," Product Brochure in 1 page, Copyright 2011.
Charney, "Baxter Healthcare InterlinkTM IV Access System" in 1 page, from Handbook of Modern Hospital Safety. Published Mar. 1999.
Conical Fittings: International Standard, "Conical fittings with 6% (Luer) Taper for Syringes, Needles and certain Other Medical Equipment—Part 2: Lock Fittings", Ref. No. ISO 594-2:1998. International Organization for Standardization (Sept. 1, 1998) 2nd ed. (16 pages).
Devine, redacted version of letter from David A. Divine, Esq. of Lee & Hayes, dated May 16, 2011 (3 pages).
Devine, redacted version of letter from David A. Divine, Esq. of Lee & Hayes, dated May 27, 2011 (3 pages).
Hospira, "You Work in Neverland," Lifeshield Product Brochure in 2 pages, Published 2009.
Hyprotek, "Port Protek," Product Brochure in 1 page, downloaded Sep. 19, 2011 from http://www.hyprotek.com/products.html.
ICU Medical Inc., "Oncology System Solutions," Product Brochure in 17 pages, Copyright 2013.
ICU Medical Inc., "Protective Cap," Photographs of Spiros Protective Cap in 2 pages, Product available 2013.
International Search Report and Written Opinion re PCT/US2018/038625, dated Sep. 11, 2018 (12 pages).
International Search Report and Written Opinion, re PCT Application No. PCT/US17/56407, dated Dec. 11, 2017.
International Preliminary Report on Patentability, re PCT Application No. PCT/US17/56407, dated Apr. 16, 2019.
International Search Report and Written Opinion re PCT Application No. PCT/US19/22610, dated Jul. 22, 2019.
Menyhay et al., "Disinfection of Needleless Catheter Connectors and Access Ports with Alcohol May Not Prevent Microbial Entry: The Promise of a Novel Antiseptic-Barrier Cap" Infection Control Hospital and Epidemiology, vol. 27, No. 1 (Jan. 2006) (5 pages).
Photographs of the Baxter Minicap (Sep. 1, 1998) (4 pages).
Beta Cap II Advertisement from Quinton Instrument Co. (Aug. 1981).
"Small-bore connectors for liquids and gases in healthcare applications—Part : Connectors for intravascular or hypodermic applications," ISO 80369-7, Corrected version dated Dec. 1, 2016 (50 pages).

* cited by examiner

SANITIZING CAPS FOR MEDICAL CONNECTORS

INCORPORATION BY REFERENCE

This application is a continuation of U.S. patent application Ser. No. 16/340,300, filed on Apr. 8, 2019, which is a U.S. national phase of PCT Application No. PCT/US2017/056407, filed on Oct. 12, 2017, which claims priority to U.S. Provisional Patent Application No. 62/408,546, filed on Oct. 14, 2016; U.S. Provisional Patent Application No. 62/420,359, filed on Nov. 10, 2016; U.S. Provisional Patent Application No. 62/490,952, filed on Apr. 27, 2017; U.S. Provisional Patent Application No. 62/526,847, filed on Jun. 29, 2017; U.S. Provisional Patent Application No. 62/527,897, filed on Jun. 30, 2017; and U.S. Provisional Patent Application No. 62/571,157, filed on Oct. 11, 2017, each of which are hereby incorporated by reference herein in their entireties, forming part of the present disclosure. Any feature, structure, material, method, or step that is described and/or illustrated in any embodiment in any of the foregoing provisional patent applications can be used with or instead of any feature, structure, material, method, or step that is described and/or illustrated in the following paragraphs of this specification or the accompanying drawings.

BACKGROUND

Field of the Invention

This invention relates to caps and, more particularly, to antiseptic caps for use with medical connectors.

Certain embodiments disclosed herein relate to caps for medical connectors and more specifically relate to caps that can be used to disinfect and prevent future contamination of unconnected medical connectors, such as connectors that may be used for fluid flow or for fluid-delivery systems.

Description of the Related Art

Catheters are widely used to treat patients requiring a variety of medical procedures. Catheters can either be acute, or temporary, for short-term use or chronic for long-term treatment. Catheters are commonly inserted into central veins (such as the vena cava) from peripheral vein sites to provide access to a patient's vascular system.

Catheter connections, such as, for example, connections of catheters to dialysis machine tubing, to IV line tubing, to infusion ports and to catheter caps, which are used to seal the end of a catheter to protect the sterility of the catheter and prevent fluid loss and/or particle contamination, are most often made utilizing the medical industry's standardized Luer taper fittings. These fittings, which may either be male couplings or female couplings, include a tapered end of standardized dimensions. Coupling is made by the press-fit of mating parts. A threaded lock-fit or other type of securing mechanism is commonly utilized to ensure the integrity of the pressure fit of the Luer fittings. There are also other non-standard fittings that can be used to selectively couple multiple components together.

Catheter-related bloodstream infections (CRBSI), such as may be caused by microorganisms that enter a patient's body via intravascular catheters, are a significant cause of unnecessary illness, complications, and excess medical costs. A substantial number of such infections occur in U.S. intensive care units annually.

Providing antimicrobial agents in catheters is one approach for reducing these infections. Many of such catheters, however, do not have satisfactory results. Additionally, some microbes have developed resistance to the various antimicrobial agents used in the catheters.

It has been found that the use of antiseptic caps, such as the cap manufactured and sold by *Excelsior* under the trademark SWABCAP, greatly reduce the incidence of infections, resulting in, among other things, significant health benefits for patients and vast cost savings. However, there remains a need for alternative cap designs for use with a variety of medical fittings or connectors.

SUMMARY OF THE INVENTION

Disclosed herein are disinfecting caps that can reduce the threat of microorganisms entering the bloodstream of a patient via fluid flow or fluid-delivery systems, such as, for example, medical connectors, needleless injection sites, and/or medical fluid transfer devices. In some embodiments, one or more caps can be configured for use with a medical infusion system with one or more luer connectors, such as a female or male medical connector having a luer fitting. In some embodiments, a cap has a base and a liquid-dispensing material, such as an absorbent material, that is configured to carry a therapeutic liquid or gel, such as a liquid or gel antiseptic or antimicrobial agent (e.g., isopropyl alcohol, or chlorhexidine gluconate, or metallic ions such as silver ions or copper ions, or any other suitable agent or agents for sanitizing or removing contaminants).

BRIEF DESCRIPTION OF THE DRAWINGS

Embodiments will now be described with reference to the following drawings, which are provided by way of example, and not limitation Like reference numerals indicate identical or functionally similar elements. The sizes and relative proportions of all components and features shown in the drawings form part of this disclosure but should not be interpreted to be part of a claim unless specifically included in such claim.

FIG. 8A is a front perspective view of an embodiment of an antiseptic cap.

FIG. 8B is a top view of the antiseptic cap of FIG. 8A.

DETAILED DESCRIPTION

Figure 1A:
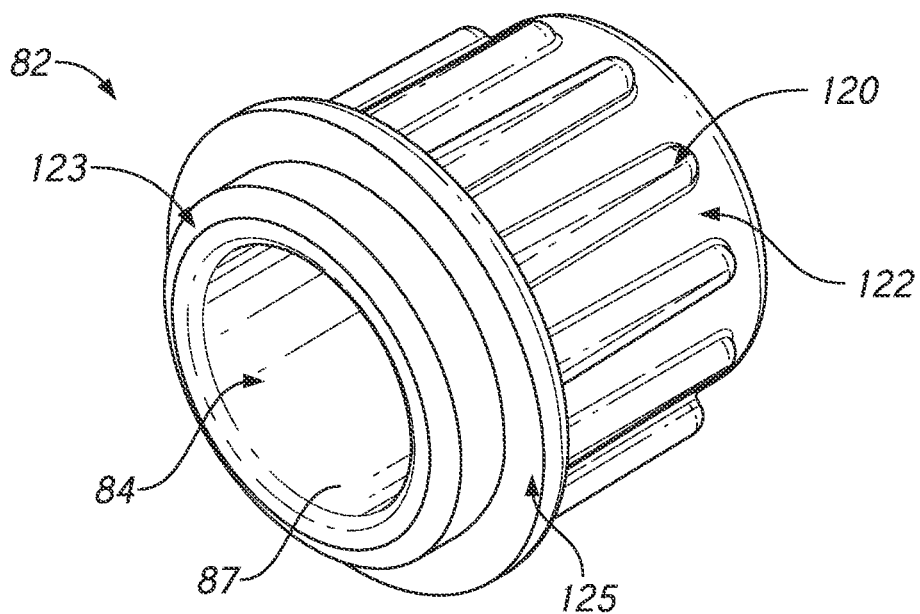
FIG. 1A is a front perspective view of an embodiment of an antiseptic cap.

Various systems, methods, and components can be used in different embodiments of medical caps. Some embodiments are illustrated in the accompanying figures; however, the figures are provided for convenience of illustration only, and should not be interpreted to limit the inventions to the particular combinations of features shown. Rather, any feature, structure, material, step, or component of any embodiment described and/or illustrated in this specification can be used by itself, or with or instead of any other feature, structure, material, step, or component of any other embodiment described and/or illustrated in this specification. Nothing in this specification is essential or indispensable. Any of the devices or connections or features that are described and/or illustrated anywhere in this specification can be configured to attach to or protect or sanitize luer connectors, which are in compliance with ISO standard 594 or ISO 80369, or can comply with any other industry standard that is applicable to medical fluid connectors.

Overview

This disclosure relates to embodiments of a sanitizing cap that can be used to disinfect and/or protect medical connectors. A cap may be used with intravascular connectors associated with a fluid pathway, such as an IV line. All references to any type of connector (e.g., a male luer connector) in this application should be understood to include and disclose any type of medical implement that accomplishes or facilitates storage or transfer of medical fluid or connection of medical fluid lines (e.g., any open or resealable fluid line connector, syringe, catheter connector, vial, vial adapter, pump cartridge or disposable, pharmaceutical compounding component, female connector, blood-line connector, IV bag, catheter inserter, venting or priming cap, etc.).

Fluid pathways, once established, may provide direct access to a patient's blood stream and can be used intermittently to administer medications to a patient. These fluid pathways can have one or more associated medical connectors that can be connected to other medical connectors. In some embodiments, a plurality of corresponding connectors can have male or female connection regions, such as male or female luer connection regions or luer locks. The connection regions can provide a convenient way to connect and disconnect the fluid pathway at various times. When connectors with connection regions are disconnected, one or more caps (e.g., luer caps) can protect the unconnected connectors from possible contamination. It can be advantageous for the caps to carry or contain some form of an antiseptic for disinfecting a connection region (e.g., a luer connection region) before sealing the connector off from possible future contamination from the outside. Any structure, step, material, or component that is illustrated and/or described in any embodiment in this specification can be used with or instead of any other structure, step, material, or component that is illustrated and/or described in any other embodiment in this specification. No structure, step, material, or component is essential or indispensable.

Antiseptic Cap

Figure 1B:
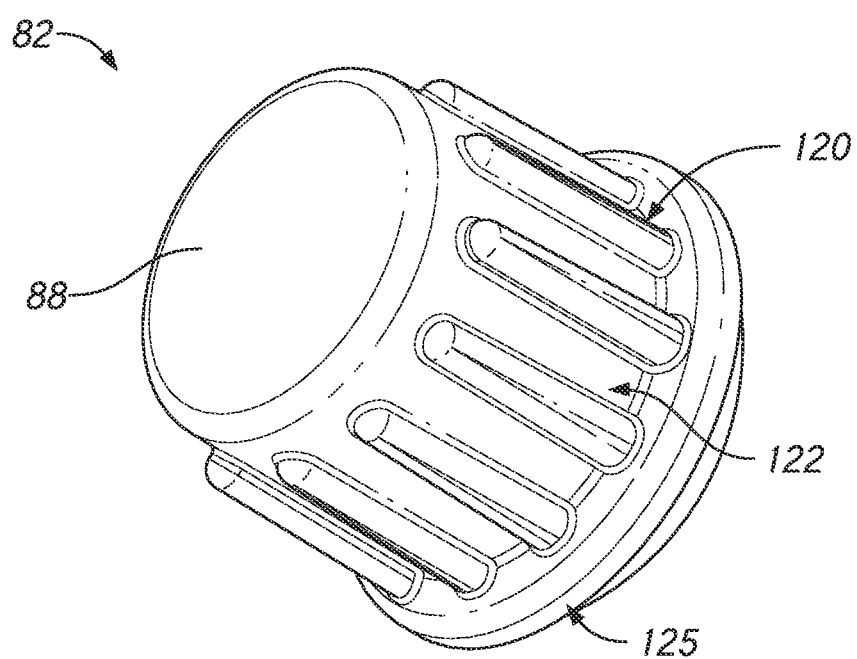
FIG. 1B is a rear perspective view of the antiseptic cap of FIG. 1A.
Figure 1C:
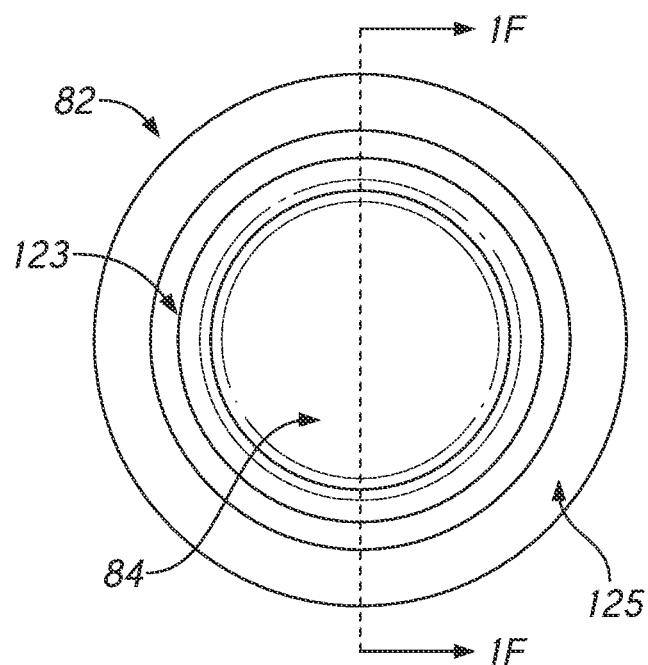
FIG. 1C is a top view of the antiseptic cap of FIG. 1A.
Figure 1D:
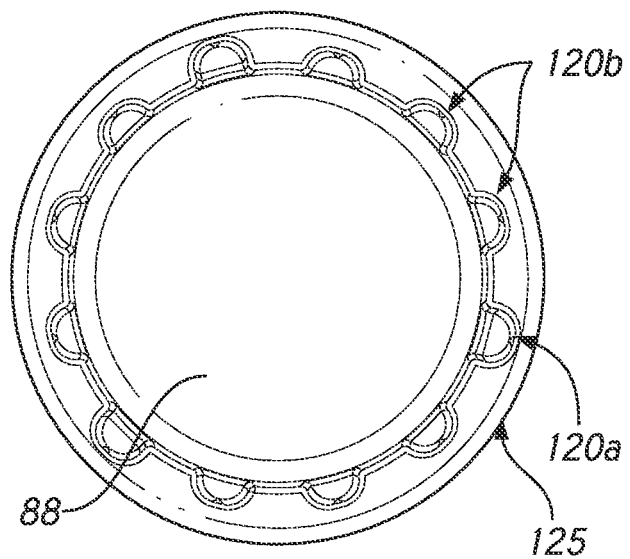
FIG. 1D is a rear view of the antiseptic cap of FIG. 1A.
Figure 1E:
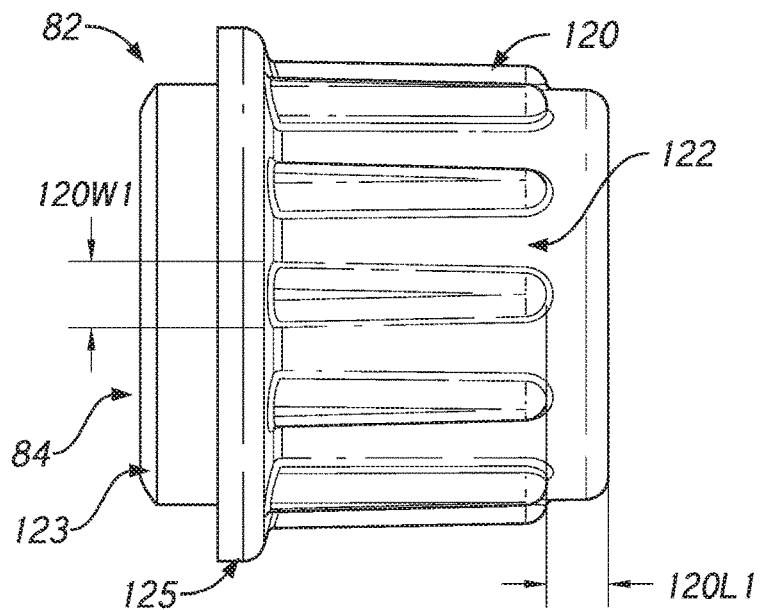
FIG. 1E is a side view of the antiseptic cap of FIG. 1A.
Figure 1F:
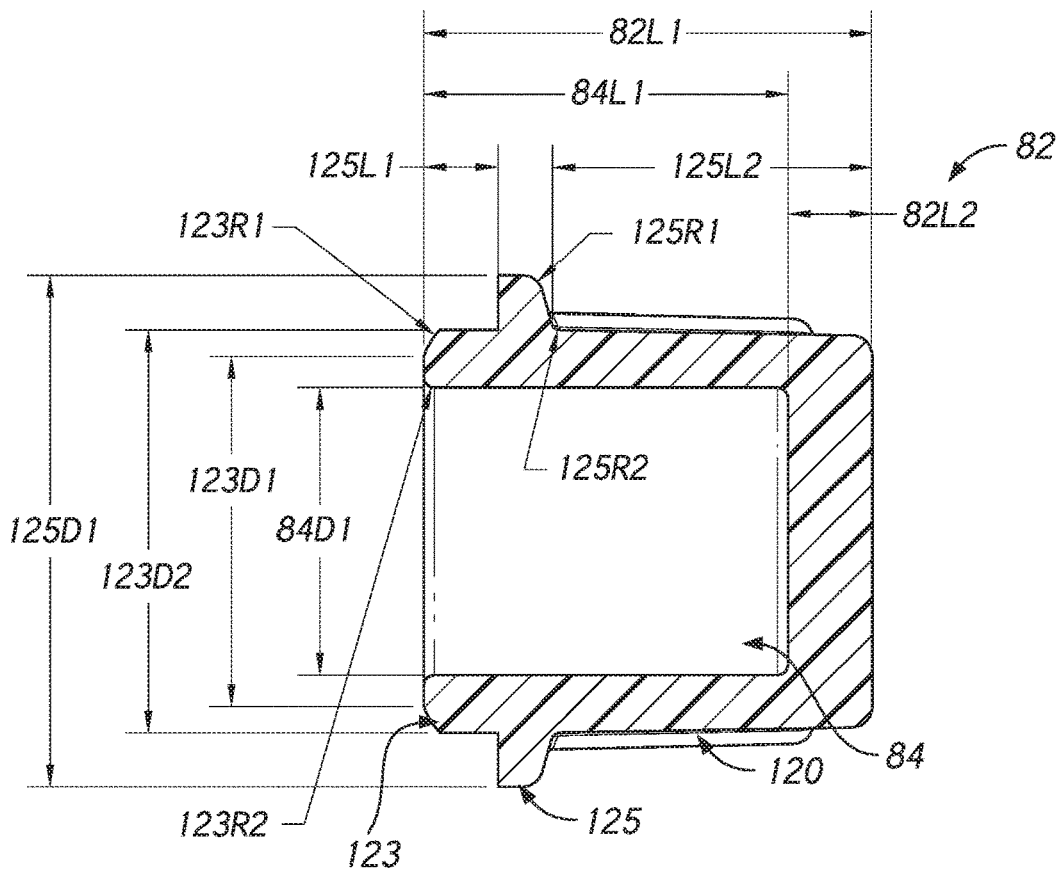
FIG. 1F is a side cross-sectional view of the antiseptic cap of FIG. 1A.
Figure 1G:
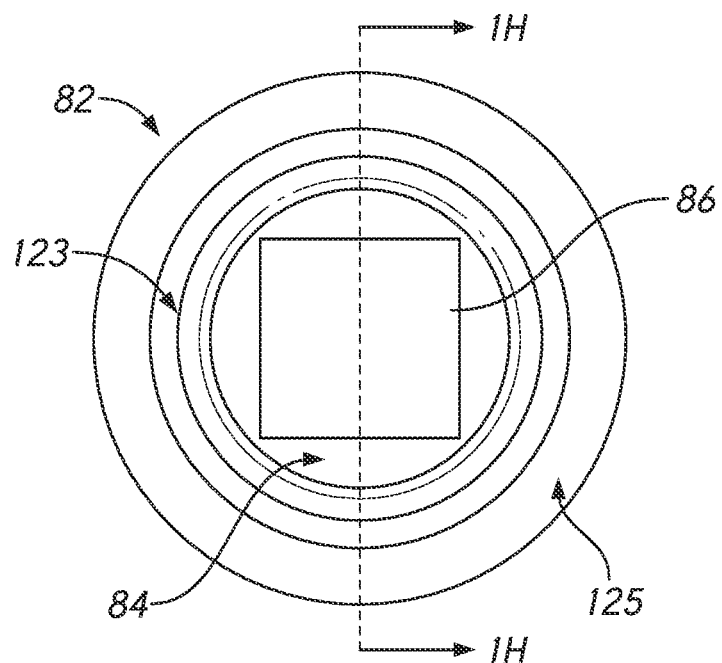
FIG. 1G is a top view of an embodiment of an antiseptic cap.
Figure 1H:
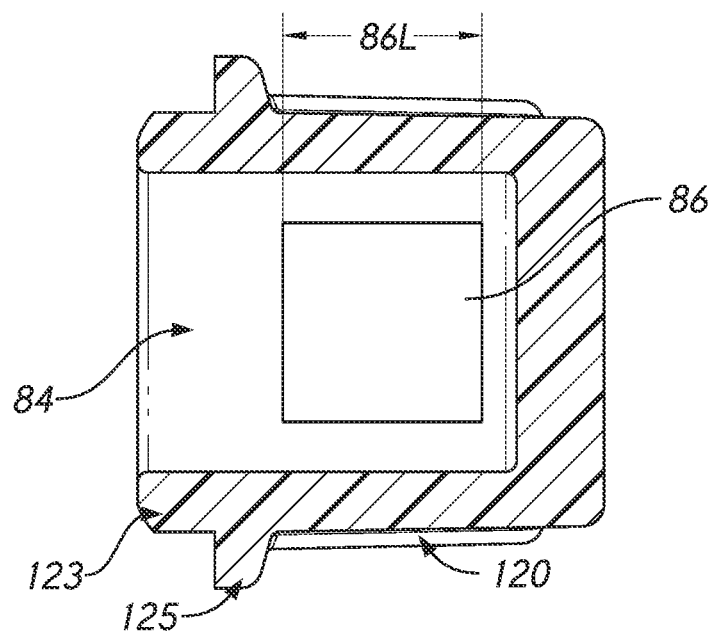
FIG. 1H is a side cross-sectional view of the antiseptic cap of FIG. 1G.

FIGS. 1A-1H are various views of an antiseptic cap 82, according to some embodiments. In particular, FIG. 1A is a front perspective view of an antiseptic cap 82, FIGS. 1B-1F are rear perspective, top, bottom, side, and side cross-sectional views of the antiseptic cap 82 of FIG. 1A, respectively, and FIGS. 1G and 1H are top and side cross-sectional views of the antiseptic cap 82 of FIG. 1A including an antiseptic material 86. Unless otherwise noted, reference numerals in FIGS. 1A-1H refer to components that are the same as or generally similar to the components in the remaining figures discussed herein. It will be understood that the antiseptic cap 82 shown in FIGS. 1A-1H can be used with any of the embodiments described and/or contemplated herein. It will also be understood that any of the embodiments described and/or contemplated herein can be modified to be used with the antiseptic cap 82 shown in FIGS. 1A-1H.

As shown in FIGS. 1A and 1B, the antiseptic cap 82 can include a first chamber 84. The first chamber 84 can be configured to be removably attached to a medical connector. For example, in some embodiments, the first chamber 84 can comprise an interior surface 87 configured to interact with a portion of a medical connector, such as, for example, an end of a medical connector, one or more threads of a medical connector, and/or one or more features of a medical connector, among others. In some embodiments, the interior surface 87 can be threadless and have any suitable surface texture, such as, for example, smooth and/or rough. In some embodiments, the first chamber 84 can be pushed and/or twisted onto and/or off a portion of a medical connector. In some embodiments, a diameter 84D1 of the interior surface 87, as shown in FIG. 1F, may be essentially the same size as, or slightly smaller than, or slightly larger than, a diameter of the outer surface of the medical connector to facilitate interaction between the antiseptic cap 82 and the medical connector. For example, at least a portion of the interior surface 87 can be configured to slidably contact a portion of the medical connector to which the cap 82 is configured to attach during attachment, urging the interior surface 87 to resiliently or elastomerically expand or stretch or otherwise move to receive the portion of the medical connector for attachment. In some embodiments, the section of the interior surface 87 that contacts the portion of the medical connector does not include any inwardly directed protrusion such as a screw thread or other surface irregularity but is sufficiently smooth to permit attachment between the cap 82 and the medical connector under a generally axially-directed, user-induced pushing force with a magnitude that is sufficiently low to permit repeated attachment and removal of caps 82 and medical connectors throughout a workday without creating undue strain on the user. The first chamber 84 may have a diameter 84D1 sufficiently large to engage a medical connector, such as by snuggly and/or securely engaging the medical connector to resist unintentional removal. In some embodiments, as illustrated in FIGS. 1A-1F, the first chamber diameter 84D1 may be slightly smaller than a diameter 123D2 of an inner flange 123. Alternatively, diameter 84D1 may be sized to engage a smaller medical connector. In some embodiments, the first chamber 84 can have multiple interior diameters, although it is contemplated that the first chamber 84 may have a singular diameter, as illustrated in FIGS. 1A-1F. The medical connector may be any suitable shape and/or configuration capable of interaction with the interior surface 87 of the antiseptic cap 82. For example, in some embodiments, the medical connector can comprise threads, ridges, ribs, a textured and/or rough surface, etc., although it will be appreciated that the medical connector can include any suitable structure and have any suitable shape.

To facilitate attaching the antiseptic cap 82 to a medical connector, in some embodiments, the antiseptic cap 82 can comprise a semi-rigid material capable of deformation when a load is applied. This can advantageously allow the interior surface 87 of the antiseptic cap 82 to temporarily and/or permanently deform when the interior surface 87 interacts with one or more features of the medical connector. In some embodiments, the antiseptic cap 82 can comprise a rigid material that is sufficiently pliable to permit the interior surface 87 to engage with a portion of a medical connector. In some embodiments, the interface between the medical connector and the cap 82 can form a fluid tight seal. When the antiseptic cap 82 is attached to a medical connector, such a fluid tight seal can be configured to function as a physical barrier that isolates a portion of the first chamber 84 from the outside environment. For example, in some embodiments, the fluid tight seal can be configured to inhibit an antiseptic agent from leaving the isolated portion of the first chamber 84 and/or can be configured to inhibit contaminants from entering the isolated portion of the first chamber 84. It will be appreciated that the ability of the interior surface 87 to deform can advantageously allow the cap 82 to be removably attached to a medical connector without the use of threads. For example, in some embodiments, the semi-rigid material can be configured to allow threads of a medical connector to slide into the first chamber 84 such that the interior surface 87 deforms radially outward as the threads interact with the interior surface 87 when they are sliding in. In some embodiments, the interior surface 87 can be configured to rebound radially inward after the threads interact with the interior surface 87 and slide further into the first chamber 84. When the medical connector is fully inserted into the antiseptic cap 82, the interior surface 87 can be configured to deform radially outward wherever the medical connector interacts with the interior surface. Advantageously, a threadless antiseptic cap (e.g., antiseptic cap 82) can be configured to receive one or more medical connectors having one or more different features (e.g., various thread characteristics, differently sized connectors, among others).

The antiseptic cap 82 can comprise any suitable material (e.g., semi-rigid material). For example, in some embodiments, the antiseptic cap 82 can comprise a thermoplastic elastomer (e.g., Santoprene®). The semi-rigid material of the antiseptic cap 82 can have any suitable durometer. For example, in some embodiments, the antiseptic cap 82 can have a Shore A durometer in the range of approximately 60 to approximately 1050, although any suitable durometer can be used, such as, for example, at least: about 50, about 55, about 60, about 65, about 70, about 75, about 80, about 85, about 90, about 95, about 100, among others (e.g., any durometer between about 50 and about 100). For example, in some embodiments, the antiseptic cap 82 can comprise Santoprene® having a Shore A hardness of at least about 90.

As shown in FIGS. 1A and 1B, the first chamber 84 can receive and/or house any suitable feature. For example, in some embodiments, the first chamber 84 can be configured to house a liquid-dispenser, such as an absorbent material 86 (as shown in FIGS. 1G and 1H) or a portion thereof. For example, in some embodiments, the absorbent material 86 can be placed within the first chamber. The first chamber 84 depth 84L1 may be appropriately sized to hold the absorbent material 86. The first chamber 84 can comprise any suitable shape and/or configuration capable of receiving a portion of a medical connector. For example, as shown in FIG. 1A and 1B, the first chamber 84 can be cylindrically shaped, although it will be appreciated that the first chamber 84 can comprise any suitable wall structure (e.g., straight and/or curved) and have any suitable shape (e.g., cylindrical, tapered, conical). In some embodiments, it will be appreciated, for example, that the second chamber 85 can comprise a shallow depression.

The first chamber 84 can comprise any suitable depth 84L1, shown in FIGS. 1G and 1H, capable of receiving and/or housing a liquid-dispensing material, such as an absorbent material 86, as described herein. The depth 84L1, shown in FIG. 1F, of the first chamber 84 may be sufficiently recessed to prevent accidental or incidental removal of the absorbent material 86 from the first chamber 84. In some embodiments, the depth 84L1 of the first chamber 84 may be less than one half of the length 82L1 of the antiseptic cap 82, while still being sufficiently recessed to house the absorbent material 86. However, it will be appreciated that the first chamber 84 can comprise any suitable shape and/or configuration capable of receiving and/or housing the absorbent material 86. For example, the depth 84L1 of the first chamber 84 may be more than one half of the length 82L1 of the antiseptic cap 82.

As shown in FIGS. 1A-1H, in some embodiments, the antiseptic cap 82 can comprise inner and outer flanges 123, 125 proximate the opening of the first chamber 84. The outer flange 125 may be at a distance 125L1 from the opening of the first chamber 84 and a distance 125L2 from an end wall 88 of the antiseptic cap 82, as shown in FIG. 1F. In alternative embodiments, distance 125L2 may be smaller than 125L1 causing the outer flange 125 to be closer to the end wall 88 of the antiseptic cap 82 than the opening of the first chamber 84. Additionally, the outer flange 125 may extend radially outward from the antiseptic cap 82 with a diameter 125D1. It will be appreciated that locations of the flanges 123, 125, as well as the relative sizes indicated in FIGS. 1A-1H are examples and non-limiting. Indeed, it will be understood, that the locations and relative sizes can be modified for any suitable embodiment, and that their relative proportions can differ in various embodiments. In some embodiments, the antiseptic cap may not incorporate one or more of the flanges 123, 125.

As shown in FIGS. 1A-1H, in some embodiments, an inner flange 123 may be proximate the opening of the first chamber 84. The inner flange 123 may comprise one or more angled surface with internal radii of 123R1, 123R2, shown in FIG. 1F. In some embodiments, an angled surface may extend across only a portion of the exterior surface of the antiseptic cap 82. For example, as shown in FIGS. 35A and 35D through 35F, the angled surface may not extend alone the entire length 125L1 between the opening of the first chamber 84 and the outer flange 125. Alternatively, the angled surface may extend across length 125L1 from the top surface of the antiseptic cap 82 to the outer flange 125. In some embodiments, an angled surface may be located on the interior surface 87 of the antiseptic cap 82, as shown by internal radius 123R2. This can advantageously facilitate interaction of the interior surface 87 with one or more features of the medical connector. In some embodiments, an angled surface may extend across a portion of the width of the antiseptic cap 82 and/or inner flange 123, as shown in FIGS. 1A-1H. It will be appreciated that locations of one or more angled surfaces, as well as the relative sizes indicated in FIGS. 1A-1H are exemplary and non-limiting. Additionally, in some embodiments, the antiseptic cap 82 may not incorporate an angled surface.

FIGS. 1A-1H also illustrate an external interaction portion, such as a plurality of external ribs 120 and a plurality of external slots 122, as described herein. The plurality of external ribs 120 can have any suitable form and/or configuration. For example, as shown in FIGS. 1A-1H, the plurality of ribs 120 can comprise a plurality of axial ribs. In some embodiments, the plurality of ribs 120 can extend between the outer flange 125 to a position proximate the end wall 88 of the antiseptic cap 82, shown in FIGS. 1A-1H as the difference between length 125L2 and length 120L1. In certain embodiments, the plurality of ribs 120 may extend across the entire length 125L2 or across the entire or virtually the entire length of the cap 82 (for example, on caps that do not include an outer flange 125). The plurality of ribs 120 may also have a width of 120W1. While FIG. 1E illustrates an embodiment of the width 120W1, it is understood that the width 120W1 may vary depending on the amount of ribs 120 included on the antiseptic cap 82. The size, shape, and/or position of the external ribs 120 can be configured to facilitate gripping by increasing friction and/or by providing one or more surfaces on which a finger or fingernail can exert a rotational force to facilitate installing or removing the cap 82 from a medical connector. In some embodiments, one or more of the ribs 120 may each comprise a rounded end proximate to the end wall 88 with an internal radius 120R1. The interaction portion or plurality of ribs 120 can be configured to interact with any of the plungers, cap holders, and cap assemblies described and contemplated herein, such as in facilitating the attachment to, removal from, or retention between, the cap 82 and any other structure. For example, in some embodiments, the plurality of ribs 120 can be configured to interact with the cap holder 402 as described herein with respect to FIGS. 13A, 13B, and 19A-19D and the plunger 1240 as described herein with respect to FIGS. 20A and 20B. In some embodiments, the interaction of these various structures can advantageously prevent or resist (also referred to as limit) the relative rotation between the antiseptic cap 82 and a plunger housing, between the antiseptic cap 82 and an antiseptic cap housing, and/or between the antiseptic cap 82 and an antiseptic cap holder assembly.

In some embodiments, the plurality of ribs 120 can comprise any suitable number, such as for example, 1 to 20 or more ribs. In some embodiments, the plurality of ribs 120 can comprise one or more types and/or sizes of ribs. For example, as shown in FIG. 1D, in some embodiments, the antiseptic cap 82 can comprise 12 axial ribs with two different sizes: 3 larger ribs 120a and 9 smaller ribs 120b, although any suitable combination and arrangement can be used. For example, in some embodiments, the large ribs 120a can comprise a dimension (e.g., a diameter) that is greater than the small ribs 120b, such as, for example, a 0.443 inch diameter for the large ribs 120a and a 0.424 inch diameter for the small ribs 120b.

As shown in FIGS. 1G and 1H, the first chamber 84 can house the absorbent material 86. As will be described in more detail below, in some embodiments, the absorbent material 86 can be a cube, although any suitable shape can be used.

As shown in FIGS. 1E and 1F, various features of the cap 82 can comprise the various indicated dimensions. It will be appreciated that these dimensions, as well as the dimensions indicated in the Figures are exemplary and non-limiting. Indeed, it will be understood, that the dimensions can be modified for any suitable embodiment, and that their relative proportions can differ in various embodiments. For example, in some embodiments, the first chamber 84 can have a wider diameter than shown in FIGS. 1A-1H.

FIGS. 1G and 1H include a top view and a side cross-sectional view of an antiseptic cap 82 including an antiseptic-dispensing material or any other liquid-dispensing material, such as an absorbent material 86. As shown in the Figures, the absorbent material 86 placed inside the first chamber 84 of the antiseptic cap 82 can be formed in any size and shape that permits the absorbent material 86 to fit within the first chamber, such as a cube shape with side length 86L, although any suitable shape can be used. The side length 86L may be smaller than the diameter 84D1 of the first chamber 84 to allow the absorbent material 86 to reside within the first chamber 84. In some embodiments, the side length 86L may be smaller than the depth 84L1 of the first chamber 84 to permit the absorbent material 86 to reside entirely within the first chamber 84. In some embodiments, the absorbent material 86 can be attached within the first chamber 84 via glue, one or more undercuts, one or more ledges, heat staking, and/or a friction fit, although any suitable attachment can be used. For example, in some embodiments, any exterior surface of the antiseptic-dispensing material, such as one or more corners of a cube-shaped antiseptic-dispensing material (e.g., four corners of the cube), can interact with and be retained by or abut against the interior surface 87 of the first chamber 84 so that the absorbent material 86 is held within the first chamber 84 by any suitable means against the interior surface 87 of the first chamber 84, such as via a friction fit or by glue or adhesive or by any other connection or attachment or retention method or step disclosed anywhere in this specification. In some embodiments, the absorbent material 86 can comprise foam, such as, for example, a polyurethane (ester) open-cell foam with a density of about 0.8 to about 2.8 pounds per cubic foot.

Some examples of devices and cap assemblies that can be configured to use an antiseptic cap without threads (e.g., the antiseptic cap 82 as described above with reference to FIGS. 1A-1H) are illustrated and described in U.S. Patent Application Publication No. 2013/0006194 and U.S. Patent Application Publication No. 2015/0217106, both of which are incorporated by reference in their entireties herein and made a part of this specification, and any feature, structure, material, step, or component of any embodiment described and/or illustrated in any of these can be used with or instead of any other feature, structure, material, step, or component of any embodiment described and/or illustrated elsewhere in this specification.

Antiseptic Cap with Thread Cover

Figure 2:
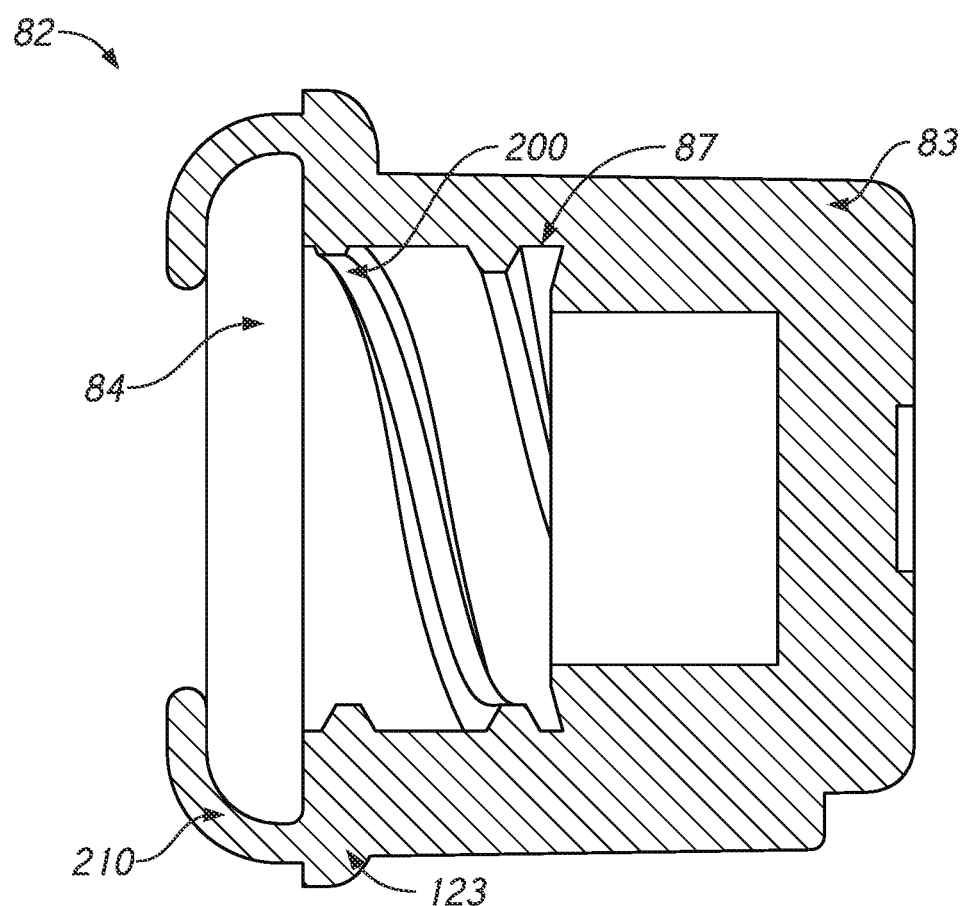
FIG. 2 is a side cross-sectional view of another embodiment of an antiseptic cap.

FIG. 2 is a view of an antiseptic cap 82, according to some embodiments. In particular, FIG. 2 is a side cross-sectional view of an antiseptic cap 82. Unless otherwise noted, the antiseptic cap 82 as shown in FIG. 2 may include components that are the same as or generally similar to the components in the remaining figures discussed herein. It will be understood that the antiseptic cap 82 shown in FIG. 2 can be used with any of the embodiments described and/or contemplated herein. It will also be understood that any of the embodiments described and/or contemplated herein can be modified to be used with the antiseptic cap 82 shown in FIG. 2.

As shown in FIG. 2, an antiseptic cap 82 can include a wall 83 defining a first chamber 84. The first chamber 84 can be configured to be removably attached to a medical connector, as discussed herein. For example, in some embodiments, the first chamber 84 can comprise an interior surface 87 configured to interact with a portion of a medical connector, such as, for example, an end of a medical connector, one or more threads of a medical connector, and/or one or more features of a medical connector, among others.

In some embodiments, as shown in FIG. 2, the interior surface 87 can include a set of threads 88. The threads 88 may be configured to mate with a corresponding set of threads on a medical connector. For example, in some embodiments, the antiseptic cap 82 may be rotated clockwise or counterclockwise to engage the threads 88 of the antiseptic cap 82 with corresponding threads of the medical connector. After engagement, the antiseptic cap 82 may remain docked to the medical connector. The antiseptic cap 82 can remain docked to the medical connector for any period of time.

As shown in FIG. 2, the threads 200 may extend along about one half of the length of the interior surface 87 of the antiseptic cap 82. However, it will be appreciated that the threads 200 may comprise any suitable length and/or configuration capable of engaging a corresponding medical connector. For example, in some embodiments, the threads 200 may extend along an entire length of the interior surface 87.

In some embodiments, as illustrated in FIG. 2, the antiseptic cap 82 may include a thread cover 210. The thread cover 210 can be part of any of the antiseptic caps discussed herein. The thread cover 210 may be configured to enhance a connection between the antiseptic cap 82 and a medical connector. The thread cover 210 can provide a physical barrier to the ingress of pathogens, dust or other contaminants through the mating the antiseptic cap 82 and the medical connector to which the antiseptic cap 82 is docked. In some embodiments, the thread cover 210 may also serve to retain any antiseptic fluids and/or antiseptic materials within the antiseptic cap 82 from leaking out of the antiseptic cap 82. For example, antiseptic fluids and/or antiseptic materials may leak out through any threads 200 of the antiseptic cap 82.

The thread cover 210 can be sized and configured to provide a universal fit to most commercially available valves, connectors and access devices, or the thread cover 210 can be customized to dock with a particular access device.

FIG. 2 shows, as described herein, that the antiseptic cap 82 can have a wall 83 having a first end and a second end. In some embodiments, as illustrated, the first end can have a greater diametrical dimension than the second end. The wall 83 can comprise a first chamber 84 having an open end. In some embodiments, the thread cover 302 may be attached by an optional bonding layer to the first end of the wall 83.

The thread cover 210 may be made of a deformable material capable of flexing upon application of force. In some embodiments, the thread cover 210 may comprise the same material as any other portion of the antiseptic cap 82. Alternatively, the thread cover 210 may comprise a material different than one or more portions of the cap. As shown in FIG. 2, the thread cover 210 may be integrally formed with the remainder of the antiseptic cap 82. However, it will be understood that the thread cover 210 may be a separate piece that is removably attached to the antiseptic cap 82. The thread cover 210 may be made a part of the antiseptic cap 82 using any suitable technique, such as overmolding, or by attaching as a separate part using welding techniques such as heat conductive welding, heat induction welding, sonic welding, vibrational welding, stretch or friction fit, or by using a suitable adhesive or solvent. In some embodiments, the thread cover 210 is made from a polymeric containing material. The polymeric material may have a modulus of elasticity of less than 20,000 psi, although it will be understood that the polymeric material may have a modulus of elasticity greater or lower than 20,000 psi. In some embodiments, the polymeric material can comprise an elastomer or plastomer or like material.

Antiseptic Cap with Outer Shroud

Figure 3A:
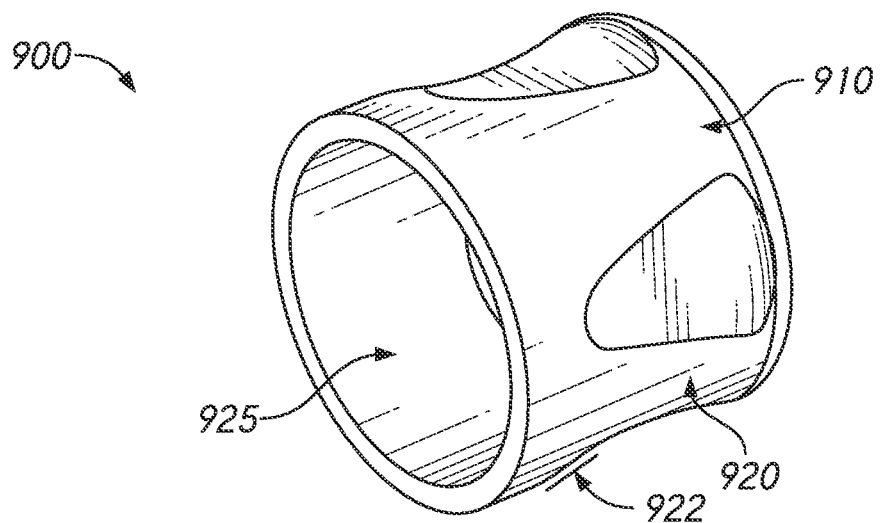
FIG. 3A is a front perspective view of an embodiment of an antiseptic cap.
Figure 3B:
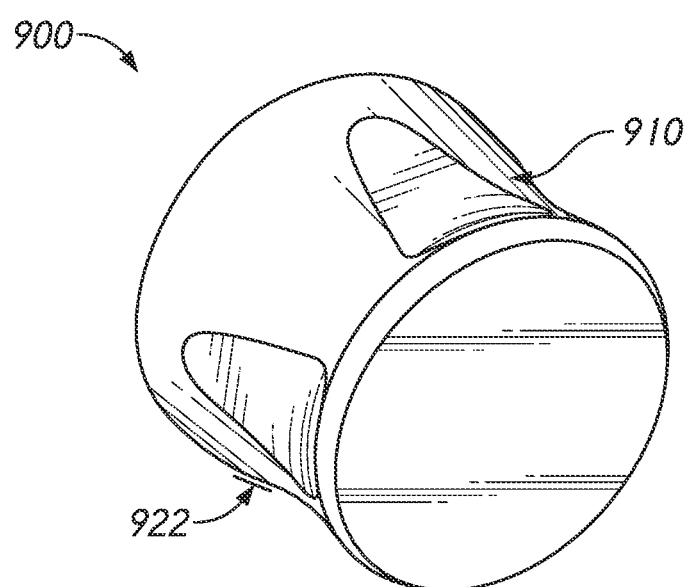
FIG. 3B is a rear perspective view of the antiseptic cap of FIG. 3A.
Figure 3C:
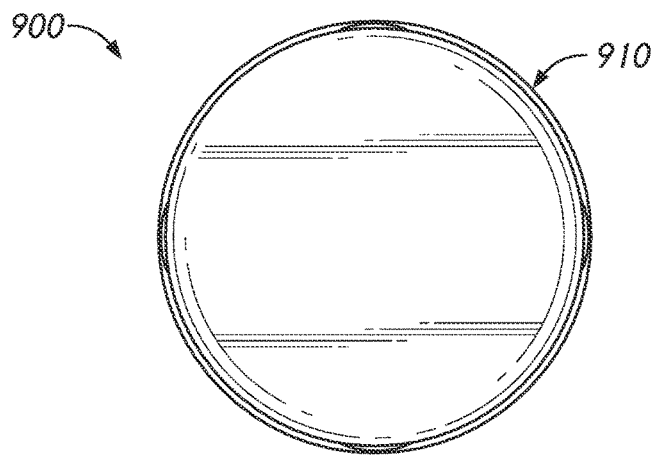
FIG. 3C is a rear view of the antiseptic cap of FIG. 3A.
Figure 3D:
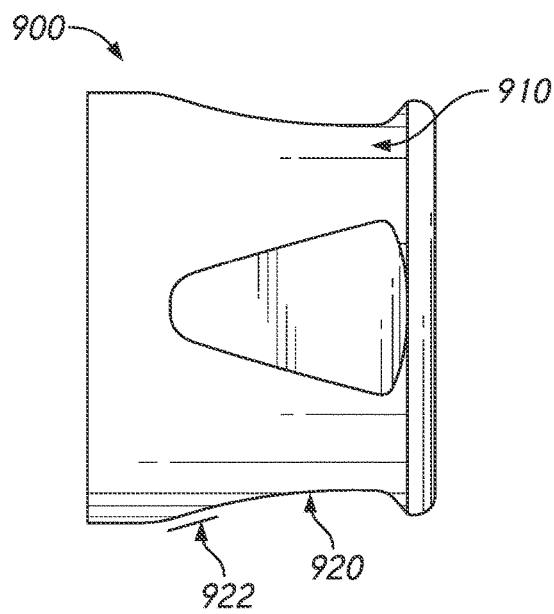
FIG. 3D is a side view of the antiseptic cap of FIG. 3A.
Figure 3E:
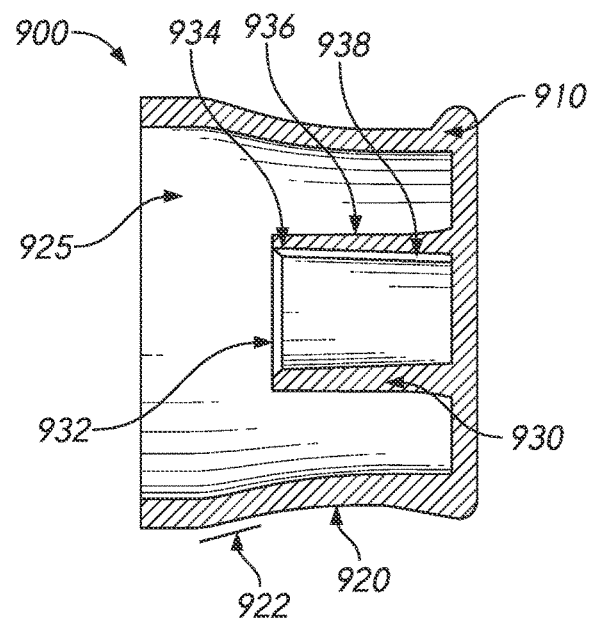
FIG. 3E is a side cross-sectional view of the antiseptic cap of FIG. 3A.
Figure 4:
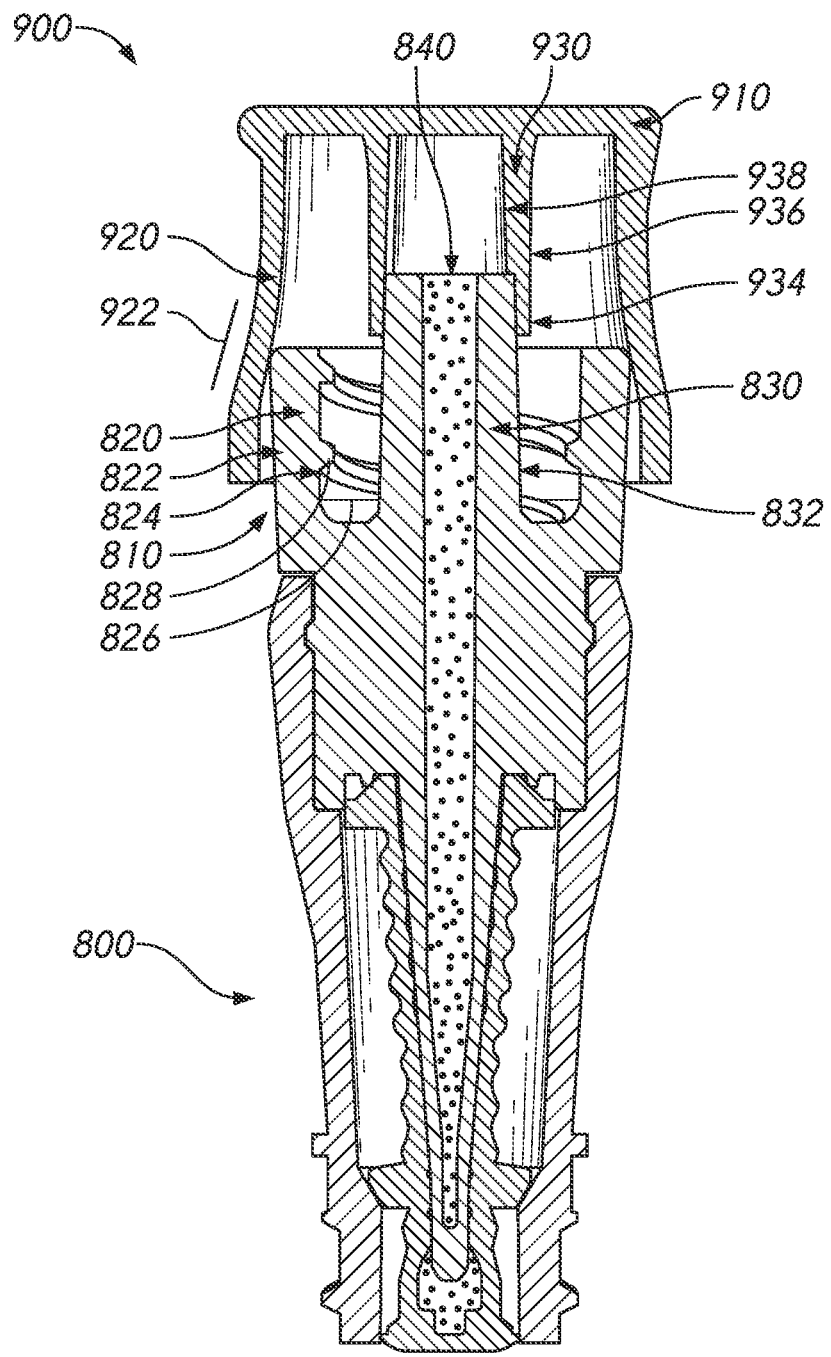
FIG. 4 is a side cross-sectional view of an embodiment of an antiseptic cap.
Figure 5:
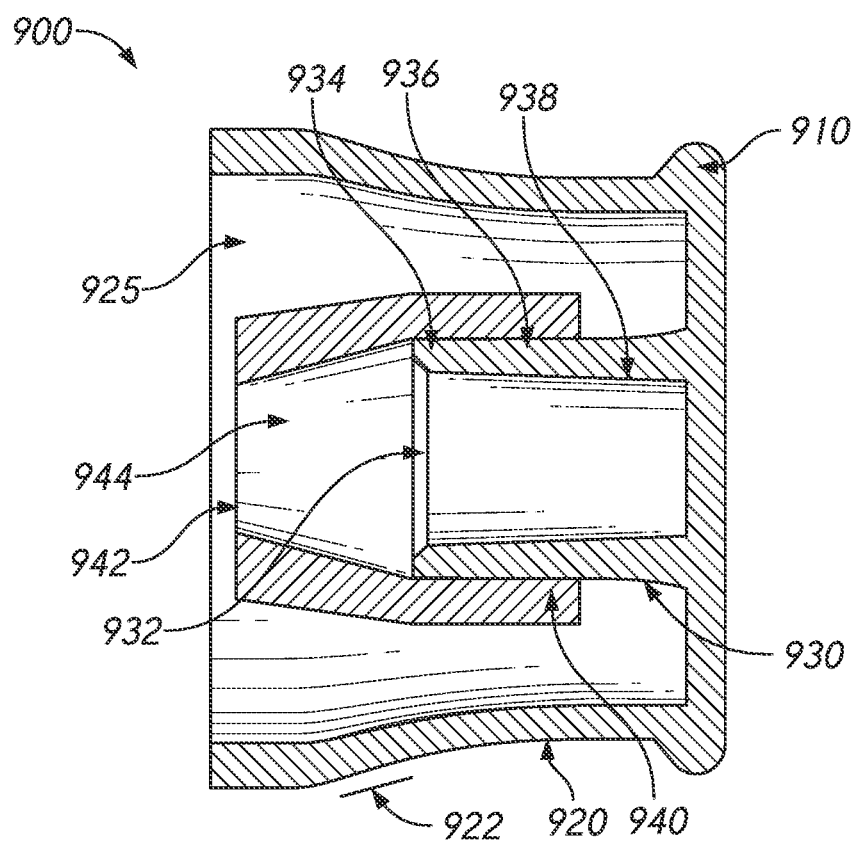
FIG. 5 is a side cross-sectional view of an embodiment of an antiseptic cap.
Figure 6:
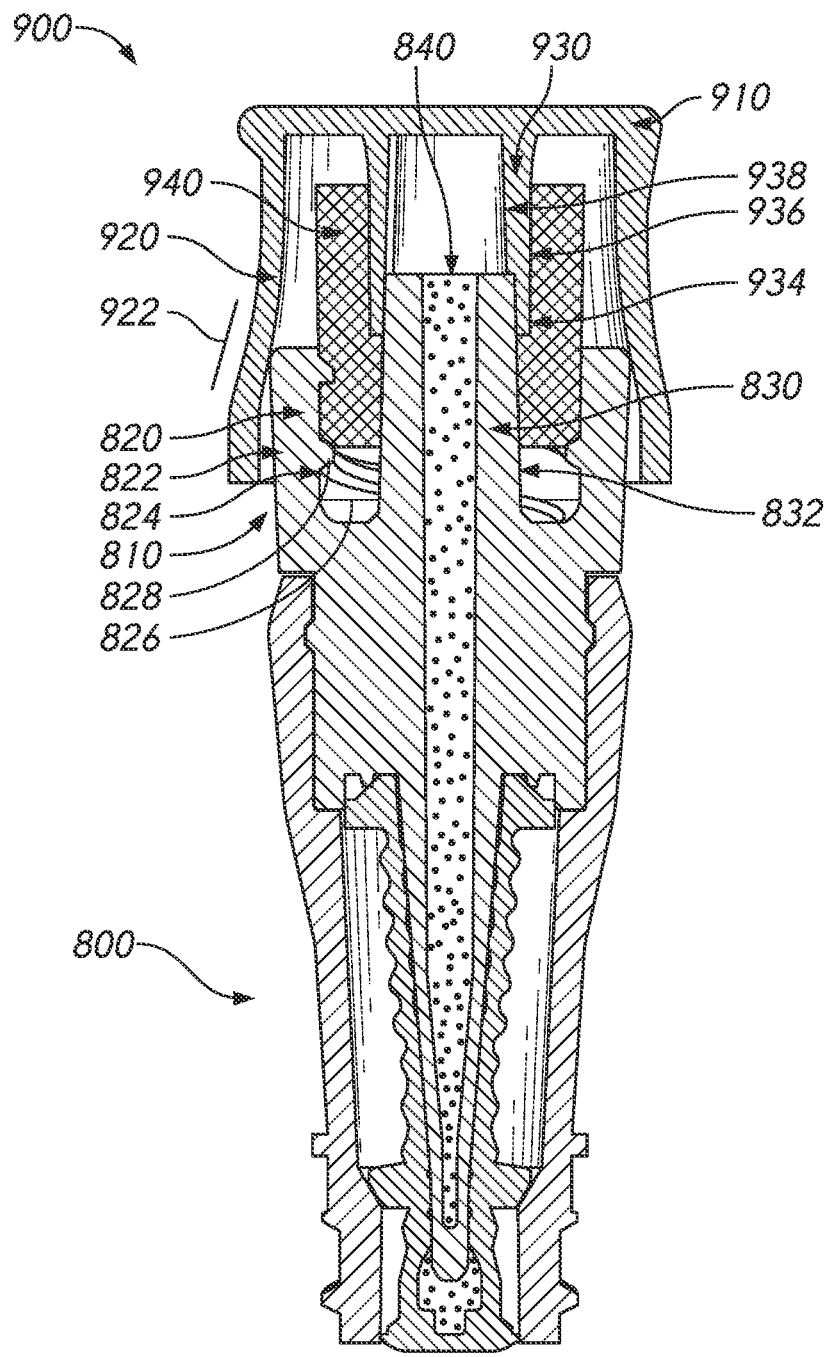
FIG. 6 is a side cross-sectional view of an embodiment of an antiseptic cap.

FIGS. 3A-3E are various views of an antiseptic cap 900, according to some embodiments. In particular, FIG. 3A is a front perspective view of an antiseptic cap 900, FIGS. 3B-3E are rear perspective, rear, side, and side cross-sectional views of the antiseptic cap 900 of FIG. 3A, respectively, and FIG. 4 is a side cross-sectional view of an antiseptic cap 900 coupled to a male luer connector 800. Additionally, FIGS. 5 and 6 are side cross-sectional views of an antiseptic cap 900 including an absorbent material 940. Unless otherwise noted, the antiseptic cap 900 as shown in FIGS. 3A-6 may include components that are the same as or generally similar to the components in the remaining figures discussed herein. It will be understood that the antiseptic cap 900 shown in FIGS. 3A-6 can be used with any of the embodiments described and/or contemplated herein. It will also be understood that any of the embodiments described and/or contemplated herein can be modified to be used with the antiseptic cap 900 shown in FIGS. 3A-6. As with all embodiments in this specification, any feature, structure, material, method, or step that is described and/or illustrated in the embodiment of FIGS. 3A-3E can be used with or instead of any feature, structure, material, method, or step that is described and/or illustrated in any other embodiment of this specification.

As shown in the Figures, the cap 900 comprises a housing 910 including a first chamber 925. The first chamber 925 can be configured to be removably attached to a medical connector 800, as illustrated in FIGS. 4 and 6. For example, in some embodiments, the first chamber 925 can comprise an interior surface configured to interact with a portion of a medical connector 800, such as, for example, an end region or male end of a medical connector, one or more threads of a medical connector, and/or one or more other features of a medical connector. It will be understood that any feature, structure, material, step, or component of any embodiment described and/or illustrated herein (such as the first chamber 84 of antiseptic cap 82 of FIGS. 1A-1H) can be used with or instead of any other feature, structure, material, step, or component of any embodiment of antiseptic cap 900 of FIGS. 3A-6.

As shown, and in some embodiments, the housing 910 includes a skirt 920 and a protrusion 930. As illustrated, in some embodiments, the skirt 920 and the protrusion 930 can be positioned and/or oriented such that their respective central longitudinal axes are generally collinear, such as with the protrusion 930 positioned within the skirt 920. As shown, and in some embodiments, the protrusion 930 has an opening or recess 932 (see FIG. 3E), the opening 932 comprising a proximal lip or rim 934 that can be distally recessed within the skirt 920, such that the exterior surface of the cap 900 extends further in the proximal direction than the proximal-most tip of the protrusion 930.

As shown in FIGS. 3A-3E, the first chamber 925 can receive and/or house any suitable feature. For example, in some embodiments, the cap 900 comprises a fluid-delivery material, such as an absorbent material 940 shown in FIGS. 5 and 6. FIG. 4 shows a cross-sectional view of the cap 900 without an absorbent material 940 coupled to a medical connector 800 from the embodiment in FIGS. 3A-3E. FIG. 6 shows a cross-sectional view of the cap 900 including an absorbent material 940 coupled to a medical connector 800 from the embodiment in FIG. 5. As shown, and in some embodiments, the absorbent material 940 is attached partially or entirely within the first chamber 925, such as to an outer surface 936 of the protrusion 930, and/or does not attached to an inner surface 938 of the protrusion, and/or is connected to the protrusion 930 such that at least a portion of the absorbent material 940 overhangs or extends proximally beyond the lip or rim 934 of the protrusion 930. The absorbent material 940 may be the same as or generally similar to any liquid-dispensing, fluid-delivery, absorbent, and/or antiseptic material discussed and/or illustrated anywhere in this specification.

As described herein, in some embodiments, the protrusion 930 has an opening 932 comprising a lip or rim 934. As shown in FIG. 5, and in some embodiments, the cap 900 may further comprise an absorbent material 940, the absorbent material 940 being attached to an outer surface 936 of the protrusion 930 such that at least a portion of the absorbent material 940 overhangs or extends beyond the lip or rim 934 of the protrusion 930. As shown, a proximal end of the fluid-delivery or absorbent material 940 can be positioned in a distal direction from a proximal end of the cap 900, such that the fluid-delivery or absorbent material 940 is recessed distally when the cap 900 is inverted and resting on a horizontal surface, as shown in FIG. 5, to thereby resist contact between the fluid-delivery or absorbent material 940 and microbes or other contaminants before use or between uses, when the cap 900 is inverted. In some embodiments, the absorbent material 940 can be made of a deformable material such as foam. In some embodiments, at least a portion of the absorbent material 940 can be stretched over the outer surface 936 of the protrusion 930. As shown, and in some embodiments, the absorbent material 940 has an opening 942 and a hollow channel 944 for contacting and cleaning the male luer 830 of a male luer connector 800.

As shown, the fluid-delivery or absorbent material 940 can be positioned and/or oriented on and/or within the cap 900 such that the proximal end of the fluid-delivery material 940 extends further in the proximal direction than the proximal-most tip of the protrusion 930. An interior space within the fluid-delivery material 940 can comprise a tapered surface, as shown in FIG. 5. For example, as illustrated, in some embodiments the proximal end of the fluid-delivery material 940 can be narrower than a region of the fluid-delivery material 940 that is spaced distally from the proximal end, which can cause the proximal end of the fluid-delivery material 940 to more tightly grip the male luer of the connector 800 when attached, as the cap 900 is advanced onto the connector 800.

As shown in FIGS. 5 and 6, the distal end of the fluid-delivery material 940 can be spaced proximally from the interior surface of the base of the cap 900, such as to form a void between the distal end of the fluid-delivery material 940 and the interior surface of the base of the cap 900. As illustrated, the exterior surface of the base of the cap 900 can be flat and/or planar, and/or substantially flat and/or substantially planar so as to permit the cap 900 to be positioned on a horizontal surface without tipping over or rolling away. In some embodiments, the absorbent material 940 can be made of a compressible, deformable, and/or resilient material such as foam or textile or cloth or gauze. However, any suitable material can be used as the fluid-delivery material or absorbent material 940. In some embodiments, the absorbent material 940 (or any other fluid-delivery or liquid-dispensing material disclosed or illustrated elsewhere in the text or drawings of this specification) is configured to carry and deliver a therapeutic liquid or gel, such as a liquid or gel antiseptic or antimicrobial agent. For example, the therapeutic liquid or gel can be isopropyl alcohol, or chlorhexidine gluconate, or metallic ions such as silver ions or copper ions, or any other suitable agent or agents for sanitizing, washing, and/or removing contaminants.

FIG. 4 illustrates an embodiment of a cap 900 coupled to a male luer connector 800. As shown, the male luer connector 800 comprises a connector housing 810. In some embodiments, the connector housing 810 includes a shroud or collar 820 having an exterior surface 822 and an interior surface 824. The interior surface 824 can comprise a connection interface 826. The connection interface 826, in some instances, can include threading 828. The connector housing 810 may include a male luer 830 having an exterior surface 832. As shown, and in some embodiments, the male luer 830 includes a fluid passageway 840.

As discussed herein with reference to FIGS. 4 and 6, in some embodiments, the cap 900 can be coupled to the male luer connector 800 such that the cap 900 protects or shields or covers or provides resistance to the connector 800 from contamination. In some embodiments, as shown in FIG. 6, when the cap 900 is coupled to the connector 800, the absorbent material 940 of the cap 900 is positioned in direct contact with the connection interface 826 of the male luer connector 800. In some embodiments, the absorbent material 940 is in direct contact with the threading 828 of the connection interface 826. In some embodiments, the absorbent material 940 is in direct contact with the exterior surface 832 of the male luer 830. In some embodiments, the absorbent material 940 is spaced away from the male luer connector 800 and/or the connection interface 826. In some embodiments, when the absorbent material 940 comes into direct contact with the connection interface 826 of the male luer connector 800, the absorbent material 940 contacts, cleans, wipes, and/or sanitizes the connection interface 826. In some embodiments, the absorbent material 940 contacts, cleans, wipes, and/or sanitizes the threading 828 of the connection interface 826. In some embodiments, when the absorbent material 940 comes into direct contact with the exterior surface 832 of the male luer 830, the absorbent material 940 contacts, cleans, wipes, and/or sanitizes the male luer 830. Cleaning or wiping can include removing one or more substances or organisms from a surface of a medical connector in an amount or to a degree that provides a clinically significant therapeutic effect, such as removing one or more substances or organisms in an amount configured to avoid or to resist an adverse medical consequence in a patient, such as a disease or an infection or some other undesirable medical outcome.

Any or all of the steps of cleaning and/or sanitizing can include wiping along a surface to be cleaned and/or sanitized during connection. In some embodiments, as shown in FIG. 6, the fluid-delivery material can simultaneously clean and/or sanitize the exterior surface of the male luer 830 and the interior surface of the shroud or collar 820, such as by simultaneously contacting and/or wiping the exterior surface of the male luer 830 and the interior surface of the shroud or collar 820. As illustrated in FIG. 6, the fluid-delivery material 940 can be sufficiently thick to fill a void between an exterior surface of the male luer 830 and an interior surface of the shroud or collar on the distal end of the male connector 800. The fluid-delivery material 940 can compress between these surfaces. As shown in FIGS. 5 and 6, a space can be provided between an exterior surface of the fluid-delivery or absorbent material 940 and an interior surface of the exterior wall or skirt 920 of the cap 900, such that the exterior surface of the fluid-delivery or absorbent material 940 does not contact the interior surface of the exterior wall or skirt 920 of the cap 900. As shown in FIG. 6, in some embodiments, at least a portion of the space can be generally equal to, and/or no larger than, the thickness of the wall of the shroud or collar on the distal end of the connector 800, and at least a portion of the space can be smaller than the thickness of the wall of the shroud or collar on the distal end of the connector 800.

In some embodiments, as illustrated in FIGS. 4 and 6, the skirt 920 contacts or covers or overlays against or extends across at least a portion of the exterior surface 822 of an end region, such as a distal end region of the collar 820 of the connector 800. In some embodiments, the skirt 920 can include a tapered region, such as a tapered region 922 near a proximal end of the cap 900. In some embodiments, the cross-sectional width of the tapered region 922 can increase in a distal-to-proximal direction. In the illustrated embodiments, the tapered region 922 facilitates coupling between the cap 900 and the male luer connector 800. The tapered region 922 can facilitate coupling between the skirt 920 and the collar 820. For example, the cross-sectional width of the skirt 920 decreases as the distal end of the connector 800 is inserted in a distal direction into the proximal end of the skirt 920, thereby increasing the tightness of the connection or grip or attachment between cap 900 and the connector 800.

In some embodiments, the skirt 920 may not include a tapered region 822. As illustrated in FIGS. 4 and 6, in some embodiments, the interior face of the exterior wall of the cap 900 frictionally contacts or attaches to the connector on an exterior surface of the connector, and/or the interior face and/or the exterior face of the exterior wall of the cap 900 does not contact or attach in any threaded region or in any region within the interior of the collar or shroud of the connector 800. As shown, the outer cross-sectional width of the proximal end of the cap 900 can be larger than the outer cross-sectional width of the portion of the connector 800 to which the cap 900 is configured to attach. In some embodiments, as illustrated, the cap 900 can be attached to and/or removed from the connector 800 by axially or longitudinally pushing the cap 900 onto or pulling the cap 900 away from the connector 800 in a single proximal or distal direction, without requiring rotation or screwing of the cap 900 onto or into the connector 800. In some embodiments, as shown in FIGS. 3E and 5, the exterior surface of the cap 900 has a curved or non-straight sidewall, which can facilitate securely grasping the cap 900 with the fingers. As shown in FIGS. 3A-3D, in some embodiments the exterior side surface of the cap 900 can comprise one or more generally flat regions to facility grasping the cap 900 with the fingers. In some embodiments, as illustrated, the distal base of the cap 900 can comprise a radially outwardly extending surface that forms a lip to provide a region that resists sliding of the fingers when the cap 900 is removed from the connector 800 by axially or longitudinally pulling the cap 900 away from the connector 800. As shown in FIGS. 3E and 5, the interior face of the exterior wall of the cap 900 can be smooth, without substantial protrusions or recesses or threads.

With further reference to FIGS. 4 and 6, when the cap 900 is coupled to the male luer connector 800 as shown, the male luer 830 is received by the opening or recess 932 of the protrusion 930. In some embodiments, during or after coupling, an inner surface 938 of the protrusion 930 is moved adjacent to or into contact with at least a portion of the exterior surface 832 of the male luer 830 such that at least a portion of the male luer 830 is positioned within and/or secured to the protrusion 930. In some embodiments, as illustrated, when the cap 900 is coupled to the male luer 830, the male luer 830 can be sealed, no longer in communication with the environment, which can resist vaporization of liquid contents within the male luer 830 into the environment and/or ingress of environmental contaminants into the male luer 830. As illustrated in FIG. 5, in some embodiments, the interior of the protrusion 930 is empty or devoid of a fluid-delivery material or therapeutic fluid or antiseptic and/or there is no structure or material between the male luer 830 and the distal end of the interior of the protrusion 930 when the cap 900 is attached to the male luer connector 800. In some embodiments, the securing of the protrusion or the positioning of the protrusion within the male luer 830 prevents the therapeutic liquid or gel that is carried by the absorbent material 940 or otherwise present in the cap 900 from entering into the fluid passageway 840 of the male luer 830. As illustrated, in some embodiments, no structure of the cap 900 is configured to enter into or contact the fluid passageway 840 of the connector 800 when the cap 900 is connected to the connector 800.

Antiseptic Male Protrusion Cap

Figure 7A:
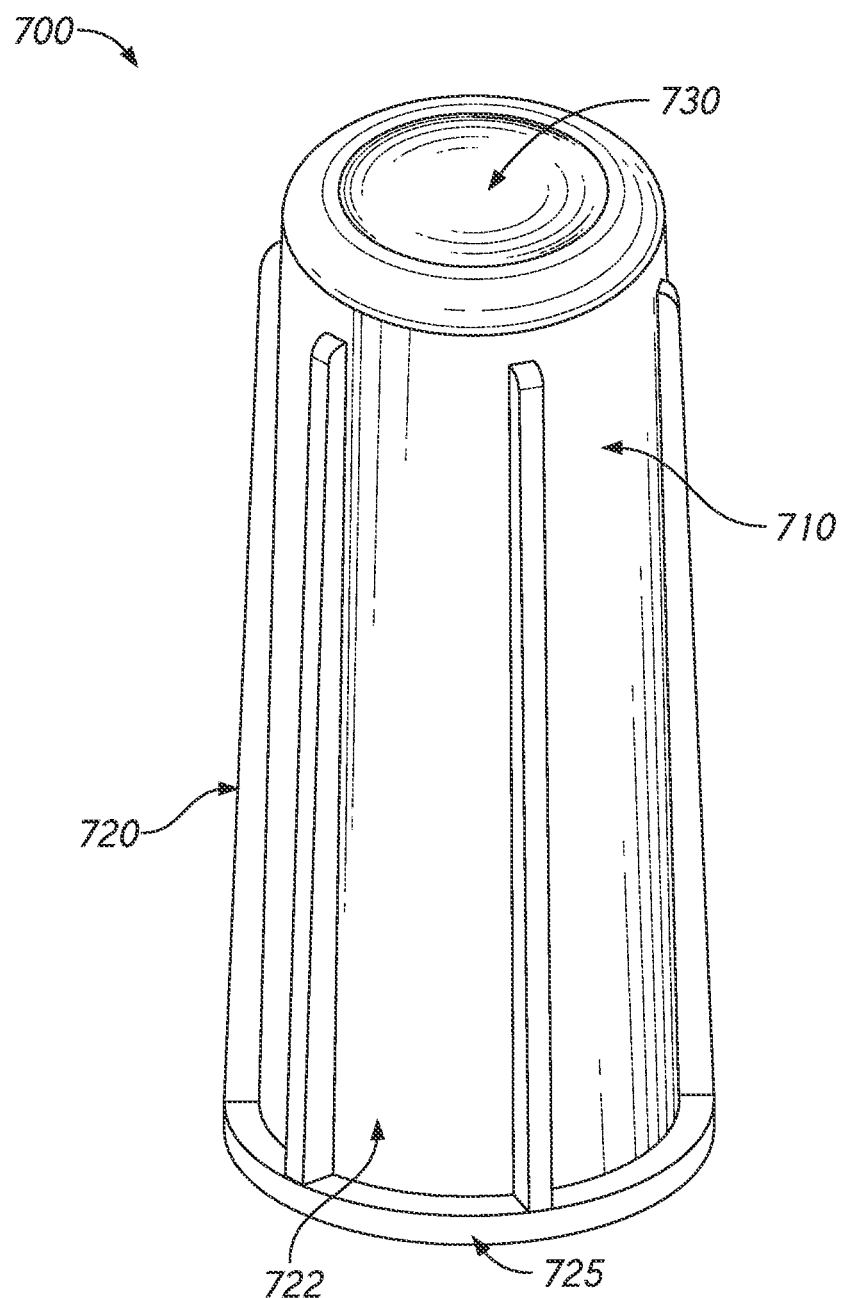
FIG. 7A is a front perspective view of an embodiment of an antiseptic cap.

FIGS. 7A-7E are various views of an antiseptic cap 700, according to some embodiments. In particular, FIG. 7A is a front perspective view of an antiseptic cap 700, and FIGS. 7B-7E are first side cross-sectional, second side cross-sectional, top, and bottom views of the antiseptic cap 700 of FIG. 7A, respectively. Unless otherwise noted, the antiseptic cap 700 as shown in FIGS. 7A-7E may include components that are the same as or generally similar to the components in the remaining figures discussed herein. It will be understood that the antiseptic cap 700, or any components or features thereof, shown in FIGS. 7A-7E can be used with any of the embodiments described and/or contemplated herein. It will also be understood that any of the embodiments described and/or contemplated herein, or any components or features thereof, can be modified to be used with the antiseptic cap 700 shown in FIGS. 7A-7E.

Figure 7B:
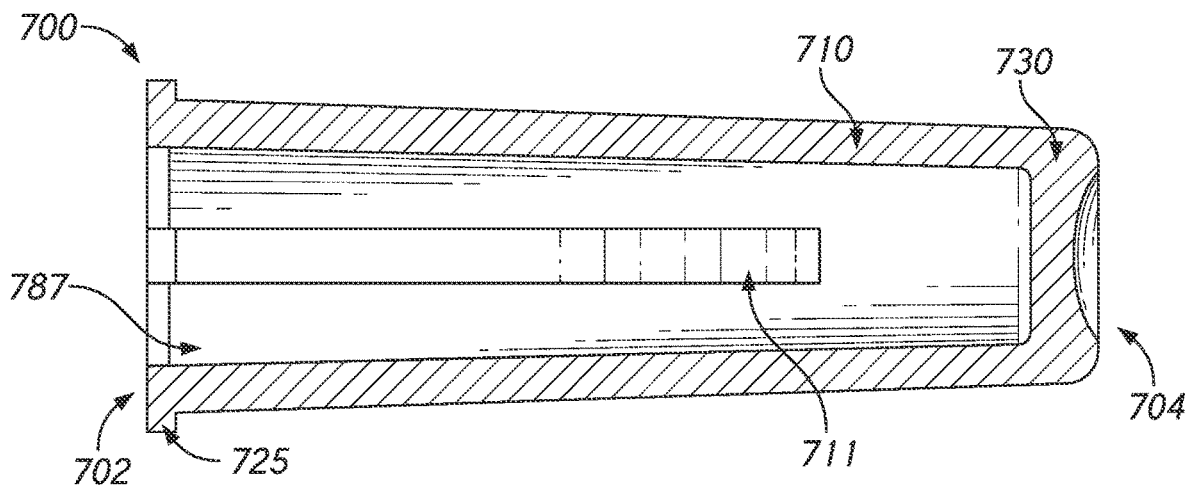
FIG. 7B is a side cross-sectional view of the antiseptic cap of FIG. 7A.

Shown in FIG. 7A is an embodiment of an assembly comprising a cap 700 including a base 710 with a connection region that is configured to connect with and/or to receive and/or to cover a corresponding connection region on a medical implement, such as a male protrusion (e.g., a male luer) of the medical implement. As shown in FIG. 7B, the base 710 can comprise a proximal end 702 with a proximal opening that leads into an interior region 787 within the base 710. The base 710 can comprise a distal end 704 including a closed end 730. The outer surface of the base 710 can be configured to be gripped by a user of the cap 700, such as during attachment or screwing onto the medical implement. For example, in some embodiments, the outer surface of the base 710 can comprise a plurality of ribs 720 and a plurality of external slots 722, as illustrated in FIGS. 7A and 7E. The plurality of ribs 720 can have any suitable form and/or configuration. It will be understood that any feature, structure, material, step, or component of any embodiment described and/or illustrated herein (such as the plurality of ribs 120 and plurality of slots 122 of antiseptic cap 82 of FIGS. 1A-1H) can be used with or instead of any other feature, structure, material, step, or component of any embodiment of antiseptic cap 700 of FIGS. 7A-7E.

In some embodiments, the opening of the base 710 and/or the interior region 787 of the base 710 can comply with one or more, or all, of the luer requirements of any version of ISO standard 594 or ISO 80369 or any other industry standard that is applicable to medical fluid connectors. For example, the proximal opening of the base 710 can be approximately the same diameter and include approximately the same taper as a male luer of a medical connector to which the cap 700 is configured to attach. In some embodiments, the cap 700 can comprise a fluid-delivery material, such as an absorbent material within and/or attached to the base 710, as described in further detail herein. For example, in some embodiments, an absorbent material can be placed within the interior region 787 of the base 710. In some embodiments, the base 710 can comprise one or more flanges, such as outer flange 725 shown in FIGS. 7A-7E. The outer flange 725 can have any suitable form and/or configuration. It will be understood that the outer flange 725 may include any feature, structure, or component of any flange described and/or illustrated herein (such as the inner flange 123 and/or outer flange 125 of antiseptic cap 82 of FIGS. 1A-1H).

In some embodiments, the base 710 is made of material that is rigid, resilient, and/or flexible. The base 710 material may be any suitable material, such as plastic (e.g., polypropylene), or any material that is suitable to cover a connection portion of a medical connector, or any material that is resistant to microorganism growth.

Figure 7C:
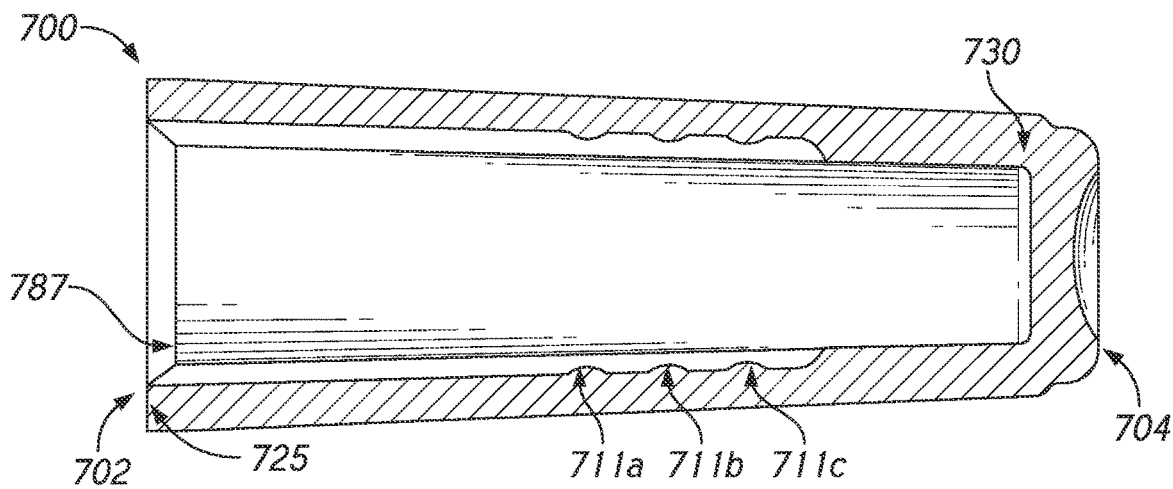
FIG. 7C is another side cross-sectional view of the antiseptic cap of FIG. 7A.

FIGS. 7B and 7C are cross-sectional views of an embodiment taken along the coupling direction. After coupling the cap 700 and a connector region of the medical implement (e.g., a male projection or male luer), in some embodiments, the coupled cap and the connection region of the medical implement are hermetically sealed such that no liquid or fluid or gas can pass from the interior region 787 of the cap 700 to the outside of the cap 700 when attached.

Figure 7D:
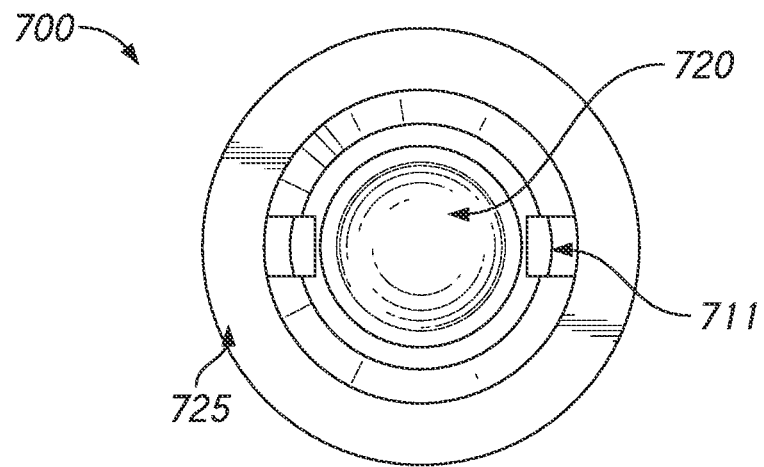
FIG. 7D is a top view of the antiseptic cap of FIG. 7A.
Figure 7E:
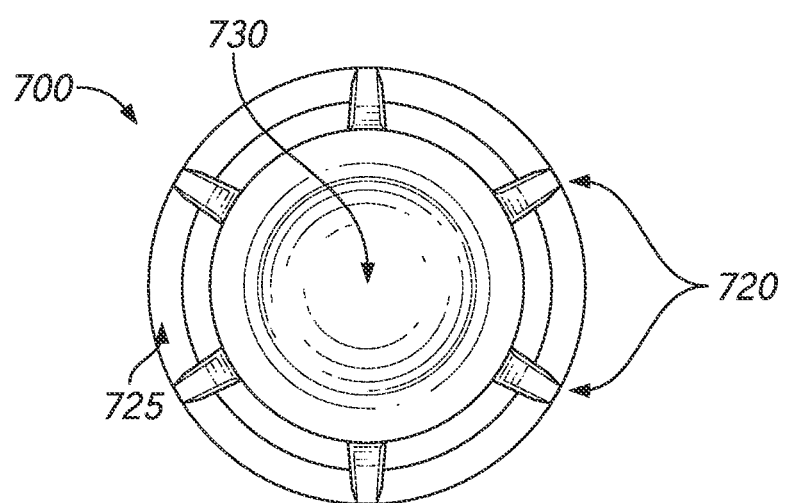
FIG. 7E is a rear view of the antiseptic cap of FIG. 7A.

In some embodiments, the assembly 700 may have one or more ventilating structures, pores, slits and grooves, that make the assembly breathable such that one or more of liquid, fluid, or gas can pass from the inside of the cap to the outside of the cap. FIGS. 7B-7D show an embodiment illustrating an example of such a structure in the form of grooves 711 within the interior region 787 of the cap 700. These grooves 711, when the assembly 100 is coupled with a male protrusion may leave open channels through which excess antiseptic can evaporate into the atmosphere. In some base 710 embodiments, such structure may not exist.

The grooves 711 can have any suitable form and/or configuration. For example, as shown in FIGS. 7B-7D, the grooves 711 can comprise a plurality ribs extending circumferentially along an interior surface within the interior region 787 of the cap 700. In some embodiments, the grooves 711 can extend along an entire circumference of an interior surface. In embodiments, as illustrated in FIGS. 7B-7D, the grooves 711 may only extend along a portion of the interior surface. While FIGS. 7B-7D show an embodiment of the grooves 711 having an illustrated width, it is understood that the width of one or more grooves 711 may vary depending on the amount of grooves 711 included within the cap 700. In some embodiments, the grooves 711 may comprise rounded end proximate to the distal end portion 704 of the cap 700. The grooves 711 may be configured to interact with any one of the medical implement (e.g., male luer or male projection) configured to couple to cap 700, as described herein. In some embodiments, the grooves 711 may interact with one or more portions of the medical implement to advantageously prevent or resist (also referred to as limit) the relative rotation between the cap 700 and the medical implement.

In some embodiments, the grooves 711 can comprise any suitable number, such as for example, 1 to 10 or more grooves. In some embodiments, the grooves 711 can comprise one or more types and/or sizes of grooves. For example, as shown in FIG. 1D, in some embodiments, the antiseptic cap 82 can comprise three grooves 711a, 711b, and 711c. In some embodiments, the three grooves 711a, 711b, 711c may comprise different sizes, although any suitable combination and arrangement can be used.

Projections

Figure 8C:
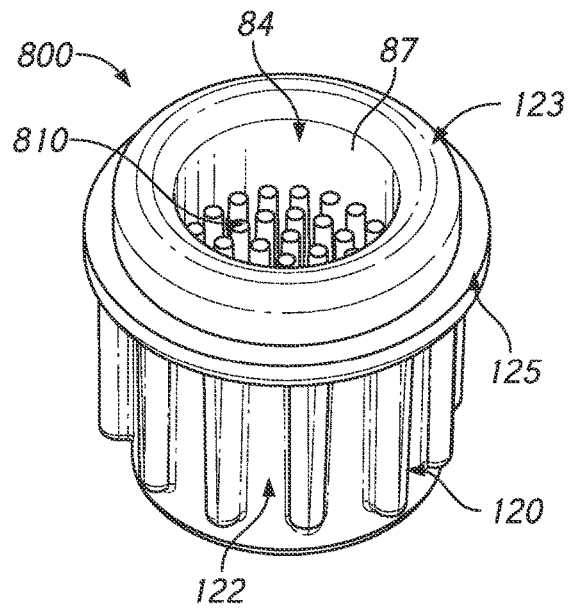
FIG. 8C is a side cross-sectional view of the antiseptic cap of FIG. 8A.
Figure 8C:
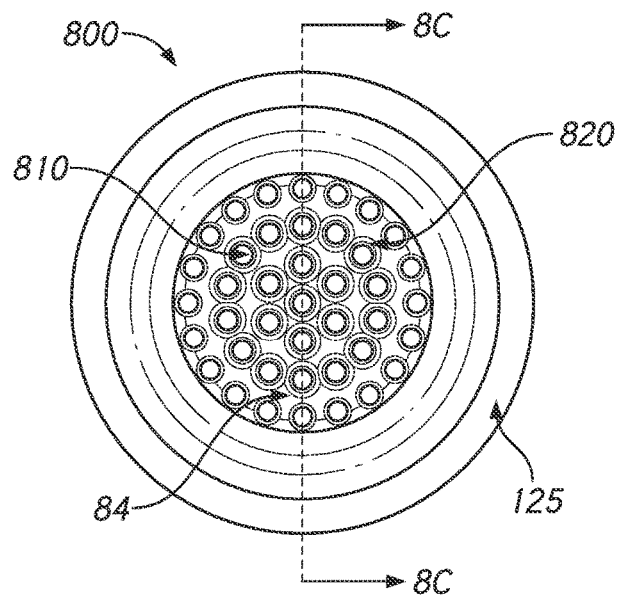
Figure 8C:
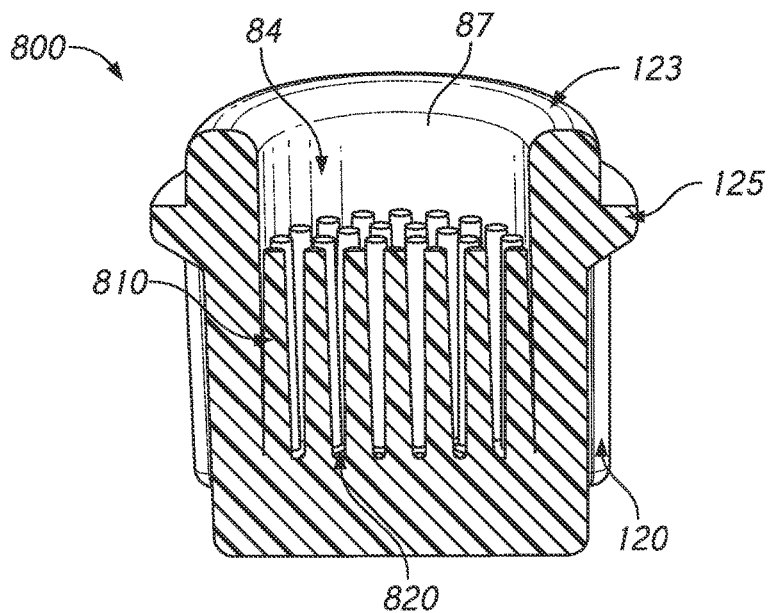

FIGS. 8A-8C are various views of an antiseptic cap 800 including a plurality of projections 810, according to some embodiments. In particular, FIG. 8A is a front perspective view of an antiseptic cap 800 including a plurality of projections 810 and FIGS. 8B and 8C are top and side cross-sectional views of the antiseptic cap 800 of FIG. 8A, respectively. Unless otherwise noted, reference numerals in FIGS. 8A-8C refer to components that are the same as or generally similar to the components in the remaining figures discussed herein. While the antiseptic cap 800 shown in FIGS. 8A-8C is similar to antiseptic cap 82 shown in FIGS. 1A-1H, it will be understood that the features described with reference to antiseptic cap 800 shown in FIGS. 8A-8C can be used with any of the embodiments described and/or contemplated herein. For example, any one of the antiseptic cap 82 of FIG. 2, antiseptic cap 900 of FIGS. 3A-6, antiseptic 700 of FIGS. 7A-7E, antiseptic cap 82 of FIGS. 9A-9C, antiseptic cap 700 of FIGS. 10A-10E, and/or any additional caps disclosed herein can be modified to include one or more projections 810, and/or any other features, as shown and/or described with reference to FIGS. 8A-8C. It will also be understood that any feature, structure, material, step, or component of any embodiment described and/or illustrated herein can be used with or instead of any other feature, structure, material, step, or component of any embodiment of antiseptic cap 810 of FIGS. 8A-8C.

As shown in the Figures, the antiseptic cap 800 comprises a first chamber 84. The first chamber 84 can be configured to be removably attached to a medical connector, as discussed herein. For example, in some embodiments, the first chamber 84 can comprise an interior surface 87 configured to interact with a portion of a medical connector, such as, for example, an end of a medical connector, one or more threads of a medical connector, and/or one or more features of a medical connector, among others.

In some embodiments, as shown in FIGS. 8A-8C, the antiseptic cap 800 may include one or more projections 810, as described herein. The plurality of projections 810 may be positioned and/or oriented such that their respective central longitudinal axes are generally parallel. However, it will be understood that the plurality of projections 810 can have any suitable form and/or configuration. For example, as shown in FIGS. 8A-8C, the plurality of projections 810 can comprise a plurality of axial protrusions. In some embodiments, the plurality of projections 810 can extend between the bottom wall of the first chamber 84 to a position proximate to an inner flange 123 and/or an outer flange 125 of the antiseptic cap 800, shown in FIGS. 8A-8C. In certain embodiments, the plurality of projections 810 may extend across an entire length of the first chamber 84. The plurality of projections 810 may also have a determined width. While FIG. 8C illustrates an embodiment of the width, it is understood that the width may vary depending on the amount of projections 810 included within the antiseptic cap 800. In some embodiments, one or more of the projections 810 may comprise a rounded end proximate to the inner flange 123 and/or the outer flange 125.

The plurality of projections 810 are configured to interact with any of the medical connectors described and contemplated herein. For example, in some embodiments, the plurality of projections 810 can be configured to interact with a medical connector engaged with the antiseptic cap 800, as described herein. The interaction of these various structures can advantageously contact and clean a medical connector attached to the antiseptic cap 800. As shown in FIGS. 8A-8C, in some embodiments, the projection 810 may have a length shorter than a length of the interior surface 87, such that an exterior surface of the cap 810 extends further than an end tip of the projection 810. In some embodiments, the projections 810 may have a length such that an end of one or more of the projections 810 interacts with an end of the medical connector when the medical connector is attached to the antiseptic cap 82. In some embodiments, the length of one or more projections 810 may be sufficient to interact with one or more portions of the medical connector, once attached to the antiseptic cap 800. In some embodiments, the length of the plurality of projections 810 may be limited to prevent or resist the projections 810 from applying a reactive force that is sufficient to disengage the medical connector from the antiseptic cap 800.

In some embodiments, the projections 810 may contain a uniform diameter and/or width along an entire length of the projection 810. For example, one or more projections 810 comprise a cylindrical shape. Alternatively, at least one or more projections 810 of the antiseptic cap 82 may have a varying width, such that the one or more projections 810 tapers from an end tip of the projection 810 to a base 820 of the projection 810. For example, as illustrated, in some embodiments, the base 820 of a projection 810 can be wider than a portion of the projection 810 extending from the base 820. In some embodiments, a narrower portion of the projection 810 may have increased flexibility with respect to a wider portion of the projection 810 allowing the narrower portion to move more freely within the first chamber 84. The narrower portion of the projection 810 may engage with at least a portion of a medical connector to more tightly grip the connector when attached. For example, the narrower portion of the projection 810 may be sufficient malleable to permit the medical connector to bend, flex, and/or move the projections 810 along at least a portion of the medical connector, thereby enabling the plurality of projections 810 to shift and/or move within the first chamber 84. Alternatively, the projections 810 may be configured to not have more flexible portion and, as such, inhibit movement of the projection when connected to a medical connector.

In some embodiments, the plurality of projection 810 can comprise any suitable number, such as for example, 1 to 50 or more projections. In some embodiments, the plurality of projections 810 can comprise one or more types and/or sizes of projections. For example, in some embodiments, the antiseptic cap 800 can comprise more than 30 axial projections with varying diameters, although any suitable combination and arrangement can be used. For example, in some embodiments, larger projections 810 can comprise a dimension (e.g., a diameter and/or length) that is greater than smaller projections 810.

FIGS. 8A-8C show that in some embodiments the plurality of projections 810 may each comprise a base 820 for attachment of the projections 810 to the antiseptic cap 800. The base 820 can be disposed along a bottom surface of the first chamber 84. The base 820 may be configured to retain the projection 810 within the first chamber 84. As shown in FIGS. 8A-8C, the projection 810 can extend outward from the base 820 and towards a center of the first chamber 84. In one embodiment, the base 820 may be disposed along the bottom wall of the first chamber 84. In some instance, the base 820 may be disposed along a sidewall of the interior surface 87 of the first chamber 84, thereby permitting the projection 810 to extend from the sidewall of the interior surface 87. Additionally or alternatively, the one or more bases 820 may be located along both a bottom wall of the first chamber 84 and a sidewall of the interior surface 87.

The one or more bases 820 of the plurality of projections 810 may be attached to one or more interior surfaces 87 of the first chamber 84, as discussed herein. In some embodiments, the base 820 may be formed with the interior surface 87 of the first chamber 84. For example, the base 820 may be integrally formed with the remainder of the antiseptic cap 800. Integrally forming the base 820 with a surface of the first chamber 84 may, in some instances, advantageously decrease the chances of one or more projections 810 becoming disengaged from the antiseptic cap 800. In some embodiments, at least one of the base 820 and/or a portion of the projection 810 may be formed separate from the antiseptic cap 800.

The first chamber 84 can receive and/or house any suitable antiseptic. For example, in some embodiments, the antiseptic cap 800 may utilize the plurality of projections 810 as an antiseptic fluid-delivery material. As shown in FIGS. 8A-8C, the plurality of bases 820 of the plurality of projections 810 can be spaced from each other, such as to form a void between the projections 810. In some embodiments, the antiseptic cap 800 may comprise an absorbent material secured between the projections 810. Alternatively, the antiseptic cap 800 may not include an absorbent material and may include an antiseptic fluid retained between the projections 810. In some embodiments, the antiseptic fluid may be retained within the first chamber 84 by the plurality of projections 810. The antiseptic fluid may be the same as or generally similar to any antiseptic material discussed herein.

Antiseptic fluid may be maintained between the plurality of projections 810 through capillary action. As such, in some embodiments, the number, size, and/or distance between one or more of the projections 810 may be configured to ensure that the capillary attractive forces interacting between the antiseptic fluid and the projections 810 is sufficient to retain the antiseptic fluid within the first chamber 84. For example, the antiseptic fluid may be recessed and maintained within the first chamber 84 even when the antiseptic cap 800 is inverted and placed in any angle. In some embodiments, retaining the antiseptic fluid within the first chamber 84 advantageously inhibits contact between the projections 810 and/or antiseptic fluid and microbes or other contaminants before use or between uses, when the antiseptic cap 800 is inverted during delivery and/or prior to use.

As illustrated, the exterior surface of the projections 810 can be flat and/or planar, and/or substantially flat and/or substantially planar. In some embodiments, the projections 810 may have any suitable surface texture, such as, for example, smooth and/or rough. In some embodiments, the projections 810 can be made of a compressible, deformable, and/or resilient material. However, any suitable material can be used.

As shown in FIGS. 8A-8C, various features of the antiseptic cap 800 can comprise the various indicated dimensions. It will be appreciated that these dimensions, as well as the dimensions indicated in the Figures are exemplary and non-limiting. Indeed, it will be understood, that the dimensions can be modified for any suitable embodiment, and that their relative proportions can differ in various embodiments. For example, in some embodiments, the plurality of projections 810 can have a wider or smaller diameter than shown in FIGS. 8A-8C.

Second Chamber

Figures 9A, 9B:
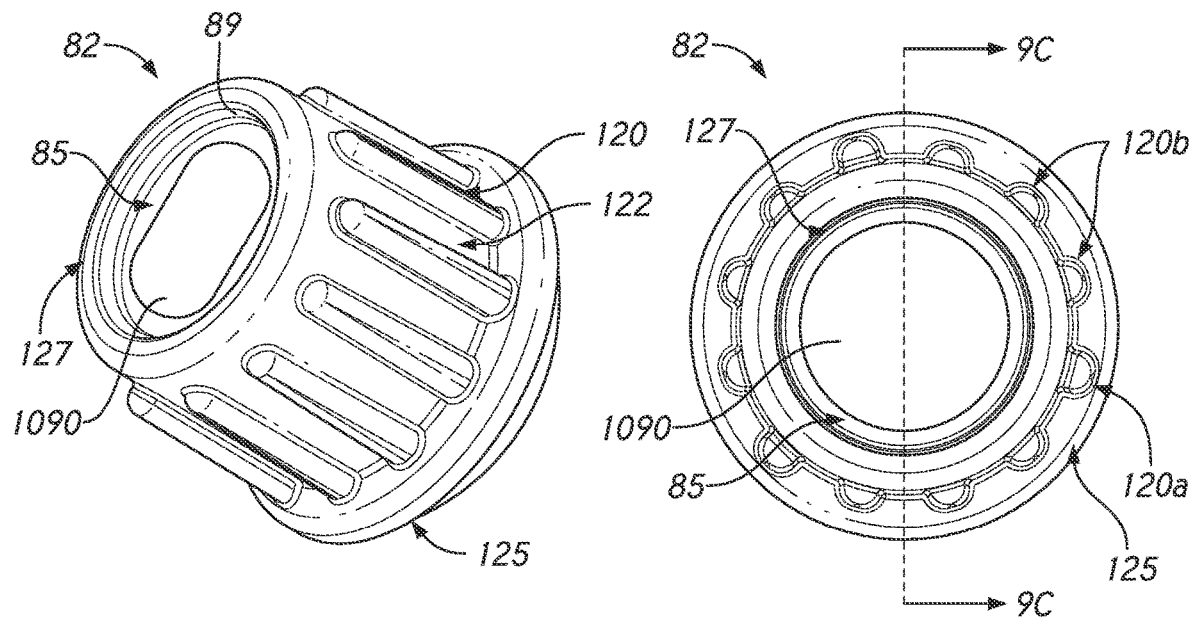
FIG. 9A is a rear perspective view of an embodiment of an antiseptic cap.
FIG. 9B is a rear view of the antiseptic cap of FIG. 9A.
Figure 9C:
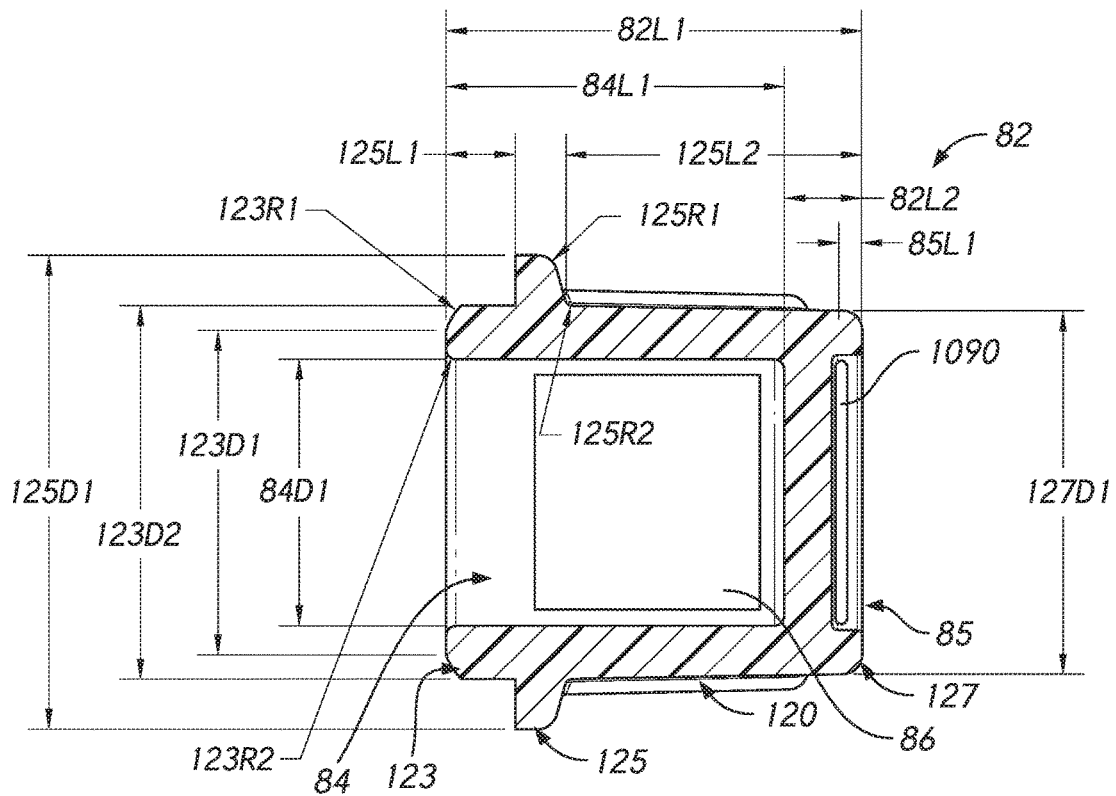
FIG. 9C is a side cross-sectional view of the antiseptic cap of FIG. 9A.

FIGS. 9A-9C are various views of an antiseptic cap 82 including a second chamber 85, according to some embodiments. In particular, FIG. 9A is a rear perspective view of an antiseptic cap 82 including a second chamber 85, FIGS. 9B and 9C are rear and side cross-sectional views of the antiseptic cap 82 of FIG. 9A, respectively. Unless otherwise noted, reference numerals in FIGS. 9A-9C refer to components that are the same as or generally similar to the components in the remaining figures discussed herein. While the antiseptic cap 82 shown in FIGS. 9A-9C is similar to antiseptic cap 82 shown in FIGS. 1A-1H, it will be understood that the features described with reference to antiseptic cap 82 shown in FIGS. 9A-9C can be used with any of the embodiments described and/or contemplated herein. For example, any one of the antiseptic cap 82 of FIG. 2, antiseptic cap 900 of FIGS. 3A-6, antiseptic 700 of FIGS. 7A-7E, antiseptic cap 800 of FIGS. 8A-8C, and/or any additional caps disclosed herein can be modified to include a second chamber 85, as shown and described with reference to FIGS. 9A-9C. It will also be understood that any feature, structure, material, step, or component of any embodiment described and/or illustrated herein can be used with or instead of any other feature, structure, material, step, or component of any embodiment of antiseptic cap 82 of FIGS. 9A-9C.

As shown in FIGS. 9A-9C, the antiseptic cap 82 can include first and second chambers 84, 85. In some embodiments, the second chamber 85 can comprise an interior surface 89 configured to extend around the perimeter of the second chamber 85. In some embodiments, a diameter of the interior surfaces 85D1, as shown in FIG. 9C, may be larger than a diameter of the outer surface of the medical connector to facilitate interaction between the antiseptic cap 82 and the medical connector. In certain embodiments, the second chamber 85 may have an interior diameter 85D1 that is generally the same size as the first chamber 84 interior diameter 84D1. Alternatively, the diameters may be different sizes. In some embodiments, as shown in FIG. 9C, the second chamber 85 can have multiple interior diameters, inner diameter 85D1 and out diameter 85D2, although it is contemplated that the second chamber 85 may have a singular diameter. The medical connector may be any suitable shape and/or configuration capable of interaction with the interior surface 89 of the antiseptic cap 82. For example, in some embodiments, the medical connector can comprise threads, ridges, ribs, a textured and/or rough surface, etc., although it will be appreciated the medical connector can comprise any suitable structure and have any suitable shape.

As shown in FIGS. 9A-9C, the second chamber 85 can receive and/or house any suitable feature. For example, in some embodiments, the second chamber 85 can be configured to house an additive 1090 or a portion thereof. For example, in some embodiments, the additive 1090 can be placed within the second chamber 85, respectively. The second chamber 85 depth 85L1 may be appropriately sized to hold the additive 1090. The second chamber 85 can comprise any suitable shape and/or configuration capable of receiving a portion of a medical connector. For example, as shown in FIGS. 9A-9C, the second chamber 85 can be cylindrically shaped, although it will be appreciated the second chamber 85 can comprise any suitable wall structure (e.g., straight and/or curved) and have any suitable shape (e.g., cylindrical, tapered, conical). In some embodiments, the second chamber 85 can comprise a shallow depression or recess.

A suitable additive 1090 can be configured to inhibit ingestion of the cap 82 or can be configured to inhibit the placing of the cap 82 in the mouth of a patient, such as in the mouth of an infant patient. In some embodiments, the additive 1090 may comprise a negative-taste agent that is unpleasant, repulsive, unattractive, and/or undesirable to human taste. For example, the negative-taste agent can taste bitter, hot, spicy, sour, sharp, vinegary, and/or putrid to an average human. The additive 1090 can be incorporated into and/or integrated within the cap 82 in any suitable way. For example, in some embodiments, a piece of paper or any other delivery vehicle (e.g., a sponge or a foam or a gel, etc.) comprising an additive 1090 can be attached to the cap 82, such as by placing it within the second chamber 85 (e.g., the paper can be coated with the additive 1090), a sticker comprising an additive 1090 can be attached to a portion of the cap 82 (e.g., a sticker coated with the additive 1090 can be placed within the second chamber 85), an additive 1090 can be blended into the material of the cap 82 (e.g., by way of impregnation, or any other process which results in the additive 1090 becoming a part of the material matrix of the cap), and/or an additive 1090 can be coated on a portion of the material of the cap 82 (e.g., by spraying the cap with the additive 1090 or by treating the cap with a liquid comprising an additive 1090), among others (e.g., the cap 82 can comprise an additive 1090 material that releasably retains the additive 1090). In some embodiments, the additive 1090 can comprise Bitrex® compound (available from Johnson Matthey Fine Chemicals company of Scotland), although any suitable negative-taste agent can be used. In some embodiments, the additive 1090 can be incorporated into and/or integrated with an antiseptic cap holder (e.g., cap holders 402) in any suitable way as described above with respect to the cap 82. The additive 1090 can advantageously inhibit ingestion of the cap 82 (e.g., if a child places the cap 82 in her or his mouth). While the additive 1090 shown in FIGS. 9A-9C is described in the context of the antiseptic cap 82 shown in FIGS. 1A-1H, it will be understood that the additive 1090 may be used with any of the embodiments described and/or contemplated herein.

The depth 85L1, shown in FIG. 9C, of the second chamber 85 may be sufficiently recessed to prevent or resist accidental or incidental removal of the additive 1090 from the second chamber 85. For example, in some embodiments, the depth 85L1 of the second chamber 85 may be less than the depth 84L1 of the first chamber 84. Alternatively, the depth 85L1 of the second chamber 85 may be greater than the depth 84L1 of the first chamber 84. In some embodiments, the depth 85L1 of the second chamber 85 and/or depth 84L1 of the first chamber 84 may be less than one half of the length 82L1 of the antiseptic cap 82, while still being sufficiently recessed to house the absorbent material 86 or the additive 1090. However, it will be appreciated that the first chamber 84 and second chamber 85 can comprise any suitable shape and/or configuration capable of receiving and/or housing the absorbent material 86 or additive 1090. For example, the depth 85L1 or depth 84L1 of the first chamber 84 may be more than one half of the length 82L1 of the antiseptic cap 82.

As shown in FIGS. 9A-9C, in some embodiments, the antiseptic cap 82 can comprise inner and outer flanges 123, 125 proximate the opening of the first chamber 84, as described herein, and a flange 127 proximate the opening of the second chamber 85. The outer flange 125 may be at a distance 125L1 from the opening of the first chamber 84 and a distance 125L2 from the opening of the second chamber 85, as shown in FIG. 9C. In alternative embodiments, distance 125L2 may be smaller than 125L1 causing the outer flange 125 to be closer to the opening of the second chamber 85 than the opening of the first chamber 84. Additionally, the outer flange 125 may extend radially outward from the antiseptic cap 82 with a diameter 125D1. It will be appreciated that locations of the flanges 123, 125, 127, as well as the relative sizes indicated in FIGS. 9A-9C are exemplary and non-limiting. Indeed, it will be understood, that the locations and relative sizes can be modified for any suitable embodiment, and that their relative proportions can differ in various embodiments. In some embodiments, the antiseptic cap may not incorporate one or more of the flanges 123, 125, 127.

Absorbent Material Positioned at Least Partially Outside an Antiseptic Cap

Figure 10A:
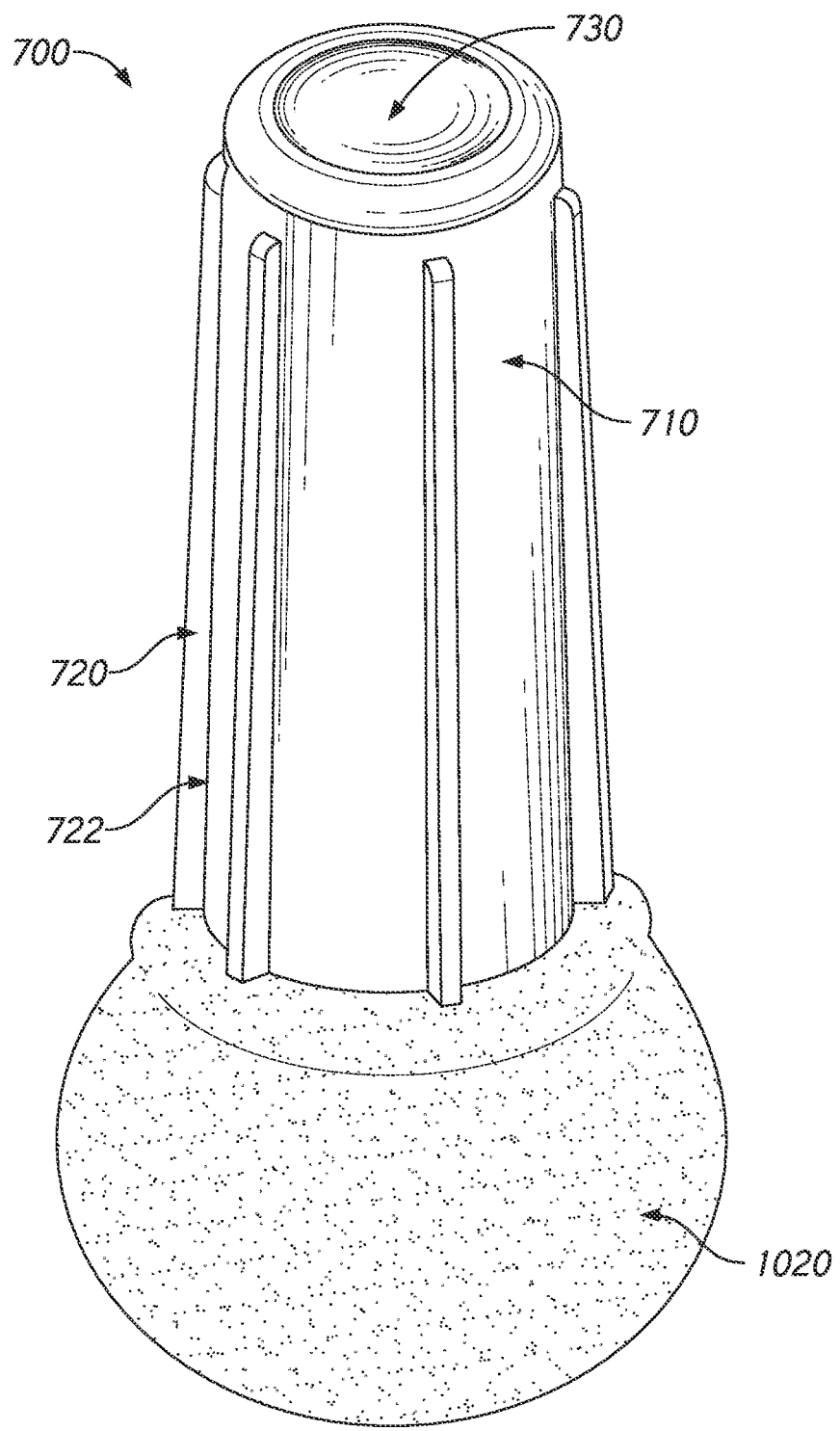
FIG. 10A is a front perspective view of an embodiment of an antiseptic cap.
Figure 12:
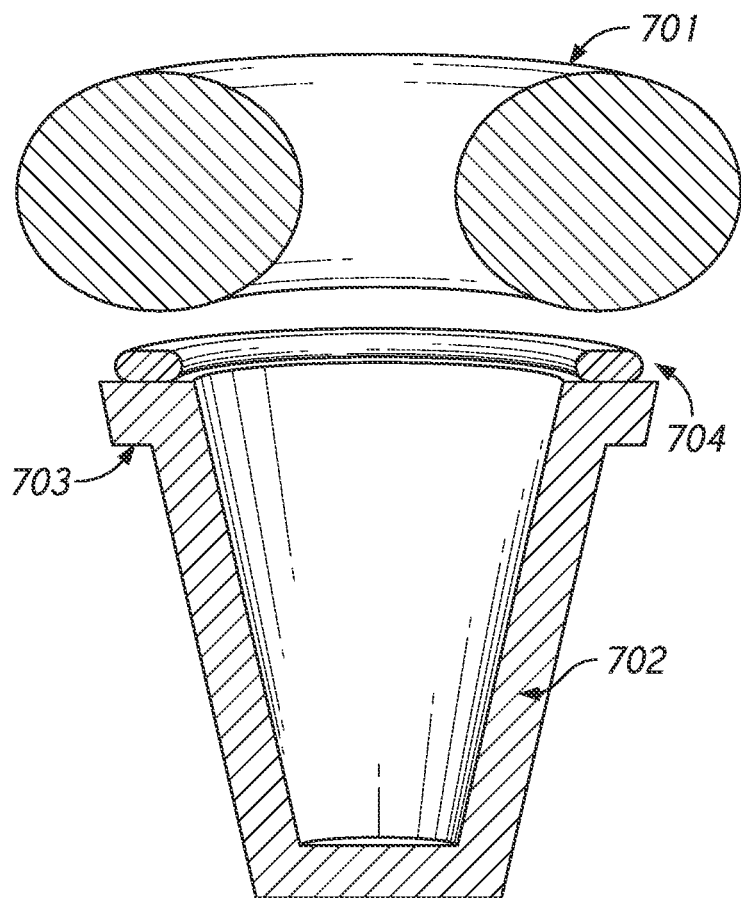
FIG. 12 is a side cross-sectional view of an example of a process of manufacturing an antiseptic cap.

FIGS. 10A-12 are various views of an antiseptic cap 700 including an absorbent material 1020, according to some embodiments. In particular, FIG. 10A is a front perspective view of an antiseptic cap 700 including an absorbent material 1020 and FIGS. 1B-10E are first side cross-sectional, second side cross-sectional, top, and bottom views of the antiseptic cap 700 of FIG. 10A, respectively. Furthermore, FIGS. 11A-11D are first side, top, second side, and side cross-sectional views of an embodiment of a process of manufacturing an antiseptic cap, respectively, and FIG. 12 is a side cross-sectional view of an embodiment of a process of manufacturing an antiseptic cap. Unless otherwise noted, reference numerals in FIGS. 10A-12 refer to components that are the same as or generally similar to the components in the remaining figures discussed herein. While the antiseptic caps 700 shown in FIGS. 10A-12 are similar to antiseptic cap 700 shown in FIGS. 7A-7E, it will be understood that the features described with reference to antiseptic cap 700 shown in FIGS. 10A-12 can be used with any of the embodiments described and/or contemplated herein. For example, any one of the antiseptic cap 82 of FIGS. 1A-1H, antiseptic cap 82 of FIG. 2, antiseptic cap 900 of FIGS. 3A-6, antiseptic cap 800 of FIGS. 8A-8C, and/or any additional caps disclosed herein can be modified to include an absorbent material 1020 positioned at least partially outside the antiseptic cap, as shown and described with reference to FIGS. 10A-12. It will also be understood that any feature, structure, material, step, or component of any embodiment described and/or illustrated herein can be used with or instead of any other feature, structure, material, step, or component of any embodiment of antiseptic cap 700 of FIGS. 10A-12.

Shown in FIG. 10A, and described in detail herein, is an embodiment of an assembly comprising a cap 700 including a base 710 with a connection region that is configured to connect with and/or to receive and/or to cover a corresponding connection region on a medical implement, such as a male protrusion (e.g., a male luer) of the medical implement. In some embodiments, the cap 700 can comprise a fluid-delivery material, such as an absorbent material 1020, attached to the base 710. For example, in some embodiments (as illustrated in FIGS. 10A-12), the absorbent material 1020 can be attached to a proximal end 702 of the base 710, such that the absorbent material 1020 is positioned at least partially or entirely outside of the base 710, and/or not within an interior region 787 of the base 710. As illustrated in the Figures, a male protrusion or luer may come in from the proximal end 702 of the cap 700 toward the distal end 704 of the cap 700 in order to couple with the cap 700.

As shown, the absorbent material 1020 can be attached to the proximal end 702 of the base 710. In some embodiments, as shown in FIGS. 10A-10E, an attachment between the absorbent material 1020 and the base 710 may not be located on an inside surface of the base 710. In some embodiments, the absorbent material 1020 may be coupled to an outer flange 725 of the cap 700. In some embodiments, the absorbent material 1020 can be attached via glue, undercuts, heat staking, and/or a friction fit, although any suitable attachment can be used. For example, in some embodiments, one or more edges or grooves of the absorbent material 1020 can interact with the outer surface of the base 710 and/or the outer flange 725 so that the absorbent material 1020 is held in a position at least partially outside the interior region 787 of the base 710.

In some embodiments, the base 710 is made of material that is rigid, or more rigid than the absorbent material 1020, or resilient, or flexible. The base material may be any suitable material, such as plastic (e.g., polypropylene), or any material that is suitable to cover a connection portion of a medical connector, or any material discussed herein that is resistant to microorganism growth. The fluid-delivery material or absorbent material 1020, as described herein, may be made of a material that can retain at least some liquid or gel against gravity in one or more different orientations. In some embodiments, the absorbent material 1020 is configured such that it does not lose any clinically significant amount of antiseptic during normal use during the time period of normal use in any orientation when the antiseptic is carried by the absorbent material 1020 and when the absorbent material 1020 is not in contact with another substance. In some embodiments, the fluid-delivery material, such as an absorbent material 1020, is a deformable or openable or otherwise movable material or mechanism such that when the cap 700 is coupled to a luer. The fluid-delivery material or absorbent material 1020 may compress or retract or otherwise move in response to the coupling of the cap 700 to a medical implement. The absorbent material 1020 may be sized and configured to snuggly contact or encompass or surround or envelop at least a portion of, or generally all of, the circumference of the connection region (e.g., a male protrusion or male luer). Upon coupling of the cap 700 to a medical implement, the absorbent material 1020 may be configured to wipe at least an outside surface of the connection region and apply an antiseptic or antimicrobial agent generally or substantially uniformly or evenly to the outside surface of the connection region.

As illustrated, the fluid-delivery material or absorbent material 1020 can stretch or expand (e.g., to increase the size of an opening in the fluid-delivery material) during coupling to receive a portion of the connector and/or to exert a force (e.g., a restoring force) against the portion of the connector to assist in providing tight, close, and/or constricting contact between the fluid-delivery material and the portion of the connector. In some embodiments, the absorbent material 1020, while compressing or retracting or otherwise moving in the coupling movement, releases antiseptic onto the connection region as it comes in contact with the connection region. In some embodiments, an absorbent material 1020 may be made of foam (e.g., such as a polyester or a polyurethane), gauze, sponge, or any other suitable material. The absorbent material 1020 can have any suitable form and/or configuration described herein. It will be understood that any feature, structure, material, step, or component of any embodiment described and/or illustrated herein (such as the antiseptic material 86 of antiseptic cap 82 of FIGS. 1A-1H) can be used with or instead of any other feature, structure, material, step, or component of any embodiment of antiseptic cap 700 of FIGS. 10A-12.

In some embodiments, the base 710 is harder or more rigid or less compressible than the absorbent material 1020. The absorbent material 1020 may have a larger cross-sectional width than at least a portion of the base 710. For example, the absorbent material 1020 may comprise a cross-sectional width larger than an outer flange 725 of the base 710 when the absorbent material 1020 is attached to the base 710. The base 710 may be composed of a material that is less permeable to fluid or liquid migration or transfer than the absorbent material 1020. As shown, in some embodiments, at least a portion of the absorbent material 1020 can extend further in the proximal direction than any portion of the base 710 before, after, and/or during use.

Figure 10B:
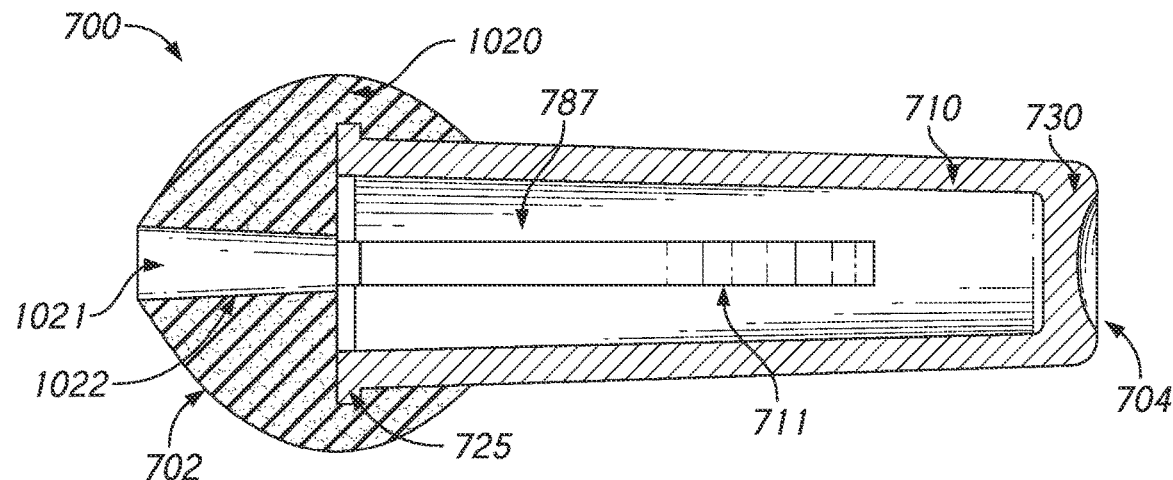
FIG. 10B is a side cross-sectional view of the antiseptic cap of FIG. 10A.
Figure 10C:
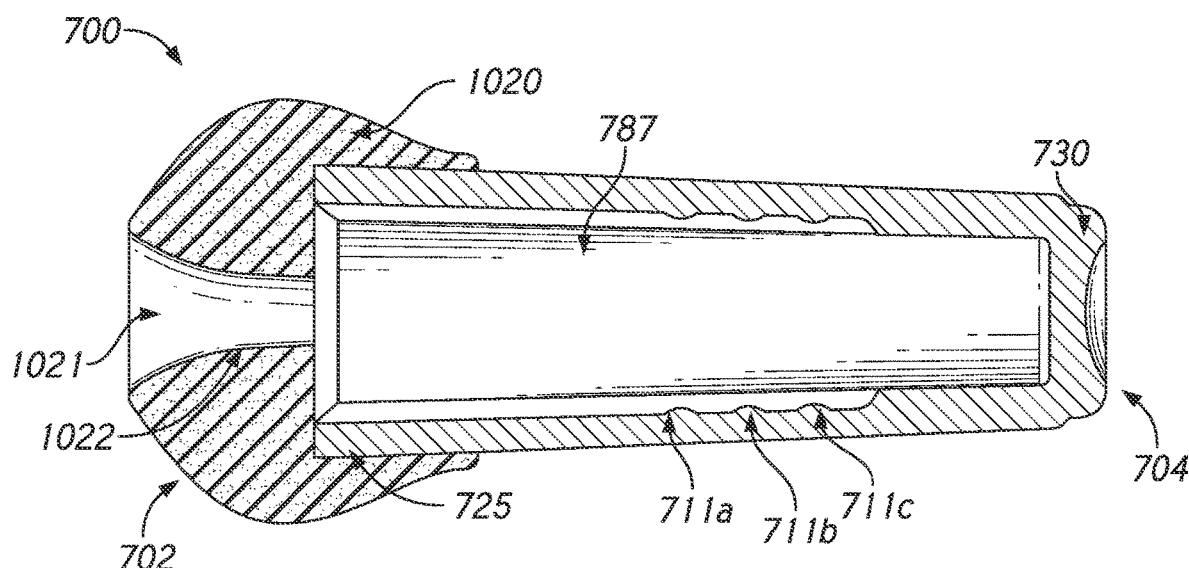
FIG. 10C is another side cross-sectional view of the antiseptic cap of FIG. 10A.
Figure 10D:
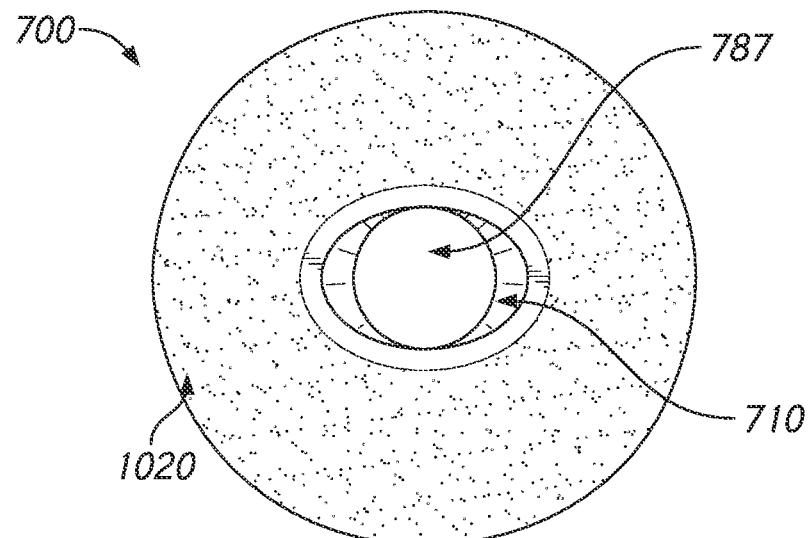
FIG. 10D is a top view of the antiseptic cap of FIG. 10A.
Figure 10E:
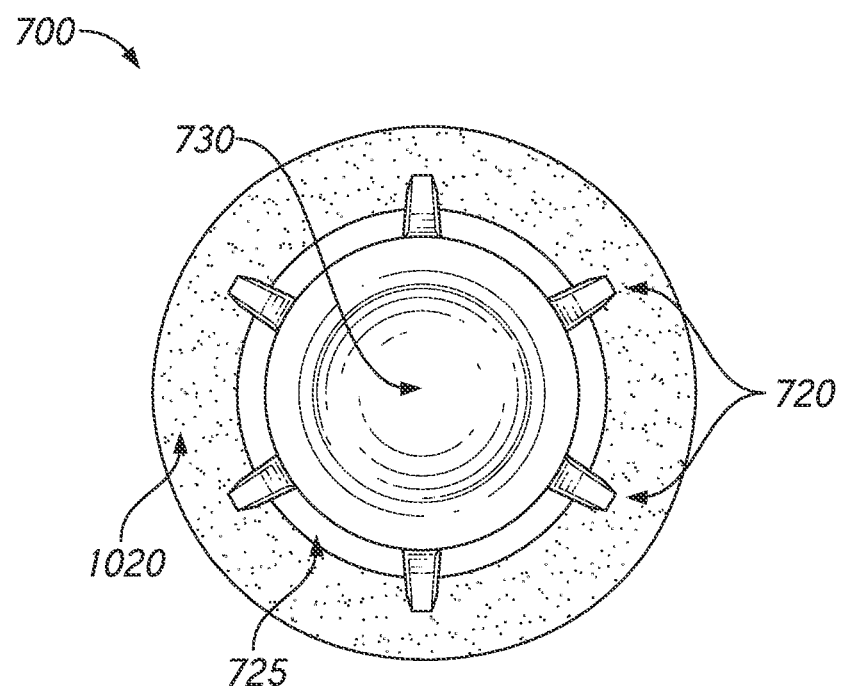
FIG. 10E is a rear view of the antiseptic cap of FIG. 10A.
Figure 11A:
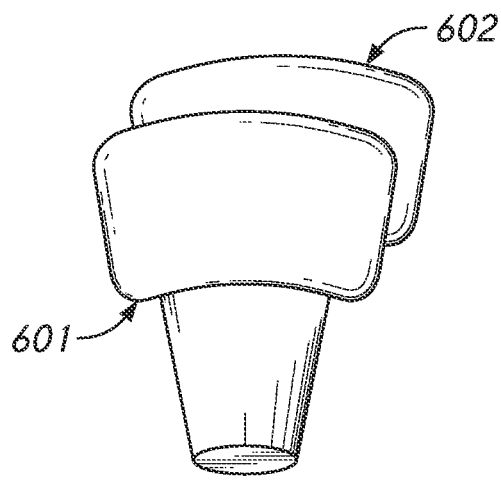
FIG. 11A is a side view of an example of a process of manufacturing an antiseptic cap.
Figure 11B:
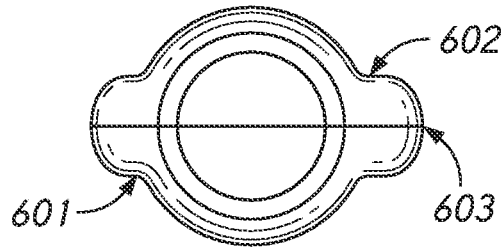
FIG. 11B is a top view of the process of manufacturing of FIG. 11A.
Figure 11C:
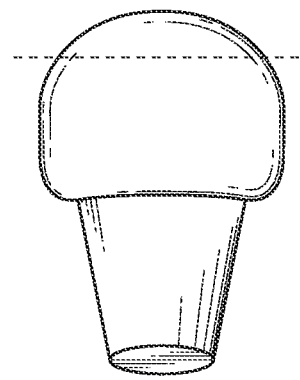
FIG. 11C is a side view of the process of manufacturing of FIG. 11A.
Figure 11D:
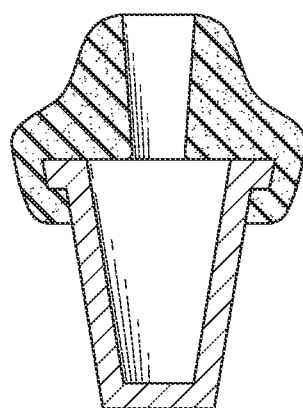
FIG. 11D is a side cross-sectional view of the process of manufacturing of FIG. 11A.

FIGS. 10B and 10C are side cross-sectional views of an embodiment taken along the coupling direction. As shown, in some embodiments, the absorbent material 1020 can be made of a deformable material and may include an opening 1021 with a hollow channel 1022 for coupling with a connection region (e.g., a male protrusion or luer). In some embodiments, the opening 1021 in the pre-use or stand-alone position may have a smaller diameter than the outer diameter of a coupling portion of a connection region (e.g., a male protrusion or male luer). In some embodiments, the hollow channel 1022 extends completely through the absorbent material 1020 so that a coupling luer may couple with the cap without puncturing the absorbent material 1020. In some embodiments, the hollow channel 1022 may not extend completely through the absorbent material 1020, and a coupling region may need to puncture the absorbent 1020 in order to couple, or the absorbent material 1020 may be pulled inside of the base 710.

FIGS. 11A-11D illustrate an example of a manufacturing process of the assembly 700. A plurality (e.g., two sheets, as shown) of portions of absorbent material 601 and 602 are placed about the base 710, generally in front of and behind the base 710. In some embodiments, one sheet that can wrap around the base 710 may be used. In some embodiments, more than two sheets may be used to surround the base 710. In some embodiments, the absorbent material 1020 may not be formed from a sheet. For example, in some embodiments, the absorbent material 1020 may be formed from a continuous filament or a series of filaments in close proximity, such as a tangle of filaments, or a mesh or a fabric.

Any suitable method may be used to attach any absorbent material 1020 of a cap 700 to a base 710 material of a cap 700, such as by attaching the absorbent material 1020 to a proximal 702 or upper outside surface of the cap 700. For example, in some embodiments, heat staking may be used to melt and seal at least a portion of the sheets 601 and 602 to each other and/or around a portion (e.g., an edge) of the perimeter of the upper or proximal portion 702 of the base 710 of the cap, such as in the embodiment shown in FIG. 11B. In some embodiments, an attachment agent, such as glue or solvent or adhesive, or any other suitable agent may be used instead of or in addition to heat staking. Shown in FIG. 1C, after the absorbent material 1020 is melted or glued onto or otherwise attached to the cap 700, a proximal end of the absorbent material 1020 is cut perpendicular to the coupling direction or otherwise modified to provide an opening 1021. In some embodiments, the resulting assembly has an opening 1021 in the absorbent material 1020 with a hollow channel 1022 for coupling with a connection region, such as a luer.

In some embodiments, as shown in FIG. 12, another or alternate process may be used in which a general torus shaped absorbent material 701 is glued or otherwise adhered to a cap 702 with an attachment agent 704. In some embodiments, the generally toroidal absorbent material 701 is melted onto the cap 702 with heat staking treatment. In some embodiments, the absorbent material 701 may not be toroidal and/or can be punctured by a portion of a medical implement (e.g., a luer) when the cap is coupled with the medical implement.

Delivery Systems

The present application includes a number of embodiments of delivery systems (e.g., syringes, strips, holders, sleeves, etc.) for an antiseptic cap. Though one or more Figures may show a delivery system with a particular embodiment of a cap, it shall be understood that any other caps or other medical devices disclosed herein can be used in and/or with any of the delivery systems in addition to or instead of the illustrated cap. For example, any one of the embodiments of the caps shown in FIGS. 1A-12 of the present application can be provided or used in connection with any of delivery system whether or not illustrated in such delivery system. By way of another example, embodiments of the caps described and/or contemplated within U.S. Provisional Patent Application No. 62/408,546 (herein referred to as the '546 application), U.S. Provisional Patent Application No. 62/420,359 (herein referred to as the '359 application), U.S. Provisional Patent Application No. 62/590,952 (herein referred to as the '952 application), U.S. Provisional Patent Application No. 62/526,847 (herein referred to as the '847 application), U.S. Provisional Patent Application No. 62/527,897 (herein referred to as the '897 application), U.S. Provisional Patent Application No. 62/571,157 (herein referred to as the '157 application), which are each incorporated by reference herein in their entireties, can be provided or used in connection with any of delivery system described herein, whether or not illustrated in such delivery system. It will be understood that any of the delivery systems described herein can be used or modified to be used with the various embodiments of a cap described and/or contemplated within the present application, '546 application, the '359 Application, the '952 Application, the '847 Application, the '897 Application, and the '157 application.

Antiseptic Cap Holder Assembly

Figure 13A:
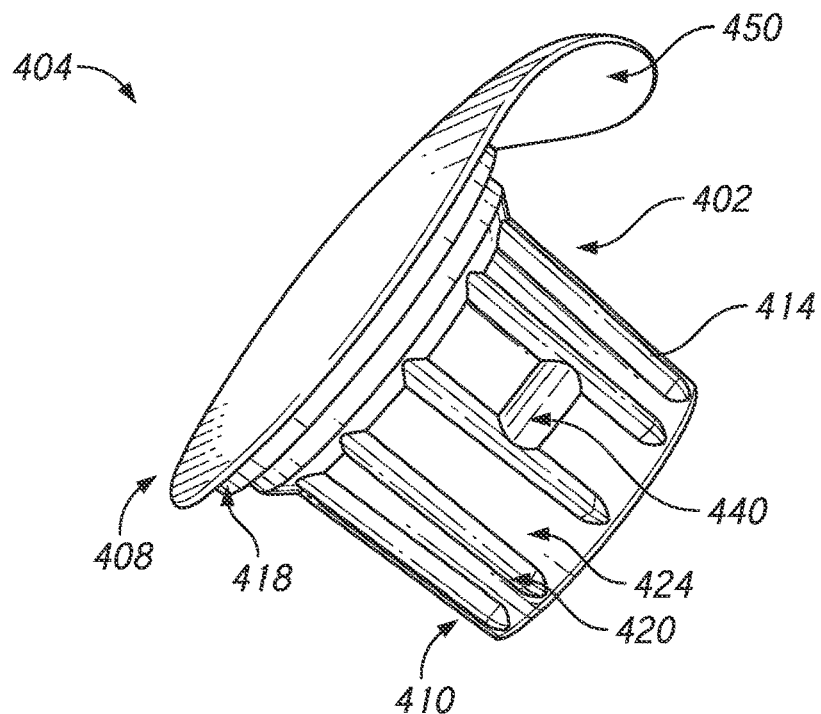
FIG. 13A is a front perspective view of an embodiment of an antiseptic cap holder assembly.
Figure 13B:
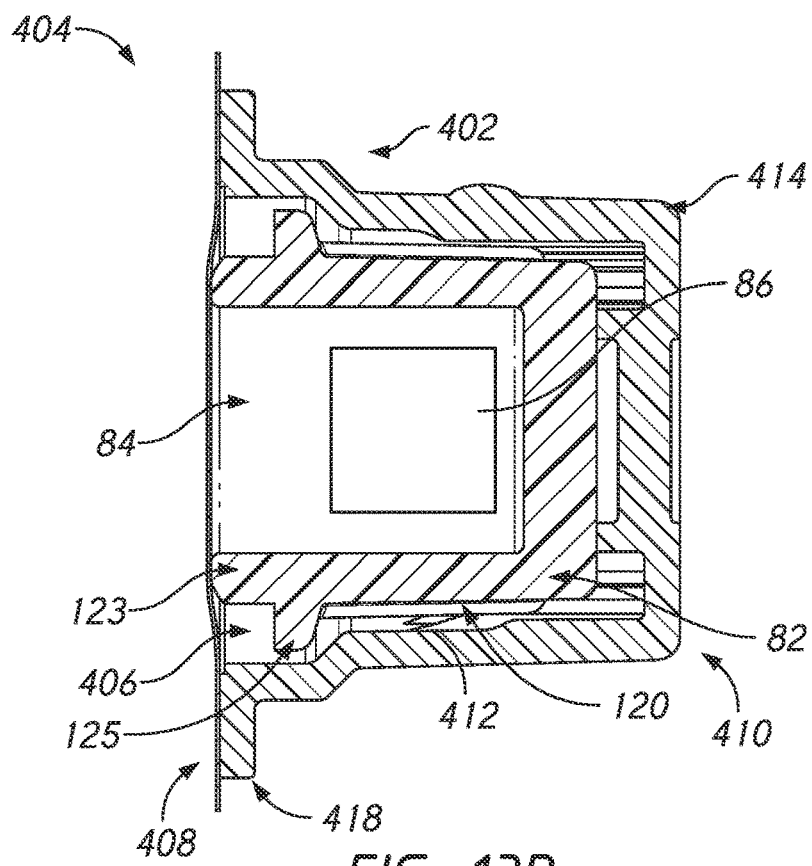
FIG. 13B is a side cross-sectional view of the antiseptic cap holder assembly of FIG. 13A.

FIGS. 13A and 13B are various views of an antiseptic cap holder assembly 404, according to some embodiments. In particular, FIG. 13A is a front perspective view of an antiseptic cap holder assembly 404, and FIG. 13B is a side cross-sectional view of the antiseptic cap holder assembly 404 of FIG. 13A. Unless otherwise noted, reference numerals in FIGS. 13A and 13B refer to components that are the same as or generally similar to the components in the remaining figures discussed herein. While the antiseptic cap 82 shown in FIGS. 13A and 13B are similar to antiseptic cap 82 shown in FIGS. 1A-1H, it will be understood that the features described with reference to the antiseptic cap holder assembly 404 shown in FIGS. 13A and 13B can be used with any antiseptic cap and/or cap assembly embodiments described and/or contemplated herein. For example, any one of the antiseptic cap 82 of FIG. 2, antiseptic cap 900 of FIGS. 3A-6, antiseptic cap 700 of FIGS. 7A-7E, antiseptic cap 800 of FIGS. 8A-8C, and/or any additional caps disclosed herein can be modified to function with the antiseptic cap holder assembly 404, as shown and described with reference to FIGS. 13A and 13B.

FIGS. 13A and 13B show an antiseptic cap holder assembly 404 having an antiseptic cap holder 402 and an antiseptic cap 82 positioned within the cap holder 402. The cap holder 402 includes a proximal end 408, a distal end 410, an inner wall surface 412, and an outer wall surface 414 defining a chamber 406. The cap holder 402, in some embodiments, can include an opening 416 into the chamber 406 and a radially outwardly extending flange 418 circumjacent the opening 416. As shown in FIG. 13A, the flange 418 may extend from the proximal end 408 of the cap holder 402. The cap holder 402 may include an optional bottom wall 419.

The cap holder 402, in some embodiments, prevents contamination of an antiseptic cap 82 within the cap holder 402. For example, a user may handle the antiseptic cap holder assembly 404 via one or more portions of the cap holder 402, such as the flange 418 extending out from the cap holder 402. The cap holder 402 may act as a guard against contact of the antiseptic cap 82 by a user.

The cap holder 402 can comprise any suitable material (e.g., rigid or semi-rigid material). In some embodiments, the cap holder 402 can comprise any suitable polymer. In some embodiments, the polymer may include a thermoplastic polymer, such as an aliphatic polymer or thermoplastic elastomer. For example, the cap holder 402 may comprise at least one of polypropylene and polyethylene (such as low, medium, or high density polyethylene). A semi-rigid material of the cap holder 402 can have any suitable durometer. For example, in some embodiments, the cap holder 402 can have a Shore A durometer in the range of approximately 60 to approximately 1050, although any suitable durometer can be used, such as, for example, about 50, about 55, about 60, about 65, about 70, about 75, about 80, about 85, about 90, about 95, about 100, among others (e.g., any durometer between about 50 and about 100). However, it will be understood that the cap holder 402 can have any durometer sufficient to house an antiseptic cap 82.

As shown in FIGS. 13A and 13B, the antiseptic cap holder assembly 404 may be sealed with a foil material or lid stock material 450, in some embodiments. The lid 450 may permit each antiseptic cap 82 within an antiseptic cap holder 402 to remain sterile. The lid 450 may be configured to attach to one or more portions of the antiseptic cap holder 402 and/or antiseptic cap 82. In some embodiments, the lid 450 can be sealed to the antiseptic cap holder 402. For example, the lid 450 may be attached to the flange 418 by any suitable method such as by adhesives or by conductive or inductive heat sealing techniques.

Additionally or alternatively, the lid 450 may be sealed to at least a portion of the antiseptic cap 82. Attachment directly to the antiseptic cap 82 permits the lid 450 to seal the first chamber 84 and prevent the removal of any antiseptic material 86 and/or antiseptic fluid within the antiseptic cap 82. In some embodiments, the lid 450 may form a double seal when the lid 450 is sealed against both the antiseptic cap holder 402 and the antiseptic cap 82 within the antiseptic cap holder 402. For example, a double seal may provide an extra barrier to prevent contamination of an antiseptic cap 82 and/or prevent an antiseptic material from escaping from the antiseptic cap 82. Providing a double seal may advantageously improve shelf life.

In some embodiments, the lid 450 may be thermally bonded to one or more of the antiseptic cap holder 402 and the antiseptic cap 82. Thermal bonding may occur using standard heat sealing technology, such as impulse, induction, conduction, radiant, or other heat sealing techniques. In some embodiments, the lid 450 could be attached to the antiseptic cap holder 402 and/or the antiseptic cap 82 by utilizing an adhesive bond or by a suitable mechanical or friction connection, such as a snap-fit.

The lid 450 could be made of any suitable material, such as foil, plastic, a laminate, etc. In one aspect, the lid 450 could be made of a foil material having a thickness of approximately 1 to 2 mil.

The antiseptic cap holder 402 and/or the antiseptic cap 82, in some instances, can comprise a structure, element or the like that prevents the relative rotation of the antiseptic cap holder 402 and the antiseptic cap 82. In some embodiments, the structure or element may facilitate attaching the antiseptic cap to a medical connector by engaging the antiseptic cap 82 and locking the antiseptic cap 82 in place to prevent rotation of the antiseptic cap 82 when positioned inside the antiseptic cap holder 402. For example, in some embodiments, the inner wall surface 412 of the antiseptic cap holder 402 may comprise internal ribs and/or internal slots. The internal ribs and/or internal slots may be configured to interact with the plurality of ribs 120 and/plurality of slots 122 of the antiseptic cap 82, is described herein with respect to FIGS. 1A-1H. These structures may prevent or resist the relative rotation of the antiseptic cap holder 402 with respect to the antiseptic cap 82. The term "ribs" referred to herein are structures that are raised or extend outward from a surface. The term "slots" refer to structures that extend below a surface or are positioned between two ribs and are at a lower level than the ribs. The ribs and/or slots can have any suitable form and/or configuration described herein. It will be understood that any feature, structure, material, step, or component of any embodiment described and/or illustrated herein (such as the plurality of ribs 120 and/plurality of slots 122 of the antiseptic cap 82 of FIGS. 1A-1H) can be used with or instead of any other feature, structure, material, step, or component of any embodiment of the antiseptic cap holder 402 of FIGS. 13A and 13B.

By way of another example, in some embodiments, the antiseptic cap holder 402 may have a feature or structure that forms an interference fit with the external surface of the antiseptic cap 82. In some embodiments, an inner surface 412 of the antiseptic cap holder 402 may have a feature or structure to form an interference fit with a portion of the antiseptic cap 82. Additionally or alternatively, the antiseptic cap 82 may have one or more features to form an interference fit with the antiseptic cap holder 402.

In some instances, as described in further detail below, the antiseptic cap holder 402 may contain a plurality of ribs and/or slots on the outer wall surface configured to prevent rotation of the antiseptic cap holder 402 relative to a syringe assembly, such as syringe assembly 1210 as shown and discussed in relation to FIGS. 20A and 20B. Any of the anti-rotation devices discussed herein to prevent the rotation may be utilized. For example, FIG. 13A shows an interlocking structure for preventing the relative rotation of the antiseptic cap holder 402, or the antiseptic cap holder assembly 404, with respect to a syringe assembly. In some instances, the outer wall surface 414 of the antiseptic cap holder 402 may include a plurality of circumferentially spaced and axially extending ribs 420 defining slots 424 between each pair of adjacent ribs. At least one of the plurality of ribs 420 and slots may be configured to interact with a corresponding feature on the syringe assembly. This interaction may prevent or resist the relative rotation of the antiseptic cap holder 402, or antiseptic cap holder assembly 404, with respect to the syringe assembly when the antiseptic cap holder 402, or the antiseptic cap holder assembly 404, is engaged with the syringe assembly.

It is contemplated that the antiseptic cap holder assembly 404 need not be coupled or combined with a syringe assembly. As shown in FIGS. 13A and 13B, a stand-alone antiseptic cap holder assembly 404 may incorporate circumferentially spaced ribs 420 for grasping by the hand of a user of the antiseptic cap holder assembly 404. The antiseptic cap holder assembly 404 can be used for the same purposes as described herein but may be used by hand.

FIG. 13A shows that, in some embodiments, the antiseptic cap holder 402, or the antiseptic cap holder assembly 404, can include a structure, element or the like that resists the relative axial movement of these parts when the antiseptic cap holder 402 or the antiseptic cap holder assembly 404 is positioned fully within a syringe assembly, as discussed in further detail herein. For example, the antiseptic cap holder 402 can have an annular protuberance 440 on the outer wall surface 414 of the antiseptic cap holder 402 that is dimensioned to fit within a corresponding groove on a syringe assembly.

The antiseptic caps and/or antiseptic cap holder assemblies disclosed herein may be distributed and/or packaged in various suitable methods. Suitable methods include, but are not limited to, individual packages, a pouch package containing a plurality of antiseptic cap holder assemblies (such as a dispensing bag discussed herein with reference to FIGS. 14-18), a strip package (discussed herein with reference to FIGS. 19A-19D), or a syringe assembly wherein the antiseptic cap holder assemblies is attached to a syringe (discussed herein with reference to FIGS. 20A and 20B). It will be appreciated that the distribution and/or packaging method, as well as the relative sizes, of the antiseptic caps and/or antiseptic cap holder assembly disclosed herein are exemplary and non-limiting. Indeed, it will be understood, that the packaging can be modified for any suitable embodiment, and that relative methods can differ in various embodiments.

Dispensing Bag

Figure 14:
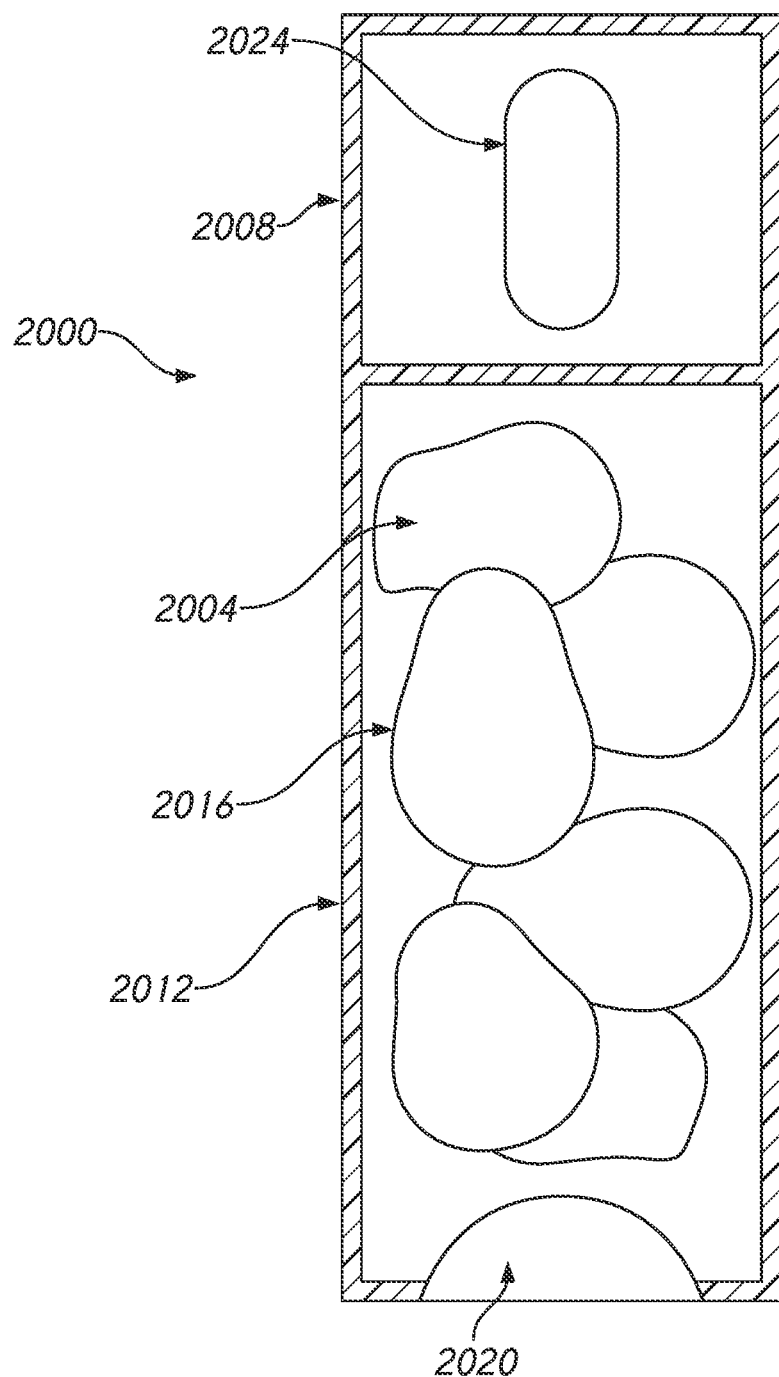
FIG. 14 is a front view of an embodiment of a dispensing bag for antiseptic cap holder assemblies.
Figure 15:
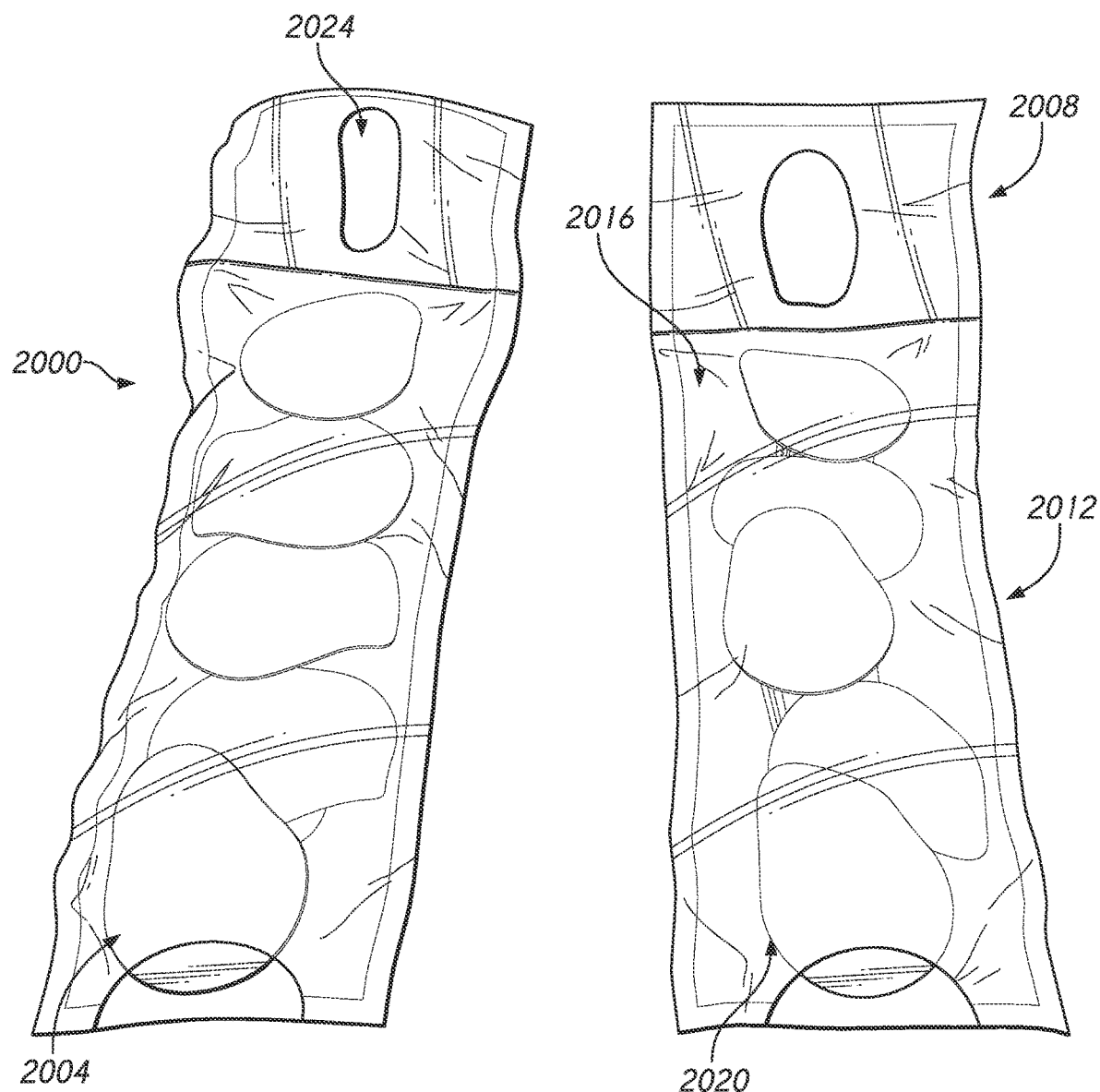
FIG. 15 is a front perspective view of multiple dispensing bags of FIG. 14.
Figure 16A:
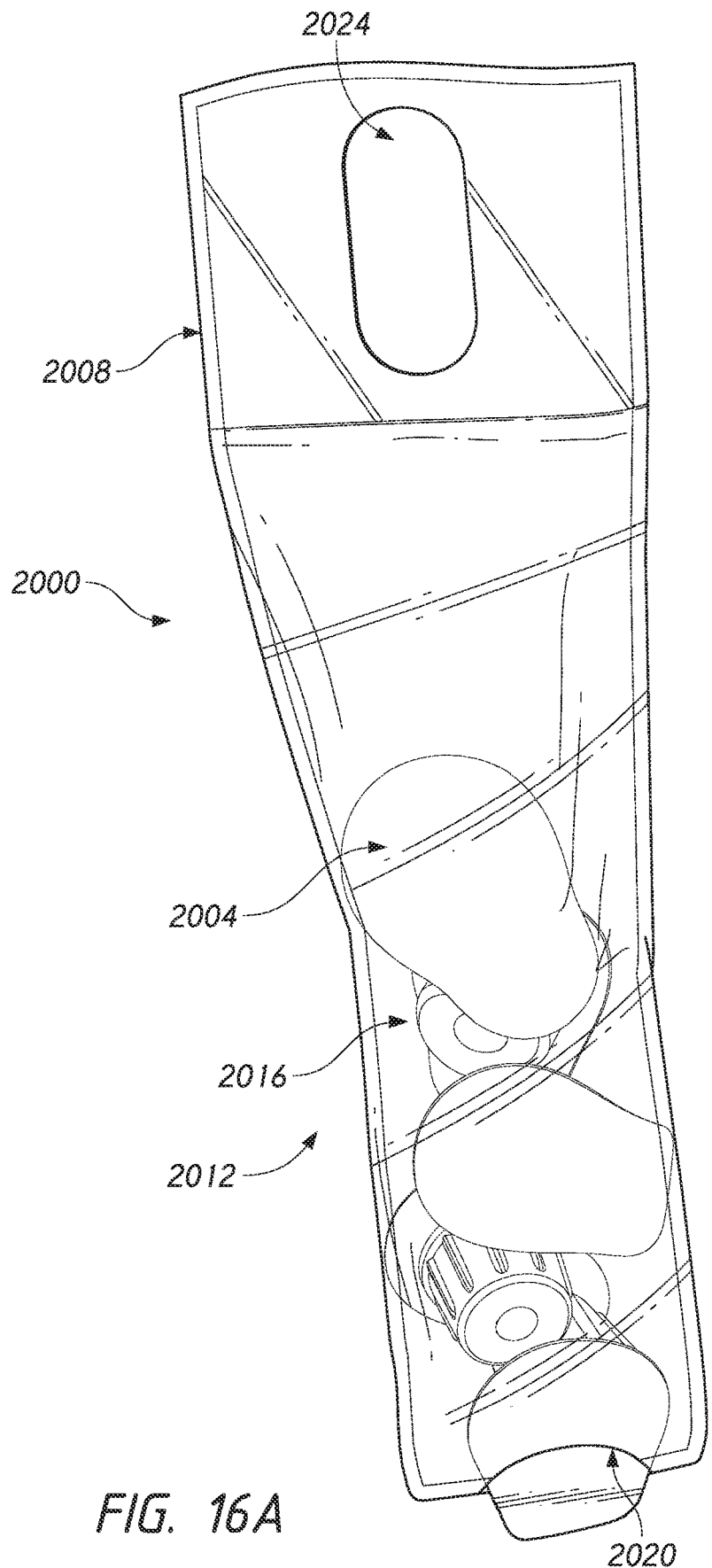
FIG. 16A is a front view of the dispensing bag of FIG. 14.
Figure 16B:
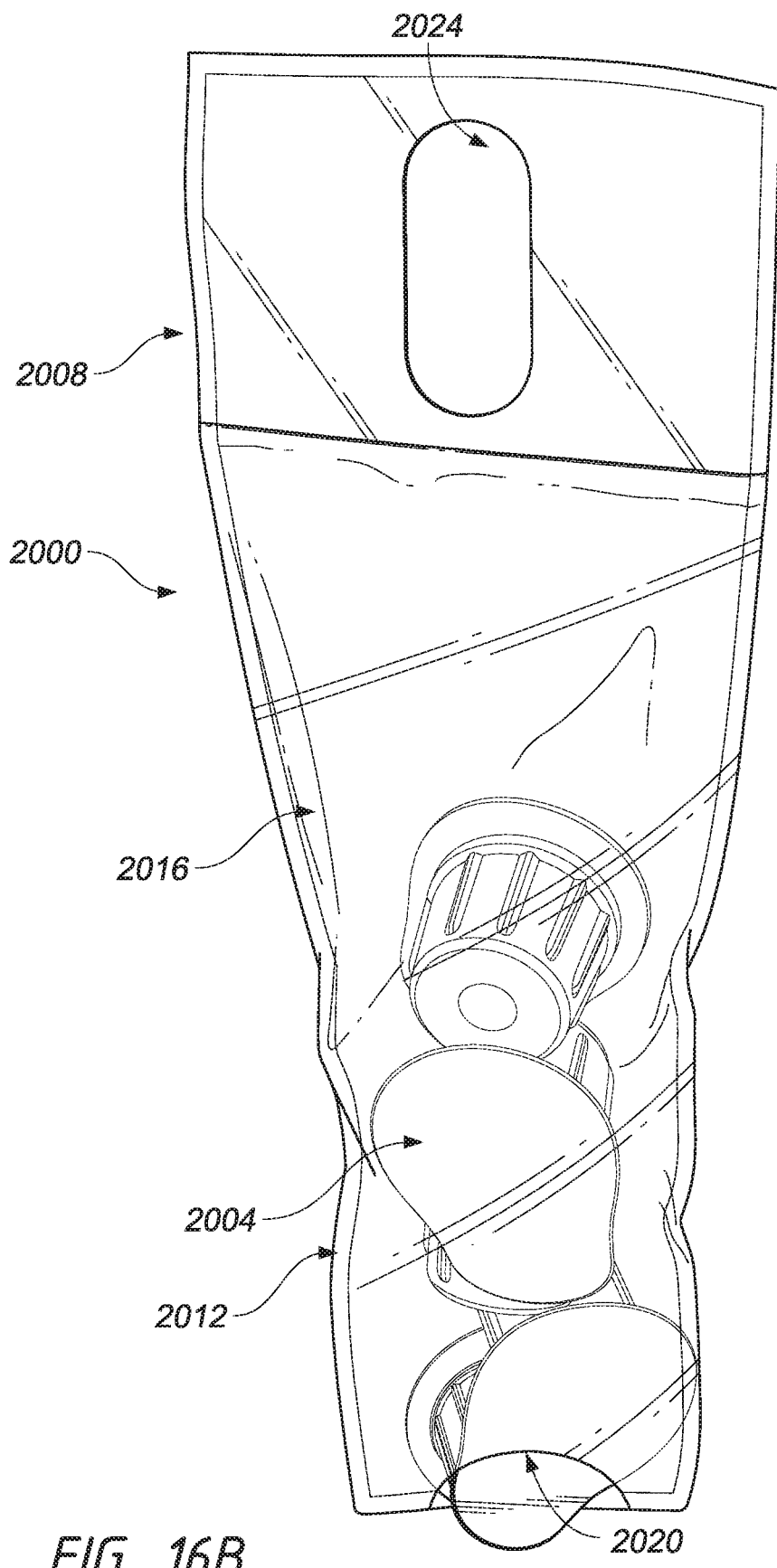
FIG. 16B is a rear view of the dispensing bag of FIG. 14.
Figure 17A:
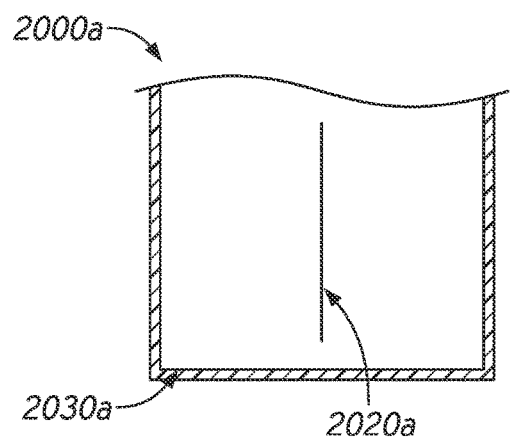
FIG. 17A is a partial front view of an embodiment of a dispensing bag for antiseptic cap holder assemblies.
Figure 17B:
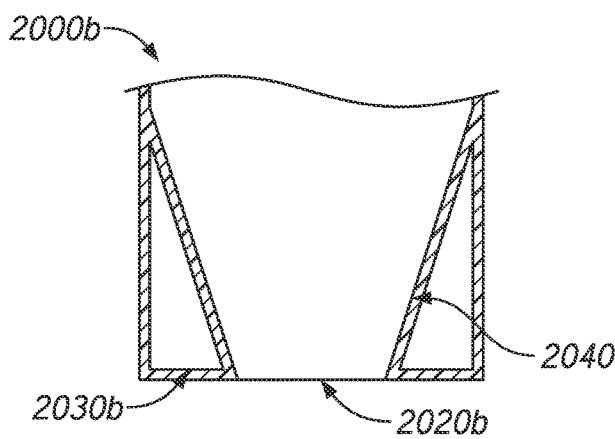
FIG. 17B is a partial front view of an embodiment of a dispensing bag for antiseptic cap holder assemblies.
Figure 17C:
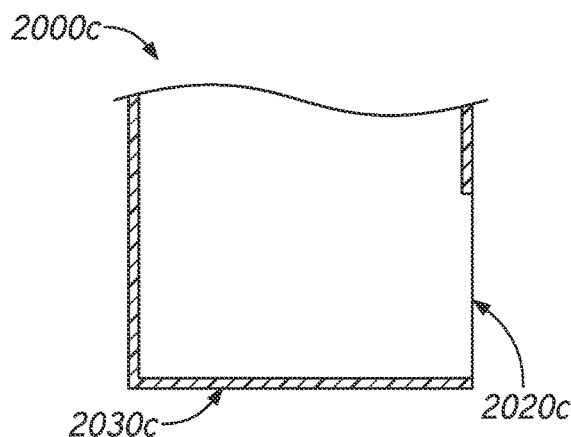
FIG. 17C is a partial front view of an embodiment of a dispensing bag for antiseptic cap holder assemblies.
Figure 18:
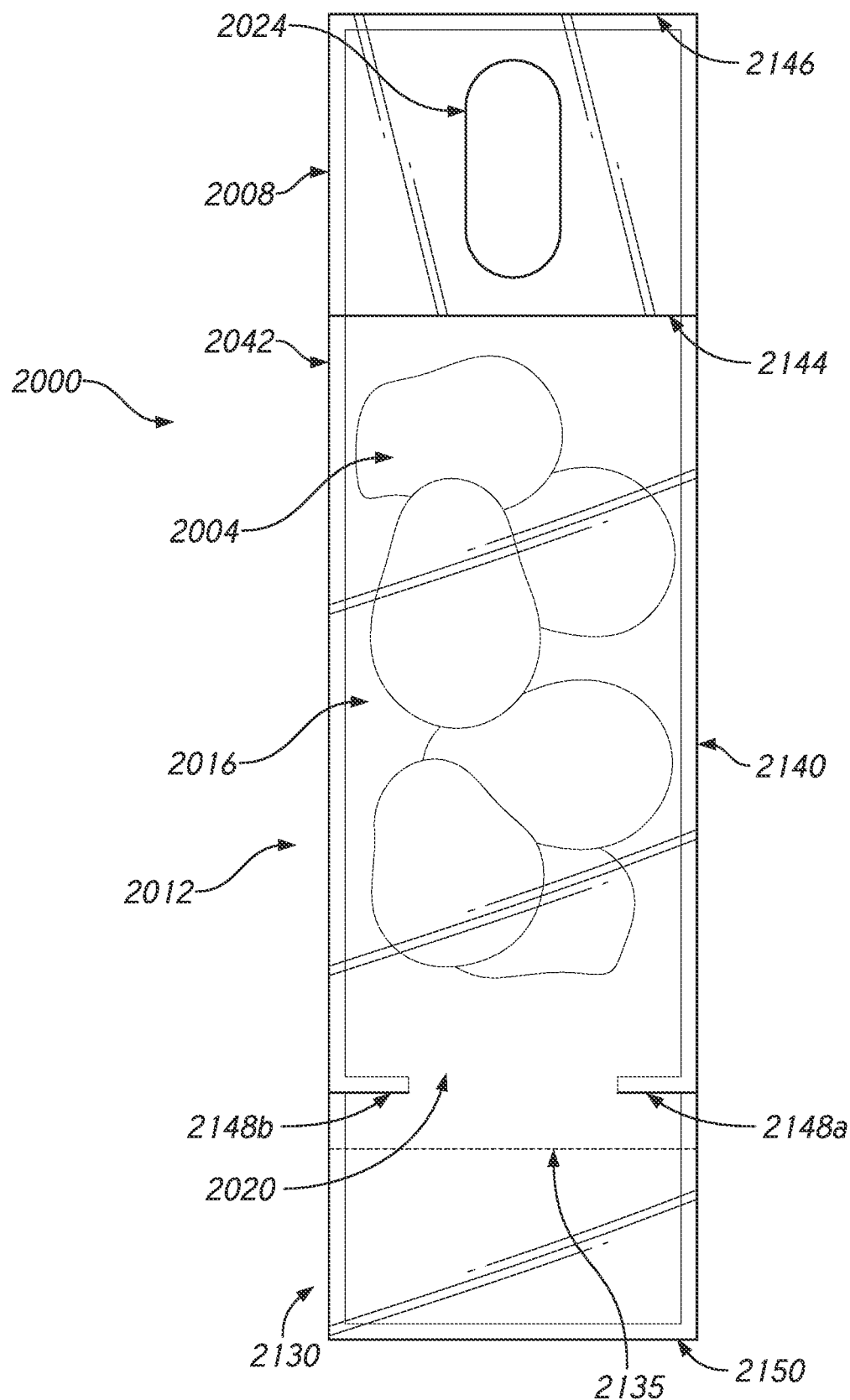
FIG. 18 is a front view of an embodiment of a dispensing bag for antiseptic cap holder assemblies.

FIGS. 14-18 are various views of a delivery system for medical articles in the form of examples of a dispensing bag 2000 for antiseptic caps and/or antiseptic cap holder assemblies 2004, according to some embodiments. In particular, FIG. 14 is a front view of a dispensing bag 2000 including one or more an antiseptic cap assemblies 1220, and FIGS. 15, 16A, and 16B are front perspective, front, and rear views of multiple dispensing bags 2000 of FIG. 14, respectively. FIGS. 17A-17C are front views of various embodiments of dispensing bags 2000a-2000c for antiseptic caps and/or antiseptic cap holder assemblies 2004. FIG. 18 is a front view of a dispensing bag 2100 for antiseptic caps and/or antiseptic cap holder assemblies 2004. Unless otherwise noted, reference numerals in FIGS. 14-18 refer to components that are the same as or generally similar to the components in the remaining figures discussed herein. While the antiseptic cap holder assembly 2004 shown in FIGS. 14-18 are similar to antiseptic cap holder assembly 404 shown in FIGS. 13A and 13B, it will be understood that the features described with reference to the dispensing bag shown in FIGS. 14-18 can be used with any antiseptic cap and/or cap assembly embodiments described and/or contemplated herein. For example, any one of the antiseptic cap 82 of FIGS. 1A-1H, antiseptic cap 82 of FIG. 2, antiseptic cap 900 of FIGS. 3A-6, antiseptic cap 700 of FIGS. 7A-7E, antiseptic cap 800 of FIGS. 8A-8C, and/or any additional caps disclosed herein can be modified to function with the dispensing bag, as shown and described with reference to FIGS. 14-18.

In any embodiments, as shown, a delivery system can comprise a generally elongate portion comprising a tube or sheath region with an interior cavity having an interior width or diameter that corresponds to the outer width or diameter of each of a plurality of medical articles to be contained within and dispensed from the delivery system. For example, the interior width or diameter of the elongate portion of the delivery system can be about the same as or slightly larger than the outer width or diameter of each of the plurality of medical articles to permit the plurality of medical articles to be contained loosely within the elongate portion, thereby enabling the plurality of medical articles to shift and/or move within the tube or sheath without being affixed or engaged with each other or with the tube or sheath. For example, in some embodiments, the interior of the elongate portion is shaped and composed such that the plurality of medical articles can automatically form a single vertical column of medical articles in the elongate portion as individual units of the medical articles are inserted or loaded into a proximal opening of the delivery system. The loose containment can permit a column of medical articles positioned within the tube or sheath to move toward a dispensing region of the delivery system (e.g., a constriction or a reduced-width region) as medical articles are removed through a distal dispensing region in multiples or singly (one at a time).

The interior width or diameter of the elongate portion of the delivery system can be sufficiently small so that it does not permit more than one full medical article to occupy the same level (e.g., a vertical level) within the elongate portion of the delivery system at the same time, thereby resisting clogging or other obstruction of the elongate portion by interference among the contained medical articles. The interior wall or walls of the elongate portion can have a coefficient of friction that is sufficiently low (or slippery) to permit reliable and consistent migration of the loose medical articles through the delivery system during use (such as when being pushed or pulled by a user through the delivery system), and/or that is sufficiently high (or slide resistant) to create an inertial position for each medical article during containment within the elongate portion to resist free-sliding and bunching up of the medical articles contained in the delivery system. The wall or walls of the elongate portion can be flexible and/or collapsible such that an irregular, non-smooth surface topography is produced along the interior wall or walls (e.g., comprising wrinkles or creases) in normal use when the elongate portion contains medical articles, in order to produce a low-level of resistance to rapid sliding of the medical articles through the tube or sheath when not being pushed or pulled out of the delivery system by a user.

The dispensing bag 2000, as shown in FIGS. 14-16b, may function as a delivery system to contain one or more disinfectant devices, or at least a portion of one or more disinfectant devices, such as, for example, antiseptic caps or antiseptic cap holders assembly 2004. Any reference in this specification to the use or containment of an antiseptic cap holder assembly 2004 of any type should also be interpreted to include the use, in addition or in the alternative, of an antiseptic cap. In some embodiments, the dispensing bag 2000 facilitates access to an antiseptic cap holder assembly 2004 by advantageously allowing for removal of a single antiseptic cap holder assembly 2004 at a time, while maintaining one or more other antiseptic cap holder assemblies 2004 within the dispensing bag 2000.

Each of the cap holder assemblies 2004 may include any antiseptic cap holder and an antiseptic cap described herein. While the figures illustrate the dispensing bag 2000 housing five antiseptic cap holder assemblies 2004, it will be understood that any number of disinfectant filled devices can be packaged within a dispensing bag 2000. It will also be understood that any of the embodiments of the dispensing bag 2000 described and/or contemplated herein can be modified to be used with any antiseptic cap described and/or contemplated herein or within the '546 application, the '359 Application, the '952 Application, the '847 Application, the '897 Application, and the '157 application.

In some embodiments, as shown in FIGS. 14-16B, the dispensing bag 2000 has a proximal portion 2008 and a distal portion 2012. The distal portion 2012 may comprise a chamber 2016 sized and configured to contain one or more antiseptic cap holder assemblies 2004. For example, in some embodiments, the distal portion 2012 comprises one more sealed edges extending along the perimeter of the distal portion 2012 to form an interior surface of the chamber 2016. In some embodiments, the interior surface can have any suitable surface texture, such as, for example, smooth and/or rough.

The chamber 2016 can comprise any suitable shape and/or configuration capable of receiving at least a portion an antiseptic cap hold assembly 2004. For example, as shown in FIGS. 14-16B, the chamber 2016 can comprise a generally cylindrical shape, although it will be appreciated that the chambers 2016 can comprise any suitable wall structure (e.g., straight and/or curved) and have any suitable shape (e.g., cylindrical, tapered, conical).

A width of the chamber 2016, as shown in FIG. 14-16B, may be larger than a width of the outer surface of the antiseptic cap holder assembly 2004 to facilitate containing the antiseptic cap holder assembly 2004. In some embodiments, the width of the chamber 2016 may remain constant throughout the chamber 2016. In some embodiments, the width of the chamber 2016 may vary along the length of the chamber. For example, the chamber 2016 can comprise a portion having a narrowed width as the chamber 2016. In some embodiments, the narrowed width may be located adjacent to a distal end of the dispensing bag 2000 to facilitate the removal of a single antiseptic cap holder assembly 2004 at a time.

A length of the chamber 2016 may be sufficiently long to house a plurality of antiseptic cap holder assemblies 2016 and prevent accidental or incidental removal of the antiseptic cap holder assemblies 2016 from the chamber 2016.

In some embodiments, the interior surface of the dispensing bag 2000 may be attached to one or more of the antiseptic cap holder assemblies 2004 contained within the chamber 2016. The attachment may utilize an adhesive bond or by a suitable mechanical or friction connection, such as a snap-fit.

In some embodiments, as illustrated in FIGS. 14-16B, the dispensing bag 2000 may comprise one or more openings 2020. The opening 2020 may allow a user to remove one or more antiseptic cap holder assemblies 2004 from the chamber 2016. For example, the opening 2020 provides access to the antiseptic cap holder assembly 2004, while still allowing the dispensing bag 2000 to retain any remaining antiseptic cap holder assemblies 2004 within the chamber 2016.

As shown in FIGS. 16A and 16B, in some embodiments, the opening 2020 may be located at a distal end of the dispensing bag 2000. The opening 2020 may form a constriction such as by extending across only a portion of the distal end. For example, as shown in FIGS. 14-16B, the opening 2020 may not extend along the entire length of the distal end of the dispensing bag 2000 (for example, as shown in FIG. 17B discussed herein). In some embodiments, the width of the opening 2020 can be smaller than the outer width or diameter of the medical article, such as the antiseptic cap holder assembly 2004 or cap, that is contained within the delivery system to resist freely dropping out medical articles through the opening 2020 when not being pushed or pulled by a user. In some embodiments, the width of the opening 2020 can be smaller than the outer width or diameter of the medical article, but sufficient largely that it can temporarily resiliently or flexibly increase in size to permit the medical article to pass through the opening 2020 without tearing or irreversibly stretching or otherwise damaging the material of which the opening 2020 is made. Placement of the opening 2020 at the distal end advantageously allows for the antiseptic cap holder assembly 2004 to naturally be placed adjacent to, or partially extending through, the opening 2020 when the dispensing bag 2000 is hung (as described in further detail below). In this manner, the location of the opening 2020 may facilitate access to the antiseptic cap holder assembly 2004. However, it will be understood, that the location can be modified for any suitable embodiment.

The opening 2020 can comprise any suitable shape and/or configuration capable of permitting access to, while resisting accidental removal of, an antiseptic cap holder assembly 2004 from within the chamber 2016. For example, FIGS. 17A-17C show partial front views of various embodiments of dispensing bags 2000a-2000c for antiseptic caps and/or antiseptic cap holder assemblies 2004.

As shown in FIG. 17A, in some embodiments, an opening can comprise one or more slits 2020a. The dispensing bag 2000c may comprise a completely sealed distal edge 2030a and the slit 2020a may formed along a sidewall and extend into the chamber 2016 of the dispensing bag 2000a. A user may utilize the slit 2020a to gain access to one or more antiseptic cap holder assemblies 2004 within the chamber 2016. In some embodiments, the slit 2020a may be predisposed in a closed position to prevent the unintended removal of the antiseptic cap holder assembly 2004 from the dispensing bag 2000a.

FIG. 17B shows that, in some embodiments, an opening 2020b can comprise a diameter smaller than a diameter of the outer surface of the antiseptic cap holder assembly 2004 to prevent the unintended removal of the antiseptic cap holder assembly 2004 from the delivery system or to permit only a portion of the antiseptic cap holder assembly 2004 to extend outside of the chamber 2016 while the rest of the antiseptic cap holder assembly 2004 remains contained inside of the delivery system until it is intentionally removed. For example, the opening 2020b may include one or more sealed edges 2040 within the chamber 2016 and/or one or more sealed edges 2030b at a distal end of the dispensing bag 2000. The one or more sealed edges 2040, 2030b may taper towards the opening 2020b. The one or more sealed edges 2040, 2030b may advantageously permit only one antiseptic cap holder assembly 2004 to extend through the opening 2020b. The one or more sealed edges 2040, 2030b can comprise any suitable shape and/or configuration capable of receiving at least a portion an antiseptic cap hold assembly 2004. For example, as shown in FIG. 17B, the sealed edge 2040 can comprise a generally conical shape, although it will be appreciated that the sealed edge 2040 can comprise any suitable wall structure (e.g., straight and/or curved) and have any suitable shape (e.g., cylindrical, tapered).

As shown in FIG. 17C, in some embodiments, an opening 2020c may be located on along a side edge of the dispensing bag 2000. For example, a dispensing bag 2000c may comprise a completely sealed distal edge 2030c. The sealed distal edge 2030c may advantageously prevent the unintended removal of the antiseptic cap holder assembly 2004 from the delivery system caused by a downward gravitational force alone (e.g., when the dispensing bag is in a vertically hanging position).

In embodiments in which a portion of the antiseptic cap holder assembly 2004 protrudes beyond the opening 2020, a user may remove the antiseptic cap holder assembly 2004 from the dispensing bag 2000. In some embodiments, the opening 2020 may have a diameter the same size as or greater than the antiseptic cap holder assembly 2004. It will be appreciated that location of the opening 2020, as well as the relative size, indicated in FIGS. 37-38B is exemplary and non-limiting. Indeed, it will be understood, that the relative size can be modified for any suitable embodiment, and that the relative proportions of the opening 2020 in relation to the remainder of the dispensing bag 2000 can differ in various embodiments. In some embodiments, the dispensing bag 2000 may not incorporate one or more openings 2020.

To remove the antiseptic cap holder assembly 2004 from the dispensing bag 2000, a user may grasp a portion of the antiseptic cap holder assembly 2004 that is positioned within the bag 200, or that is protruding beyond the opening 2020, and apply a removal force, such as a downward force (if the dispensing bag 2000 is positioned in a vertically hanging orientation). In some embodiments, a user may push the antiseptic cap holder assembly 2004 out through the opening 2020 by grasping at least a portion of the dispensing bag 2000 and applying a pinching force or other force to the antiseptic cap holder assembly 2004 through the dispensing bag 200 to advance the antiseptic cap holder assembly 2004 through the opening 2020. In some embodiments, the dispensing bag 2000 may advantageously eliminate the need for direct contact with the antiseptic cap holder assembly 2004 during removal from the dispensing bag 2000. In some embodiments, the dispensing bag 2000 facilitates removal of the antiseptic cap holder assembly 2004 through an efficient process that only requires the use of a single hand.

The antiseptic cap holder assembly 2004 may be withdrawn from the dispensing bag 2000 such that the removal (e.g., downward) force required to withdraw the antiseptic cap holder assembly 2004 from the chamber 2016 is greater than the force of gravity on the leading (distalmost) antiseptic cap holder assembly 2004 located within or partially within the dispensing bag, such that the antiseptic cap holder assembly 2004 does not drop through the hole 2024 merely under the force of gravity.

To prevent accidental removal of the antiseptic cap holder assembly 2004 from the dispensing bag 2000, in some embodiments, the dispensing bag 2000 can comprise a semi-rigid or resilient or elastomeric material capable of deformation when a force is applied. As the antiseptic cap holder assembly 2004 is being removed from the chamber 2016, the opening 2020 can be configured to deform radially outward or in an opening direction that is generally perpendicular to the longitudinal axis of the dispensing bag 200 in one or more locations where the antiseptic cap holder assembly 2004 contacts or otherwise interacts with the opening 2020. In some embodiments, the opening 2020 can be configured to rebound radially inward in a closing direction, generally opposite from the opening direction, after the antiseptic cap holder assembly 2004 is removed from the dispensing bag 2000 through the opening 2020. This may advantageously allow the opening 2020 of the dispensing bag 2000 to temporarily and/or permanently deform when the opening 2020 interacts with one or more features of the antiseptic cap holder assembly 2004. In some embodiments, the ability of the opening 2020 to deform can permit the antiseptic cap holder assembly 2004 to be removably contained within the chamber 2016. In some embodiments, the distal opening 2020 is smaller than a proximal opening in the dispensing bag, which can permit the rapid loading of multiple antiseptic cap holder assemblies 2004 through the proximal opening in quick succession during manufacturing, while resisting the unintentionally unloading of the contained antiseptic cap holder assemblies 2004 out of the distal opening 2020.

The dispensing bag 2000, in some embodiments, may comprise one or more features configured to allow the user to create an opening 2020 and gain access to one or more antiseptic cap holder assemblies 2004 within the chamber 2016. FIG. 18 shows an embodiment of the dispensing bag 2000 having a sealing portion 2130 located distal to an opening 2020. In some embodiments, the sealing portion 2130 may include a sealed distal edge 2150 and at least a portion of a sealed side edge 2140. The sealed side edge 2140 may include at least a portion of the chamber 2016. The sealing portion 2130 may be removably detached from the dispensing bag 2000. In some embodiments, the dispensing bag 2000 may comprise contain notches and/or perforations and/or scores 2135 to allow a user to tear or open or otherwise remove the sealing portion 2130 of the dispensing bag 2000 and form or access the opening 2020. Upon removal of the sealing portion 2130, the dispensing bag 2000 may include one or more sealed distal edges 2148a, 2148b defining the opening 2020. The opening 2020 may include any features described herein.

In some embodiments, the dispensing bag 2000 may be manufactured utilizing one or more steps described herein. A plurality of sheets of material, such as two sheets, may be placed in alignment to provide the faces of the dispensing bag 2000. For example, a first sheet may be placed on top of a second sheet with both sheets being generally the same size and shape. In some embodiments, the sheets may be rectangular; however, the sheets may comprise any shape suitable to form the dispensing bag 2000. One or more edges or other regions of the sheets may be bonded or sealed to provide the chamber 2016 of the dispensing bag 2000. Any suitable method may be used to bond or seal the one or more edges or other regions. For example, in some embodiments, heat staking and/or thermal bonding may be used to melt and seal at least a portion of the sheets to each other and/or around a portion (e.g., an edge) of a perimeter of the chamber 2016. Thermal bonding may be performed using standard heat sealing technology, such as impulse, induction, conduction, radiant, or other heat sealing techniques. Additionally or alternatively, the edges may be sealed by utilizing sonic welding, an adhesive bond, or by any suitable mechanical or friction connection, such as a snap-fit. In some embodiments, an attachment agent, such as glue or solvent or adhesive, or any other suitable agent may be used. With reference to FIG. 18, for example, the side edges 2140, 2142 may be sealed along with one or more edges 2144, 2146 located in the proximal portion 2008. In some embodiments, the resulting assembly has an opening 2020 in the distal portion 2012 with a hollow chamber 2016 for retaining antiseptic cap holder assemblies 2004. The one or more antiseptic cap holder assemblies 2004 may be placed within the chamber 2016 through any suitable methods. The opening 2020 may be formed by forming edges 2148a, 2148b through any sealing method described herein. In some embodiments where the dispensing bag 2000 comprises the sealing portion 2130, the distal end 2150 can be sealed and the notches, perforations, and/or scores 2135 may be formed along the width of the dispensing bag 2000.

The proximal portion 2008 of the dispensing bag 2000 can include one or more hanging holes 2024, in some embodiments. For example, the hole 2024 may include a die cut hole or holes. The hole 2024 can be sized and configured to allow the dispensing bag 2000 to be hung on a convenient hanger. For example, a user may utilize the one or more holes 2024 to hang the dispensing bag 2000 on an IV pole. The hole 2024 can comprise any suitable shape and/or configuration capable of allowing the dispensing bag 2000 to be hung on a hanger. The location of the hole 2024, as well as the relative size, indicated in FIGS. 14-16B are exemplary and non-limiting. Indeed, the location and relative size can be modified for any suitable embodiment, and the relative proportions of the hole 2024 in relation to the remainder of the dispensing bag 2000 can differ in various embodiments. In some embodiments, the dispensing bag 2000 may not incorporate one or more holes 2024.

The dispensing bag 2000 may be made of non-permeable or very low permeable material. In some embodiments, the material may be generally chemically inert and/or non-conductive. The dispensing bag 2000 can provide an extra barrier to keep the caps and the antiseptic cap holder assembly 2004 from being contaminated, which provides improved shelf life. The dispensing bag 2000 may provide protection against contamination of the antiseptic cap holder assemblies 2004 when being handled. The dispensing bag 2000 can be configured to function as a physical barrier that isolates at least a portion of the antiseptic cap holder assembly 2004 from the outside environment. For example, in some embodiments, the dispensing bag 2000 can be configured to inhibit contaminants from entering the chamber 2016.

In some embodiments, all or a portion of the dispensing bag 2000 may be made of a transparent material, thereby allowing a user to readily identify the bag as a holder of a particular type of medical devices (such as antiseptic caps), and/or to read information printed on the packaging of one or more types of medical devices within the bag, and/or to determine the quantity of antiseptic cap holder assemblies 2004 remaining within the dispensing bag 2000 (such as to determine when it will be necessary to replace the bag), from the outside of the bag and/or from any viewing angle. In some embodiments, the dispensing bag 2000 avoids some complications associated with hanging the dispensing bag 2000 backwards, as the dispensing bag may be viewed and/or accessed from the front and back side, as shown in FIGS. 38A and 38B.

As shown in FIG. 18, in an example of a method for producing a dispensing bag 2000, one or more (or any combination) of the following steps may be performed: (a) providing front and rear flexible transparent sheets; (b) generally positioning the front sheet over the rear sheet; (c) generally aligning the perimeters of the front and rear sheets; (d) sealing or bonding multiple edges of the sheets to each other, such as each of the respective lateral sides and top edges of the sheets, to form a container for the dispensing bag 2000; (e) temporarily leaving at least one of the respective edges (e.g., the bottom edges) or portions of such edges of the sheets unsealed or unbonded to each other to form a temporary opening in the container; (f) inserting multiple caps (e.g., individually or in cap holders 410) into the container of the dispensing bag 2000 through the temporary opening; (g) after inserting the caps into the container, sealing or bonding the previously unsealed or unbonded end through which the caps were inserted; (h) sealing or bonding a portion of the respective sheets to form a constriction at an end or in a dispensing region of the dispensing bag 2000; (i) creating a perforation or other mark or region to facilitate removing a portion of the dispensing bag 2000 to enable removal of the caps previously inserted into the dispensing bag 2000. Any of these steps can be omitted or modified and the ordering of any of the steps can be changed. Various features of the dispensing bag 2000 can comprise the various illustrated dimensions and proportions, which form part of this disclosure. It will be appreciated that these dimensions are exemplary and non-limiting. Indeed, it will be understood that the dimensions can be modified for any suitable embodiment, and that their relative proportions can differ in various embodiments.

Strip Package

Figure 19A:
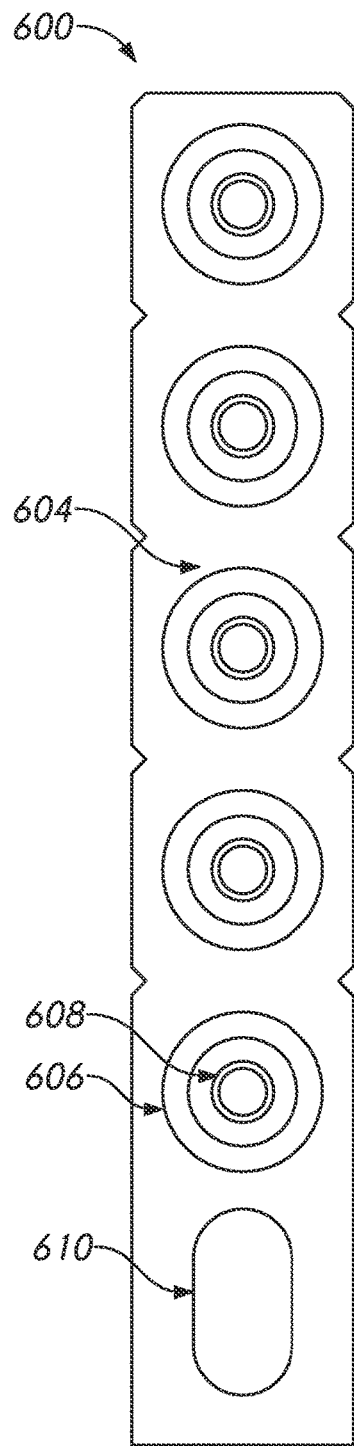
FIG. 19A is a top view of a strip package for antiseptic cap holder assemblies.
Figure 19B:
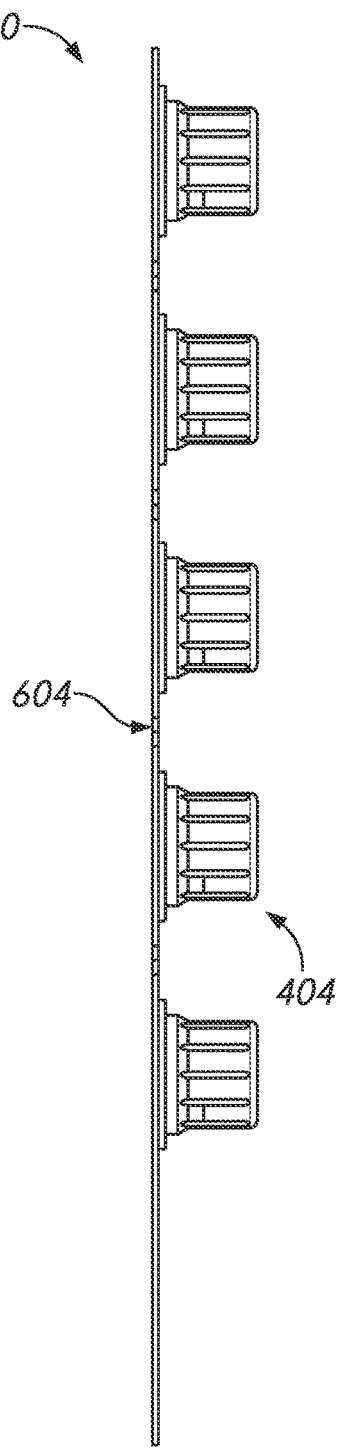
FIG. 19B is a side view of the strip package of FIG. 19A.
Figure 19C:
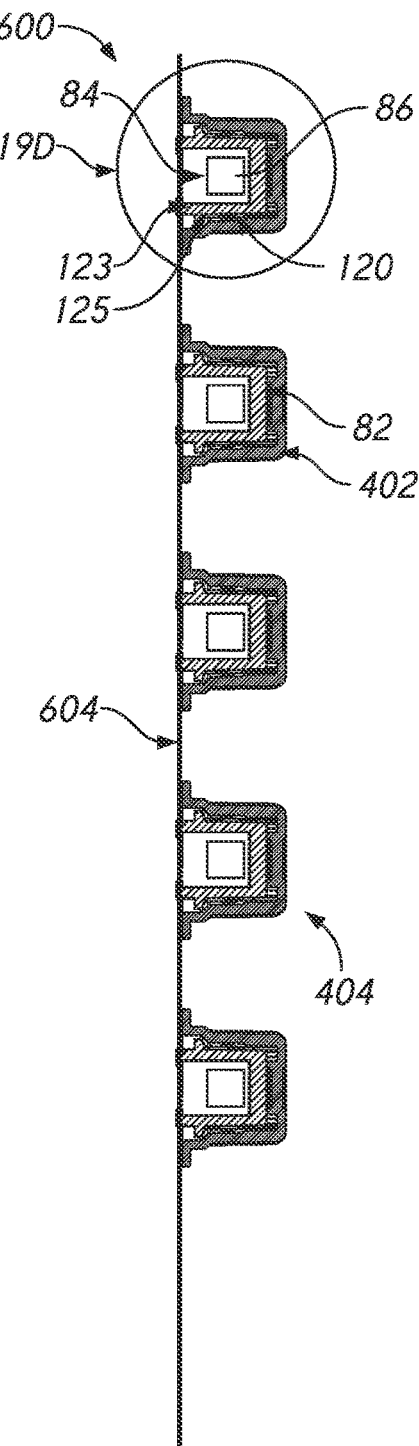
FIG. 19C is a side cross-sectional of the strip package of FIG. 19A.
Figure 19D:
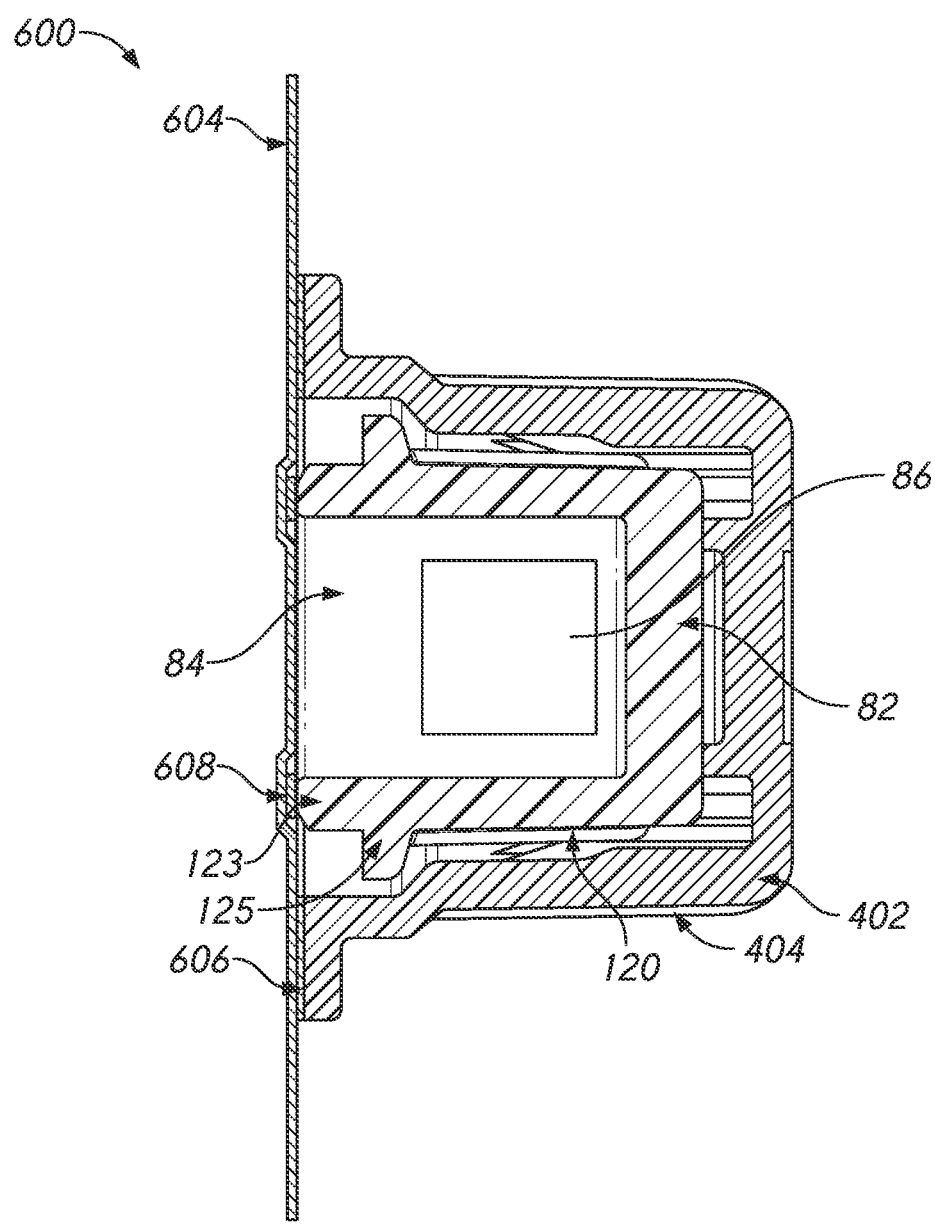
FIG. 19D is an exploded side cross-sectional view of the strip package of FIG. 19A.

FIGS. 19A-19D are various views of a delivery system for medical articles in the form of examples of a strip package 600 for antiseptic caps and/or antiseptic cap holder assemblies 404, according to some embodiments. In particular, FIG. 19A is a top view of a strip package 600 including one or more an antiseptic cap assemblies 404, and FIGS. 19B, 19C, and 19D are side, side cross-sectional, and exploded partial side cross-sectional views of the strip package 600 of FIG. 19A, respectively. Unless otherwise noted, reference numerals in FIGS. 19A-19D refer to components that are the same as or generally similar to the components in the remaining figures discussed herein. While the antiseptic cap 82 and/or the antiseptic cap holder assembly 404 shown in FIGS. 19A-19D are similar to the antiseptic cap 82 shown in FIGS. 1A-1H and the antiseptic cap holder assembly 404 shown in FIGS. 13A and 13B, the features described with reference to the strip package shown in FIGS. 19A-19D can be used with any antiseptic cap and/or cap assembly embodiments described and/or contemplated herein. For example, any one of the antiseptic cap 82 of FIG. 2, antiseptic cap 900 of FIGS. 3A-6, antiseptic cap 700 of FIGS. 7A-7E, antiseptic cap 800 of FIGS. 8A-8C, and/or any additional caps disclosed herein can be modified to function with the strip package, as shown and described with reference to FIGS. 19A-19D.

FIGS. 19A-19D show a strip package 600. The strip package 600 may function as a delivery system to contain one or more disinfectant devices, or at least a portion of one or more disinfectant devices, such as, for example, as shown in FIGS. 19A-19D, an antiseptic cap 82 and/or an antiseptic cap holder assembly 404. Any reference in this specification to the use or containment of an antiseptic cap holder assembly 404 of any type should also be interpreted to include the use, in addition or in the alternative, of an antiseptic cap. In some embodiments, the strip package 600 facilitates access to an antiseptic cap 82 and/or an antiseptic cap holder assembly 404 by advantageously allowing for removal of a single antiseptic cap 82 and/or antiseptic cap holder assembly 404 at a time, while maintaining one or more other antiseptic caps 82 and/or antiseptic cap holder assemblies 404 attached to the strip package 600.

Each of the antiseptic cap holder assemblies 404 included in the strip package 600 may include any antiseptic cap holder and/or an antiseptic cap described herein. While FIGS. 19A-19D illustrate the strip package housing five antiseptic cap holder assemblies 404, any number of disinfectant filled devices can be attached to the strip package 600. Any of the embodiments of the strip package 600 described and/or contemplated herein can be modified to be used with any antiseptic cap described and/or contemplated herein.

As shown in the figures, the strip package 600 may include a one or more antiseptic caps 82 and/or antiseptic cap holder assemblies 404 attached to a cover, or strip 604. For example, as shown in FIGS. 19A-19D, a plurality of antiseptic cap holder assemblies 404 are attached to a single strip 604. Each of the antiseptic cap holder assemblies 404, as described herein, may include an antiseptic cap holder 402 and an antiseptic cap 82. The antiseptic cap 82 can be any cap discussed herein.

The strip 604 has a width that is narrower than its length. A cap-storage device that is not a strip can comprise any other suitable shape and/or configuration capable of receiving at least a portion of an antiseptic cap 82 and/or an antiseptic cap holder assembly 404. A cap-storage device can comprise any suitable structure (e.g., straight and/or curved) and have any suitable shape (e.g., cylindrical, tapered).

A width of the strip 604, as shown in FIG. 19A-19D, may be larger than a width of the outer surface of the antiseptic cap holder assembly 404 to facilitate attaching the antiseptic cap holder assembly 404. In some embodiments, the width of the strip 604 may remain constant throughout the strip 604. In some embodiments, the width of the strip 604 may vary along the length of the strip 604. For example, the strip 604 can comprise a portion having a narrowed width. In some embodiments, the narrowed width may be located adjacent to a distal end of the strip package 600. In some embodiments, the width of the strip 604 may be sufficiently large to encompass two or more rows of antiseptic cap holder assemblies 404.

While FIGS. 19A-19D illustrate the strip package 600 as containing one row of five antiseptic cap holder assemblies 404, it is contemplated that the strip package 600 may contain any length or width sufficient to contain a plurality of antiseptic caps 82 and/or antiseptic cap holder assemblies 404. For example, the width and length of the strip 604 may be sufficiently large to encompass two or more rows of antiseptic cap holder assemblies 404, each row comprising two or more antiseptic cap holder assemblies 404. In some embodiments, the strip 604 may include notches, perforations, and/or scores between the plurality of antiseptic caps 82 and/or antiseptic cap holder assemblies 404. The notches may allow a user to tear an individual unit, or any number of a plurality of units, off for future use and still retain the individual sterile barrier of the unit(s).

As shown in FIGS. 19A-19D, the plurality of antiseptic cap assemblies 404 may be sealed with a strip 604. The strip 604 may permit each antiseptic cap 82 within an antiseptic cap holder 402 to remain sterile. The strip 604 may be configured to be sealed against one or more portions of the antiseptic cap holder 402 and/or antiseptic cap 82. In some embodiments, the strip 604 can be sealed to the antiseptic cap holder 402, as identified by reference 606 in FIGS. 19A-19D. For example, the strip 604 may be attached to the flange 418 of the antiseptic cap holder 402 by any suitable method such as by adhesives or by conductive or inductive heat sealing techniques discussed herein.

Additionally or alternatively, the strip 604 may be sealed to at least a portion of the antiseptic cap 82, as identified by reference 608 in FIGS. 19A-19D. Attachment directly to the antiseptic cap 82 permits the strip 604 to seal the first chamber 84 and prevent the removal of any antiseptic material 86 and/or antiseptic fluid within the antiseptic cap 82. In some embodiments, the strip 604 may form a double seal (e.g., seal 606 and seal 608) when the strip 604 is sealed against both the cap holder 402 and the antiseptic cap 82 within the cap holder 402. For example, a double seal may provide an extra barrier to prevent contamination of an antiseptic cap 82 and/or prevent an antiseptic material from escaping from the antiseptic cap 82. Providing a double seal may advantageously improve shelf life.

As shown in FIGS. 19A-19D, the strip package 600 can include one or more hanging holes 610. For example, the hole 610 may include a die cut hole or holes. The hole 610 can be sized and configured to allow the strip package 610 to be hung on a convenient hanger. For example, a user may utilize the one or more holes 610 to hang the strip package 600 on an IV pole. The hole 610 can comprise any suitable shape and/or configuration capable of allowing the strip package 600 to be hung on a hanger. It will be appreciated that location of the hole 610, as well as the relative size, indicated in FIGS. 91A-19D are exemplary and non-limiting. Indeed, it will be understood, that the location and relative size can be modified for any suitable embodiment, and that the relative proportions of the hole 610 in relation to the remainder of the strip package 600 can differ in various embodiments. In some embodiments, the strip package 600 may not incorporate one or more holes 610.

In some embodiments, the strip 604 may be thermally bonded to one or more of the antiseptic cap holder 402 and the antiseptic cap 82. Thermal bonding may occur using standard heat sealing technology, such as impulse, induction, conduction, radiant, or other heat sealing techniques. In some embodiments, the strip 604 could be attached to the cap holder 402 and/or the antiseptic cap 82 by utilizing an adhesive bond or by a suitable mechanical or friction connection, such as a snap-fit.

To remove an antiseptic cap holder assembly 404 from the strip package 600, a user may grasp a portion of the antiseptic cap holder assembly 404 that is extending from the strip 604 and apply a removal force, such as a downward force (if the strip package 600 is positioned in a vertically hanging orientation). In some embodiments, as discussed herein, a user may utilize a notch and/or perforation to remove at least a portion of the strip 604 when removing an antiseptic cap holder assembly 404. This advantageously maintains at least one seal on the antiseptic cap holder assembly 404 upon removal from the strip package 600. In some embodiments, the strip package 600 facilitates removal of the antiseptic cap holder assembly 404 through an efficient process that only requires the use of a single hand.

In some embodiments, the dispensing bag 2000 may advantageously eliminate the need for direct contact with the antiseptic cap 82 during removal from the strip package 600. The antiseptic cap holder 402 may prevent contamination of an antiseptic cap 82 within the antiseptic cap holder 402. For example, a user may handle the antiseptic cap holder assembly 404 via one or more portions of the antiseptic cap holder 402, such as the flange 418 extending out from the antiseptic cap holder 402. The antiseptic cap holder 402 may act as a guard against contact of the antiseptic cap 82 by a user.

The antiseptic cap holder assembly 404 may be withdrawn from the strip package 600 such that the removal (e.g., downward) force required to remove the antiseptic cap holder assembly 404 from the strip 604 is lesser than the strength of the hole 610, such that the hole 610 does not tear and when the strip package 600 is in a vertically hanging position. For example, the peel force could generally be less than two pounds of force to start peeling, and less than one pound of force to continue peeling.

In some embodiments, the strip 604 could be made of any suitable material. For example, the strip 604 may comprise a foil, a plastic, a laminate, etc. In some instances, the strip 604 can be made of a foil material having a thickness of approximately 1 to 2 mil. The strip 604 can have a thick foil with a top coat of PET (polyethylene terephthalate), such as 48-gauge PET, then a polymer coat such as PDX which could be white, and a bottom coat of a peelable sealing layer, such as Allegro B, manufactured by Rollprint Packaging Products, Inc. The sealing layer can form an adhesive bond that can be peelable. The antiseptic caps 82 and/or antiseptic cap holder assemblies 404 may be attached to the strip 604 by induction heating of the foil, which melts the peelable sealing layer to adhere it to the antiseptic caps 82 and/or antiseptic cap holder assemblies 404.

In some embodiments, all or a portion of the strip package 600 may be made of a transparent material, thereby allowing a user to readily identify the strip package 600 as a holder of a particular type of medical devices (such as antiseptic caps and/or antiseptic cap holder assemblies), and/or to read information printed on the packaging of one or more types of medical devices within the bag, and/or to determine the quantity of antiseptic cap holder assemblies 404 remaining on the strip package 600 (such as to determine when it will be necessary to replace the strip package 600), from any viewing angle. In some embodiments, the strip package 600 avoids some complications associated with hanging the strip package 600 backwards, as the strip package 600 may be viewed and/or accessed from the front and back side.

Various features of the strip package 600 can comprise the various illustrated dimensions and proportions, which form part of this disclosure. It will be appreciated that these dimensions are exemplary and non-limiting. Indeed, it will be understood that the dimensions can be modified for any suitable embodiment, and that their relative proportions can differ in various embodiments.

Syringe Assembly

Figure 20A:
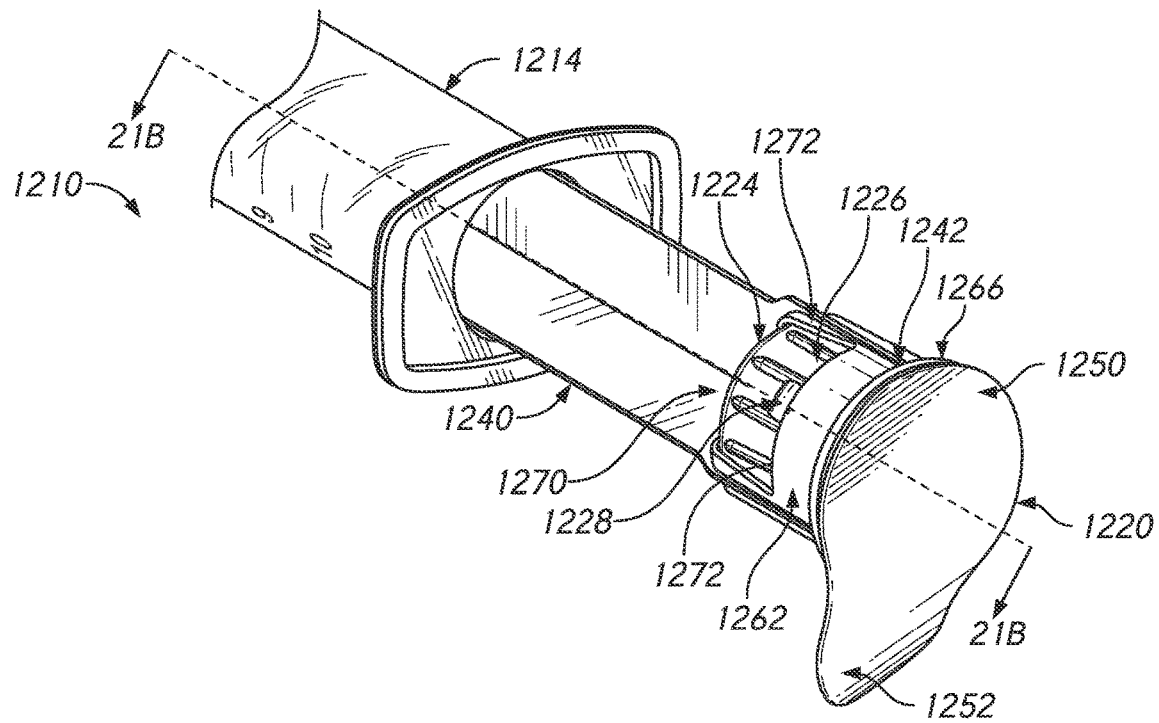
FIG. 20A is a front perspective view of an embodiment of a syringe assembly having an antiseptic cap holder assembly.
Figure 20B:
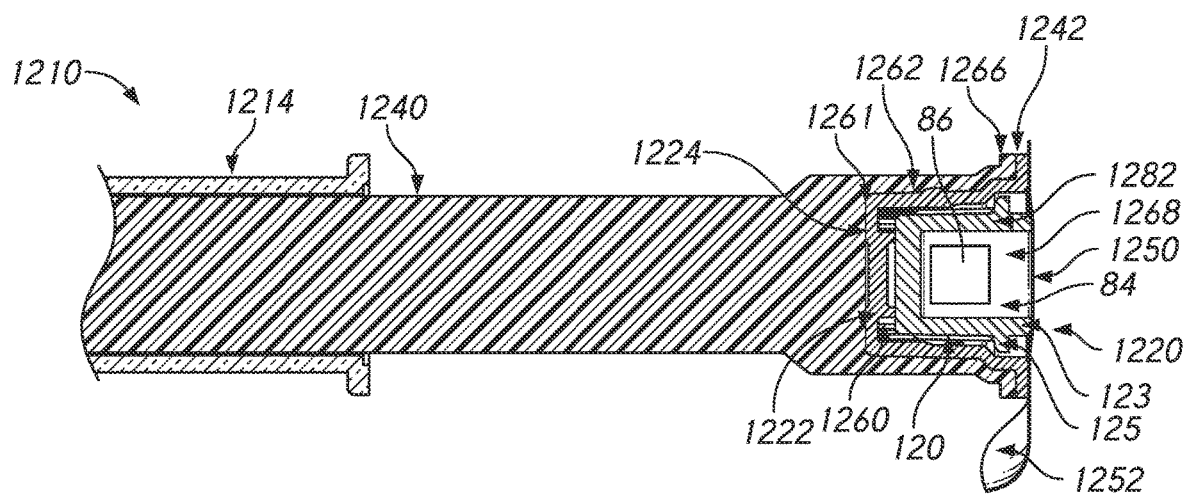
FIG. 20B is a cross-sectional view of the syringe assembly and the antiseptic cap holder assembly of FIG. 20A.

FIGS. 20A and 20B are various views of a syringe assembly 1210 including an antiseptic cap holder assembly 1220, according to some embodiments. In particular, FIG. 20A is a front perspective view of a syringe assembly 1210 including an antiseptic cap holder assembly 1220, and FIG. 20B is a side cross-sectional view of the syringe assembly 1210 of FIG. 20A. Unless otherwise noted, reference numerals in FIGS. 20A and 20B refer to components that are the same as or generally similar to the components in the remaining figures discussed herein. While the antiseptic cap holder assembly 1220 shown in FIGS. 20A and 20B are similar to antiseptic cap holder assembly 404 shown in FIGS. 13A and 13B, it will be understood that the features described with reference to syringe assembly 1210 shown in FIGS. 20A and 20B can be used with any antiseptic cap and/or cap assembly embodiments described and/or contemplated herein. For example, any one of the antiseptic cap 82 of FIGS. 1A-1H, antiseptic cap 82 of FIG. 2, antiseptic cap 900 of FIGS. 3A-6, antiseptic cap 700 of FIGS. 7A-7E, antiseptic cap 800 of FIGS. 8A-8C, and/or any additional caps disclosed herein can be modified to function with the syringe assembly 1210, as shown and described with reference to FIGS. 20A and 20B.

FIGS. 20A and 20B show a syringe barrel assembly 1210 having an antiseptic cap equipped syringe assembly 1240 configured for removably receiving an antiseptic cap holder assembly 1220. The syringe assembly 1210 may include a syringe barrel 1214 and a plunger 1240. The barrel 1214 can include a sidewall defining a chamber and a proximal opening in fluid communication with the chamber. In some embodiments, the chamber of the syringe assembly 1210 may be filled with a locking solution or a flush solution for use with an indwelling, central venous catheter. Some examples of suitable locking or flushing solutions are set forth below. The flush or locking solution is injected into a fluid access site of the catheter to clean and disinfect the catheter and can be withdrawn from the catheter or allowed to remain in an end portion of the catheter to serve as a barrier to the ingress of pathogens and contaminants.

The plunger 1240 may include an elongate shaft, a proximal end 1242, and a distal end (not shown in FIGS. 20A and 20B). The elongate shaft, in some embodiments, is generally cruciform in cross-sectional shape. A stopper or piston may be connected to the distal end of the plunger 1240. In some embodiments, the piston is dimensioned such that when inserted into the syringe barrel chamber, an outer circumferential surface of the piston is in fluid-tight engagement with an inner surface of the syringe barrel 1214. The piston assembly when moved proximally (or when being withdrawn) can draw fluid into the chamber and when moved distally (or when inserted into the syringe chamber) can drive fluid out of the chamber. FIGS. 20A and 20B show the piston assembly 1240 partially inserted into the syringe barrel 1214.

As shown in FIGS. 20A and 20B, in some embodiments, the proximal end 1242 of the plunger may include a chamber 1260, sized to receive and removably hold an antiseptic cap holder assembly 1220. Referring to FIG. 21, the chamber 1260 can be comprise a bottom wall 1261 and an annular sidewall 1262 that has a peripheral proximal end 1266 that includes an opening 1268 through which the antiseptic cap holder assembly 1220 can be inserted into the chamber 1260. It will also be understood that any of the antiseptic caps and/or antiseptic cap holder assembly embodiments described and/or contemplated herein can be modified to be used with the syringe assembly shown in FIGS. 20A and 20B.

FIGS. 20A and 20B illustrate an antiseptic cap holder assembly 1220 within the chamber 1260 of the plunger assembly 1240. The antiseptic cap holder assembly 1220 can include any antiseptic cap holder assembly disclosed herein. For example, antiseptic cap holder assembly may comprise antiseptic cap holder assembly 404 disclosed in reference to FIGS. 13A and 13B. For example, as discussed herein, the cap holder assembly 1220 may comprises one or more of the following features: an antiseptic cap holder 1222, an antiseptic cap 1282, an antiseptic material 1286, and a cover 1250. In some embodiments, a pull tab 1252 could be provided for facilitating removal of the film 1250 from the cap holder 1222 to provide access to the antiseptic cap 1282. The cap holder 1222 could have a distal end 1224 and one or more bulges 1228 on the outer surface 1226 to secure the cap holder assembly 1220 in the chamber 1260. In some embodiments, the incorporation of separate plunger assembly 1240 and antiseptic cap holder assembly 1220 allows for the separate manufacture, assembly, and sterilization of the antiseptic cap holder assembly 1220 from the plunger assembly 1240 and the syringe barrel 1214.

In some embodiments, as illustrated in FIG. 20A, the sidewall 1262 of the plunger 1240 includes one or more apertures 1270 comprising edges 1272. The one or more apertures 1270 provide access to the chamber 1260 and facilitate removal of the cap holder assembly 1220 from the plunger 1240 as will be described hereinafter.

The cap holder assembly 1220 can be removed from the plunger 1240. In some embodiments, removal of the cap holder assembly 1220 from the plunger 1240 involves placing one's thumb or finger through the one or more apertures 1270 against a lower surface of the cap holder assembly 1220. A user may push against the cap holder assembly 1220 with a finger or thumb to urge the cap holder assembly 1220 out of the chamber 1260. Ultimately, the cap holder assembly 1220 is ejected from the chamber 1260. In this way, the antiseptic cap 1282 could be conveniently used at a different time than the syringe 1210.

In some embodiments, the chamber 1260 of the plunger 1240 may include an interior surface comprising a plurality of circumferentially spaced ribs. The plurality of ribs may be configured to contact an antiseptic cap holder assembly 1220 and secure the antiseptic cap holder assembly 1220 within the chamber 1260. The ribs, in some instances, could each contain a slot shaped to receive a corresponding rib located on an outer surface of the antiseptic cap holder assembly 1220 to secure the cap holder assembly 1220 within the chamber 1260. The ribs of the chamber 1260 could also be tapered to facilitate the controlled removal of the antiseptic cap holder assembly 1220, and prevent the antiseptic cap holder assembly 1220 from ejecting too rapidly. The ribs can provide a decreasing amount of resistance against the cap holder 1222 as the antiseptic cap holder assembly 1220 is urged out of the chamber 1260. It will also be understood that any of the embodiments described and/or contemplated herein can be modified to be used with chamber 1260 shown in FIGS. 20A and 20B.

As partially shown in FIG. 20A, the plunger 1240 may include four support walls extending at 90 degree angles with respect to each other from a common point. Towards the proximal end 1242 of the plunger 1240, one or more support walls may have one or more recessed areas proximal the one or more apertures 1270 to facilitate removal of the cap holder assembly by providing more clearance for a user to place his or her thumb beneath the cap holder assembly. In some embodiments, an outermost edge of the recessed area is closer to the common point than the outermost edge of the rest of the sidewall. The recessed area can comprise a flat edge a, sloped edge, or both.

In some embodiments, the plunger 1240 may not include a chamber and an antiseptic cap holder and/or antiseptic cap holder assembly may be retrofitted to be attached to a distal end of the plunger 1240. The plunger 1204, in some instances, may comprise a button at the distal end and the cap and/or the antiseptic cap holder assembly may be configured to engage the button. For example, the cap and/or antiseptic cap holder assembly may include a proximal end that is removably or fixedly attached to a button of the plunger. The proximal end may include an opening dimensioned to fit about the button and can comprise a member for attaching to the button. In some embodiments, the attaching member includes a plurality of circumferentially spaced, and axially inwardly directed tabs extending from an inner wall surface. In some embodiments, the tabs engage a lower surface of the button to attach the cap holder and/or antiseptic cap holder assembly to the plunger.

The syringe assembly 1210 can be fabricated from any material suitable for its purpose and includes glass and polymeric material. Suitable polymeric materials include, but are not limited to, homopolymers, copolymers and terpolymers formed from monomers such as olefins, cyclic olefins, amides, esters, and ethers. The polymeric material may be a blend of more than one polymeric material and can be a monolayer structure or a multilayer structure. In some embodiments, the syringe barrel and the plunger are injection molded from a polypropylene material.

Antiseptic Material

Unless otherwise noted, the antiseptic material described below refers to components that are the same as or generally similar to the components discussed herein in the present application. It will be understood that the features described below can be used with any of the embodiments described and/or contemplated herein. For example, any one of the antiseptic caps disclosed herein can be modified to include an absorbent material, as described below.

An antiseptic material may include medical grade materials capable of storing and releasing an antiseptic liquid, or liquid having other medical purposes, and includes materials such as sponges, rupturable capsules and other materials or devices capable of serving this purpose. Suitable sponges can include any sponge suitable for use for medical purposes and can be naturally occurring or synthetic. The antiseptic material can be cut into suitable shapes or can be molded into the desired shape. It is desirable that the antiseptic material be attached to an antiseptic cap to prevent the antiseptic material from inadvertently falling out and/or off of the antiseptic cap. For example, the antiseptic material may be attached to an antiseptic cap by any suitable method such as ultrasonic or vibrational welding or other suitable technique.

As discussed herein, the absorbent material can comprise any material suitable for storing and/or releasing antiseptic liquid. In some embodiments, the antiseptic material can comprise any suitable polymer. In some embodiments, the polymer may include a polymer foam. For example, the antiseptic material may include a polyurethane, polyester, polycarbonate, and/or polyamide. The antiseptic material may comprise an open-cell foam. In some embodiments, the foam may comprise a density of about 0.8 to about 2.8 pounds per cubic foot.

In some embodiments, one or more portions of the any one of the antiseptic caps described herein may be coated and/or impregnated with an antiseptic fluid, an anticoagulant fluid, and/or an antimicrobial fluid. The one or more portions of the antiseptic cap that may be coated and/or impregnated include an inner surface of a cap wall, threads, an outer surface of the cap wall, an inner surface of the cap wall, and/or any additional features of the caps disclosed herein.

The antiseptic can comprise any substance suitable for its purpose. Suitable substances include, but are not limited to, isopropyl alcohol (IPA), Chlorhexidine, silver, citrate salt solution, etc. In some embodiments, the antiseptic agent can contain antibacterial agents such as those classified as aminoglycosides, beta lactams, quinolones or fluoroquinolones, macrolides, sulfonamides, sulfamethaxazoles, tetracyclines, treptogramins, oxazolidinones (such as linezolid), clindamycins, lincomycins, rifamycins, glycopeptides, polymxins, lipo-peptide antibiotics, as well as pharmacologically acceptable sodium salts, pharmacologically acceptable calcium salts, pharmacologically acceptable potassium salts, lipid formulations, derivatives and/or analogs of the above. In another embodiment, the antiseptic agent can contain antifungal agents. In another embodiment, the antiseptic agent can contain antiviral agents. The antiseptic may be a blend of more than one antiseptic material.

In some embodiments, a quantity of physiological, antimicrobial metal compound is added to the resin for direct molding of an article. Physiological, antimicrobial metals are meant to include the precious metals, such as silver, gold and platinum, and copper and zinc. Physiological, antimicrobial metal compounds used herein may include oxides and salts of silver and also gold, for example: silver acetate, silver benzoate, silver carbonate, silver citrate, silver chloride, silver iodide, silver nitrate, silver oxide, silver sulfadiazine, silver sulfate, gold chloride and gold oxide. Platinum compounds such as chloroplatinic acid or its salts (e.g., sodium and calcium chloroplatinate) may also be used. Also, compounds of copper and zinc may be used, for example: oxides and salts of copper and zinc such as those indicated above for silver. Single physiological, antimicrobial metal compounds or combinations of physiological, antimicrobial metal compounds may be used.

In some embodiments, physiological, antimicrobial metal compounds used may include silver acetate, silver oxide, silver sulfate, gold chloride and a combination of silver oxide and gold chloride. The particles of the silver compounds are sufficiently able to be extracted to form a zone of inhibition to prevent and kill bacteria growth.

In some embodiments, the devices herein are impregnated with triclosan and silver compounds or triclosan and chlorhexidine.

Further details regarding the embodiments disclosed herein, including an antiseptic cap, can be used are found in the '546 application, the '359 Application, the '952 Application, the '847 Application, the '897 Application, and the '157 application. It will be understood that any of the functions, materials, methods, systems, and devices described and/or contemplated within the '546 application, the '359 Application, the '952 Application, the '847 Application, the '897 Application, and the '157 application can be modified to be used with the various functions, materials, methods, systems, and devices systems described herein. For example, the antiseptic cap may further comprise any embodiment described and/or contemplated within '546 application, the '359 Application, the '952 Application, the '847 Application, the '897 Application, and the '157 application. Additionally, any of the functions, materials, methods, systems, and devices described and/or contemplated herein can be modified to be used with the various functions, materials, methods, systems, and devices systems described and/or contemplated within the '546 application, the '359 Application, the '952 Application, the '847 Application, the '897 Application, and the '157 application.

OTHER VARIATIONS

Although this invention has been disclosed in the context of certain embodiments and examples, it will be understood by those skilled in the art that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the disclosed invention. Thus, it is intended that the scope of the present invention herein disclosed should not be limited by the particular disclosed embodiments described above, but should be determined only by a fair reading of the claims that follow. Moreover, language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result.

The following is claimed:

1. A sanitizing cap comprising:
   a housing comprising:
      a bottom wall, and
      a sidewall extending from the bottom wall, the sidewall surrounding an interior chamber and an opening into the interior chamber, the sidewall comprising a non-threaded interior surface extending from the bottom wall, along the sidewall, and to the opening, the interior surface comprising a deformable portion being configured to securely attach to a thread of a medical device;
   a cleaning material being configured to releasably retain an antiseptic liquid, the cleaning material being positioned in the interior chamber and being separate from the deformable portion of the interior surface; and
   a seal being removably attached to an outer surface of the housing and extending over the interior chamber such that the cleaning material is exposed upon removal of the seal.

2. The sanitizing cap of claim 1, wherein the deformable portion of the interior surface is configured to securely attach to the medical device such that a fluid tight seal is formed between the deformable portion of the interior surface and the medical device.

3. The sanitizing cap of claim 2, wherein the fluid tight seal is configured to inhibit release of the antiseptic liquid from the interior chamber.

4. The sanitizing cap of claim 1, wherein the deformable portion of the interior surface is configured to expand and receive the thread of the medical device when the sanitizing cap is securely attached to the medical device.

5. The sanitizing cap of claim 1, wherein the deformable portion of the interior surface is configured to securely attach to the thread of the medical device as the sanitizing cap is applied to the medical device in a direction along a longitudinal axis of the sanitizing cap.

6. The sanitizing cap of claim 5, wherein the deformable portion of the interior surface is configured to securely attach to the thread of the medical device without requiring rotation of the sanitizing cap or the medical device.

7. The sanitizing cap of claim 1, wherein the deformable portion of the interior surface does not comprise a screw thread.

8. The sanitizing cap of claim 1, wherein the housing further comprises one or more ribs, and wherein each of the one or more ribs extend at least partially along an external surface of the sidewall.

9. The sanitizing cap of claim 8, wherein the one or more ribs are configured to facilitate attachment of the sanitizing cap to the medical device.

10. The sanitizing cap of claim 8, wherein the one or more ribs comprises a plurality of ribs.

11. The sanitizing cap of claim 1, wherein the housing comprises a ledge configured to retain the cleaning material within the interior chamber.

12. The sanitizing cap of claim 1, wherein the housing comprises an undercut configured to retain the cleaning material within the interior chamber.

13. The sanitizing cap of claim 1, wherein the cleaning material is retained within the interior chamber through friction fit.

14. The sanitizing cap of claim 1, wherein the cleaning material comprises a sponge.

15. The sanitizing cap of claim 1, wherein the deformable portion of the interior surface is configured to securely attach to the medical device such that a second seal is formed between the deformable portion of the interior surface and the medical device, and wherein the second seal is configured to inhibit release of the antiseptic liquid from the interior chamber,
   wherein the deformable portion of the interior surface is configured to expand and receive the thread of the medical device when the sanitizing cap is securely attached to the medical device,
   wherein the deformable portion of the interior surface does not comprise a screw thread,
   wherein the housing further comprises a plurality of ribs configured to facilitate attachment of the sanitizing cap to the medical device, and wherein each of the plurality of ribs extend at least partially along an external surface of the sidewall,
   wherein the cleaning material is retained within the interior chamber through friction fit, and
   wherein the cleaning material comprises a sponge.

16. A combination of the sanitizing cap of claim 1 and the medical device.

* * * * *